(12) United States Patent
Oishi et al.

(10) Patent No.: US 10,858,669 B2
(45) Date of Patent: Dec. 8, 2020

(54) GENETICALLY MODIFIED CHICKEN EGG WITH AN EXOGENOUS SEQUENCE KNOCKED INTO THE OVALBUMIN GENE

(71) Applicant: NATIONAL INSTITUTE OF ADVANCED INDUSTRIAL SCIENCE AND TECHNOLOGY, Tokyo (JP)

(72) Inventors: Isao Oishi, Kobe (JP); Kyoko Yoshii, Ikeda (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 16/065,179

(22) PCT Filed: Dec. 22, 2016

(86) PCT No.: PCT/JP2016/088590
§ 371 (c)(1),
(2) Date: Jun. 22, 2018

(87) PCT Pub. No.: WO2017/111144
PCT Pub. Date: Jun. 29, 2017

(65) Prior Publication Data
US 2019/0010515 A1 Jan. 10, 2019

(30) Foreign Application Priority Data
Dec. 25, 2015 (JP) .................................. 2015-254361

(51) Int. Cl.
| | | |
|---|---|---|
| *A01K 67/027* | (2006.01) | |
| *C12N 15/00* | (2006.01) | |
| *C12N 15/85* | (2006.01) | |
| *C07K 16/00* | (2006.01) | |
| *C07K 14/565* | (2006.01) | |
| *C07K 14/78* | (2006.01) | |
| *C07K 14/81* | (2006.01) | |
| *C12N 15/86* | (2006.01) | |

(52) U.S. Cl.
CPC ...... *C12N 15/8509* (2013.01); *A01K 67/0275* (2013.01); *C07K 14/565* (2013.01); *C07K 14/78* (2013.01); *C07K 14/8135* (2013.01); *C07K 16/00* (2013.01); *C12N 15/86* (2013.01); *A01K 2217/072* (2013.01); *A01K 2217/075* (2013.01); *A01K 2227/30* (2013.01); *A01K 2267/01* (2013.01); *A01K 2267/02* (2013.01); *C07K 2317/11* (2013.01); *C07K 2317/21* (2013.01); *C07K 2319/02* (2013.01); *C07K 2319/50* (2013.01); *C12N 2015/8518* (2013.01)

(58) Field of Classification Search
USPC .......................................................... 800/19
See application file for complete search history.

(56) References Cited

U.S. PATENT DOCUMENTS

| | | | | |
|---|---|---|---|---|
| 9,380,769 | B2 * | 7/2016 | Leighton | A01K 67/0276 |
| 9,809,642 | B2 * | 11/2017 | Leighton | A01K 67/0276 |
| 2015/0072064 | A1 | 3/2015 | Tyack | |
| 2018/0242562 | A1 * | 8/2018 | Horiuchi | A01K 67/027 |

FOREIGN PATENT DOCUMENTS

| | | |
|---|---|---|
| JP | 2015-514404 | 5/2015 |
| KR | 10-2016-0073469 | 6/2016 |
| WO | 2015/199225 | 4/2017 |

OTHER PUBLICATIONS

Oishi (Scientific Reports, Apr. 2016, vol. 6 23980, p. 1-10).*
Schusser (PNAS, Dec. 10, 2013, vol. 110, No. 50, p. 20170-20175).*
Park (PNAS, 2014, vol. 111, No. 35, p. 12716-12721).*
Park (PNAS, Jun. 12, 2012, vol. 109, No. 24, 9337-9341).*
Fan (Animal Biotechnology, 2011, vol. 22, p. 211-222).*
Teglund "Breeding genetically modified animals for food production" (Jun. 24, 2014, Swedish University of Agriculture Sciences, p. 1-3).*
Jinek (eLife, Jan. 2013, p. 1-9).*
Notification of Reasons for Refusal dated Jun. 4, 2019 in Japanese Patent Application No. 2017-558320, with English-language translation.
International Search Report dated Mar. 21, 2017 in International (PCT) Application No. PCT/JP2016/088590.
International Preliminary Report on Patentability dated Jun. 26, 2018 in International (PCT) Application No. PCT/JP2016/088590.
Lillico, S.G. et al., "Oviduct-specific expression of two therapeutic proteins in transgenic hens", Proceedings of the National Academy of Sciences of the USA, 2007, vol 104, No. 6, pp. 1771-1776.
Kamihira M. et al., "High-Level Expression of Single-Chain Fv—Fc Fusion Protein in Serum and Egg White of Genetically Manipulated Chickens by Using a Retroviral Vector", Journal of Virology, 2005, vol. 79, No. 17, pp. 10864-10874.
Van de Lavoir MC et al., "Germline transmission of genetically modified primordial germ cells", Nature, 2006, vol. 441 (7094), pp. 766-769.
Park, T. S. et al., "Targeted gene knockout in chickens mediated by TALENs", Proceedings of the National Academy of Sciences of the USA, 2014, vol. 111, No. 35, pp. 12716-12721.

(Continued)

*Primary Examiner* — Michael C Wilson
(74) *Attorney, Agent, or Firm* — Wenderoth, Lind & Ponack, L.L.P.

(57) ABSTRACT

Provided are a poultry knock-in egg and knock-out egg. The present invention pertains to a knock-out poultry egg in which at least one oviduct-specific gene has been knocked out, said gene being selected from the group consisting of ovalbumin, ovomucoid, ovomucin, ovotransferrin, ovoinhibitor, and lysozyme, and at least one egg allergen protein has been reduced or eliminated, said protein being selected from the group consisting of ovalbumin, ovomucoid, ovomucin, ovotransferrin, ovoinhibitor, and lysozyme.

13 Claims, 20 Drawing Sheets

Specification includes a Sequence Listing.

(56) References Cited

OTHER PUBLICATIONS

Fan, B. et al., "Assembly and in vitro functional analysis of zinc finger nuclease specific to the 3' untranslated region of chicken ovalbumin gene", Animal Biotechnology, 2011, vol. 22, issue 4. pp. 211-222.

Hiroyuki Horiuchi, "Idenshi Kaihen-kei no Kaihatsu de Tamago Allergy Kokufuku ni Idomu Allergy Free no Tamago Kaihatsu ga Kano ka", The Niwatori-no-Kenkyu, special extra issue, 2010, No. 5, pp. 5-7, with partial English Translation.

* cited by examiner

[Fig. 1]

```
         10        20        30        40        50        60
gacatacagctagaaagctgtattgcctttagcactcaagctcaaaagACAACTCAGAGT    ← OVATg1
         70        80        90       100       110       120
TCACCATgggctccatcggcgcagcaagcatggaattttgttttgatgtattcaaggagc
        M  G  S  I  G  A  A  S  M  E  F  C  F  D  V  F  K  E
        130       140       150       160       170       180
tcaaagtccaccatgccaatgagaacatcttctactgccccattgccatcatgtcagctc
  L  K  V  H  H  A  N  E  N  I  F  Y  C  P  I  A  I  M  S  A
        190       200       210       220       230       240
tagccatggtatacctgggtgcaaaagacagcaccaggacacagataaataaggttgttc
  L  A  M  V  Y  L  G  A  K  D  S  T  R  T  Q  I  N  K  V  V
```

[Fig. 2]

```
         10        20        30        40        50        60
atggccatggcaggcgtcttcgtgctgttctctttcgtgctttgtggcttcctcccagat   OVMTg2
 M  A  M  A  G  V  F  V  L  F  S  F  V  L  C  G  F  L  P  D
         70        80        90       100       110       120
gctgtctttggggctgaggtggactgcagtaggTTTCCAACGCTACAGACAaggaaggc
  A  V  F  G  A  E  V  D  C  S  R  F  P  N  A  T  D  K  E  G
        130       140       150       160       170       180
aaagatgtattggtttgcaacaaggacctccgccccatctgtggtaccgatggagtcact
  K  D  V  L  V  C  N  K  D  L  R  P  I  C  G  T  D  G  V  T
        190       200       210       220       230       240
```

[Fig. 3]

EXAMPLE OF OVALBUMIN GENE MUTATIONS

```
OVATg1                                         Met
  WT:   gctgtttgctctagACAACTCAGAGTTCACCATgggctccatcggt
  mt:   gctgtttgctctagacaactcagagt----catgggctccatcggt
  mt:   gctgtttgctctagacaactcagagttcac-atgggctccatcggt
  mt:   gctgtttgctctagacaactcagagttcacATtgggctccatcggt
  mt:   gctgtttgctctagacaactcagagttcac--tgggctccatcggt
  mt:   gctgtttgctctagacaactca---------atgggctccatcggt
  mt:   gctg---------------------catgggctccatcggt
```

[Fig. 4A]

EXAMPLE OF OVOMUCOID GENE MUTATIONS
OVMTg2
```
wt:   tgcagtaggTTTCCCAACGCTACAGACAaggaaggcaaagatgtattggtttgcaa
mt:   tgcagtaggtttcccaacgctacaga-aaggaaggcaaagatgtattggtttgcaa
mt:   tgcagtaggtttcccaacgctaca-acaaggaaggcaaagatgtattggtttgcaa
mt:   tgcagtaggtttcccaacgctaca--caaggaaggcaaagatgtattggtttgcaa
mt:   tgcagtaggtttcccaacgcta---acaaggaaggcaaagatgtattggtttgcaa
mt:   tgcagtaggtttcccaacgctaca----aggaaggcaaagatgtattggtttgcaa
mt:   tgcagtaggtttcccaacgcta-----aaggaaggcaaagatgtattggtttgcaa
mt:   tgcagtaggtttcccaacg-----gacaaggaaggcaaagatgtattggtttgcaa
mt:   tgcagtaggtttcccaacg-------caaggaaggcaaagatgtattggtttgcaa
mt:   tgcagtaggtttcccaacgc-------aaggaaggcaaagatgtattggtttgcaa
mt:   tgcagtaggtttcccaacgct---------------------gtattgg-ttgcaa
```

[Fig. 4B]
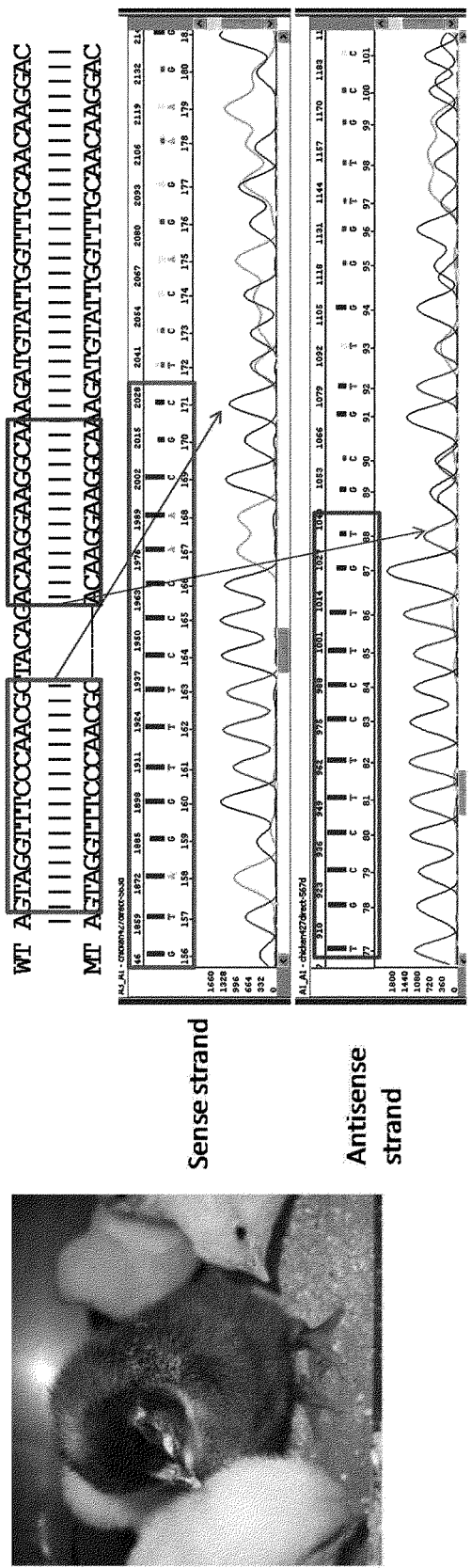

[Fig. 5A]
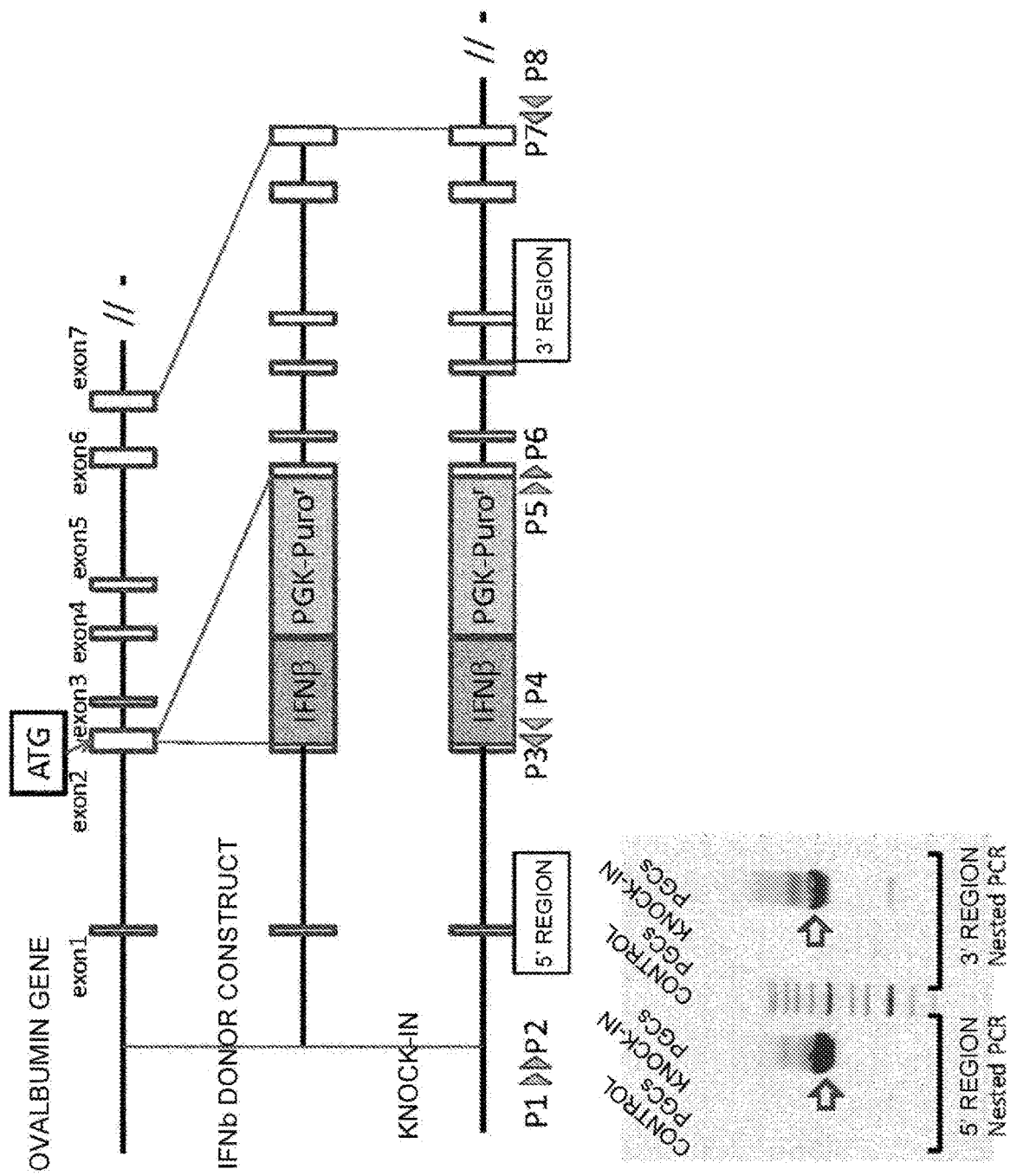

[Fig. 5B]
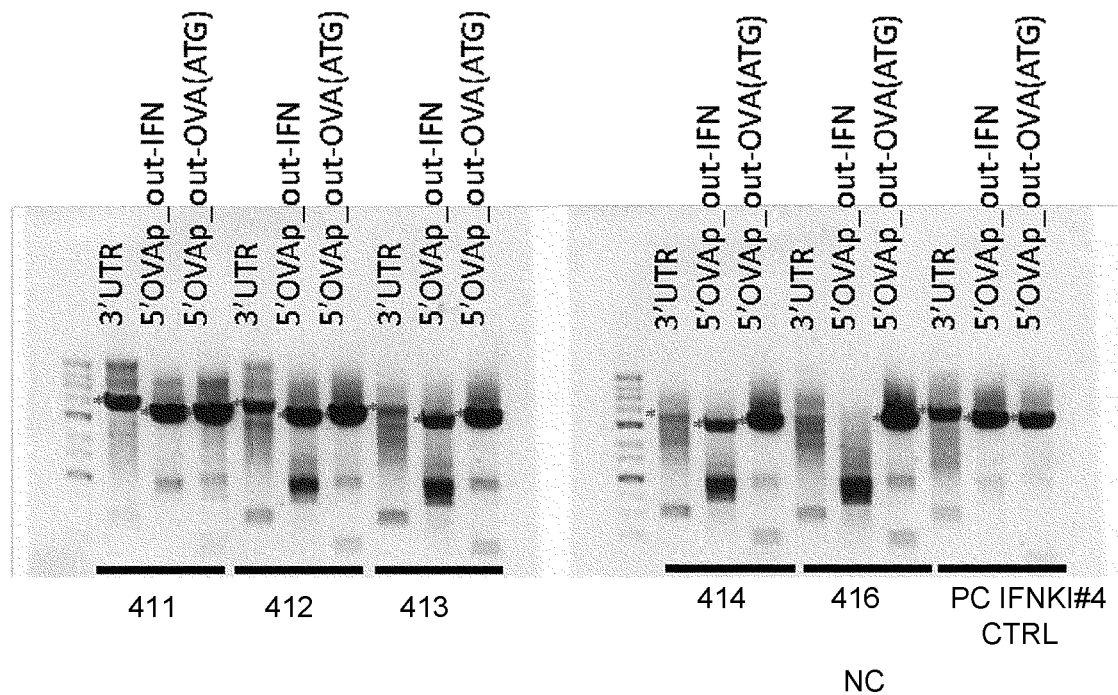

[Fig. 5C]
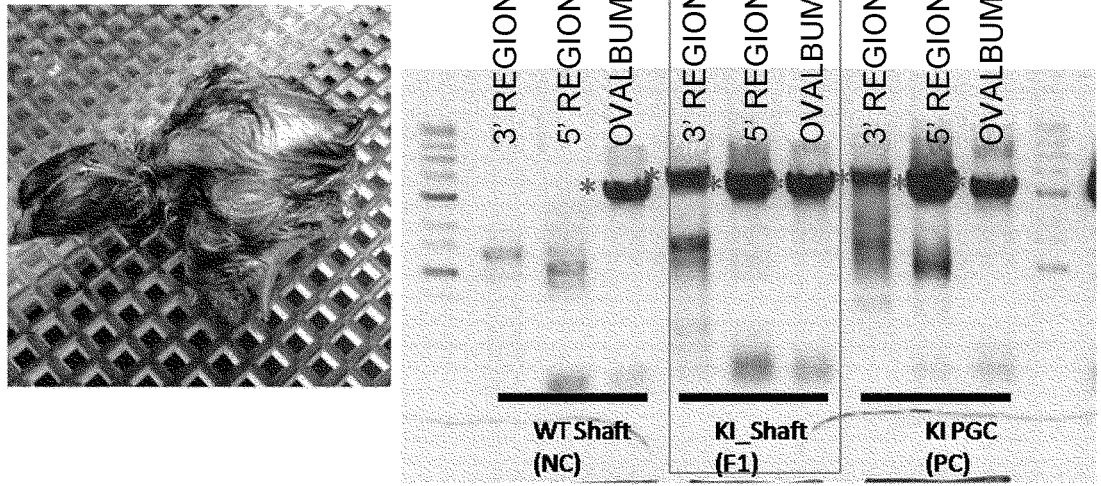
FEMALE OFFSPRING DERIVED FROM 411 (F1)
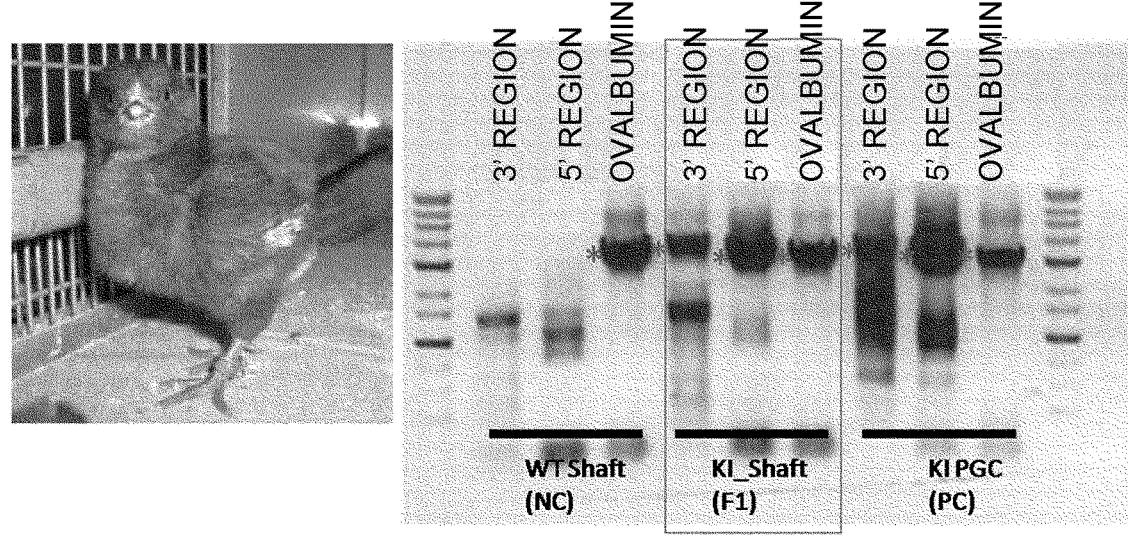
FEMALE OFFSPRING DERIVED FROM 412 (F1)

[Fig. 6A]

```
           10         20         30         40         50         60
  gacatacagctagaaagctgtattgcctttagcactcaagctcaaaagACAACTCAGAGT  ← OVATg1
           70         80         90        100        110        120
  TCACCATgggctccatcggcgcagcaagcatggaattttgttttgatgtattcaaggagc
         M   G   S   I   G   A   A   S   M   E   F   C   F   D   V   F   K   E 10         20         30         40         50         60
  gacatacagctagaaagctgtattgcctttagcactcaagctcaaaagacaactcagAGT  ← OVATg2
           70         80         90        100        110        120
  TCACCATGGGCTCCATcggcgcagcaagcatggaattttgttttgatgtattcaaggagc
         M   G   S   I   G   A   A   S   M   E   F   C   F   D   V   F   K   E
```

[Fig. 6B]

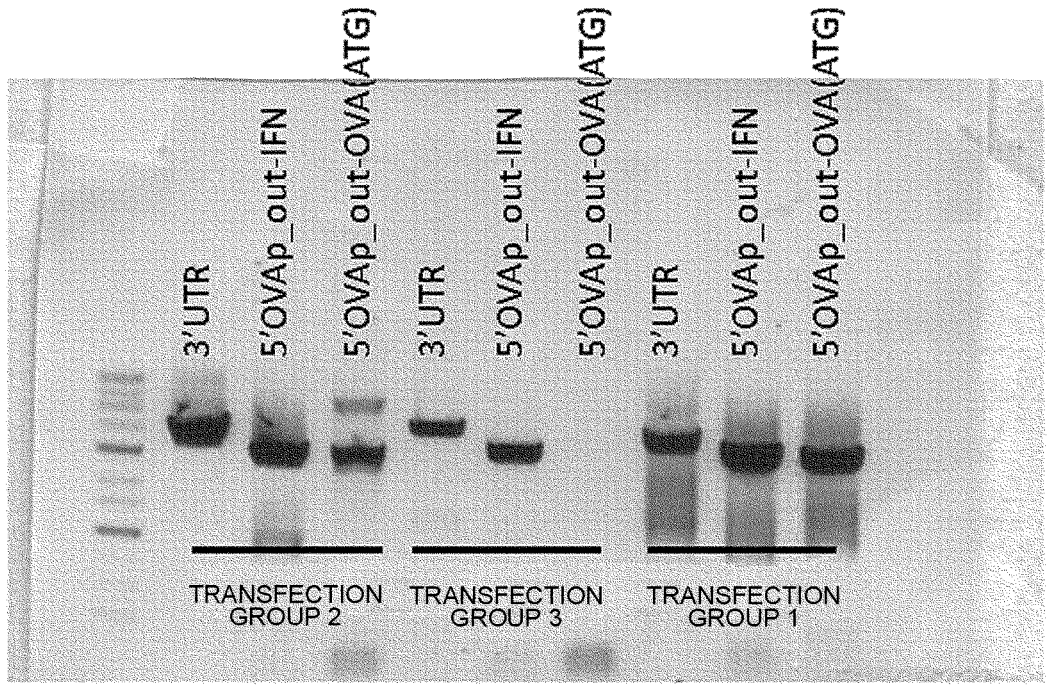

[Fig. 7]
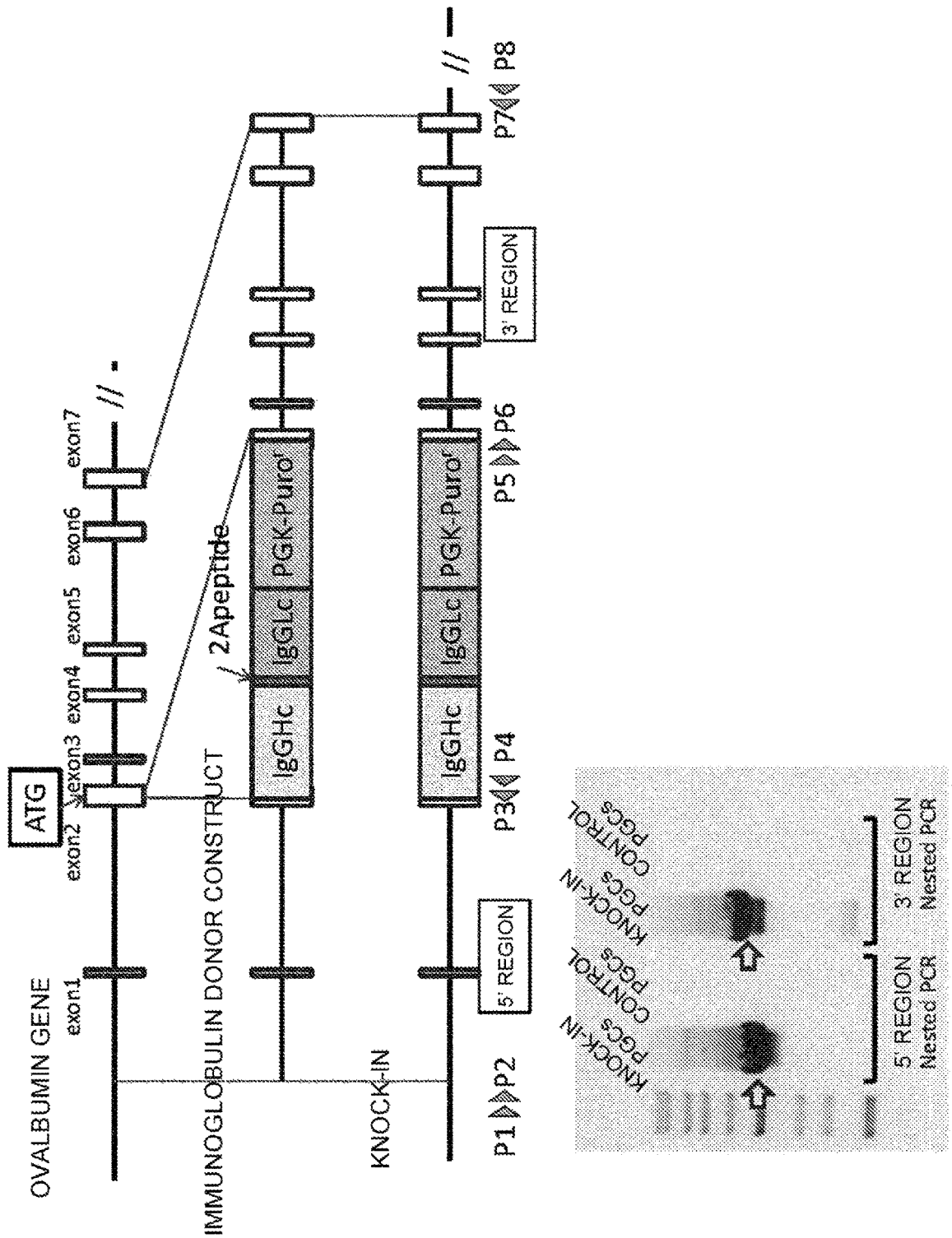

[Fig. 8]
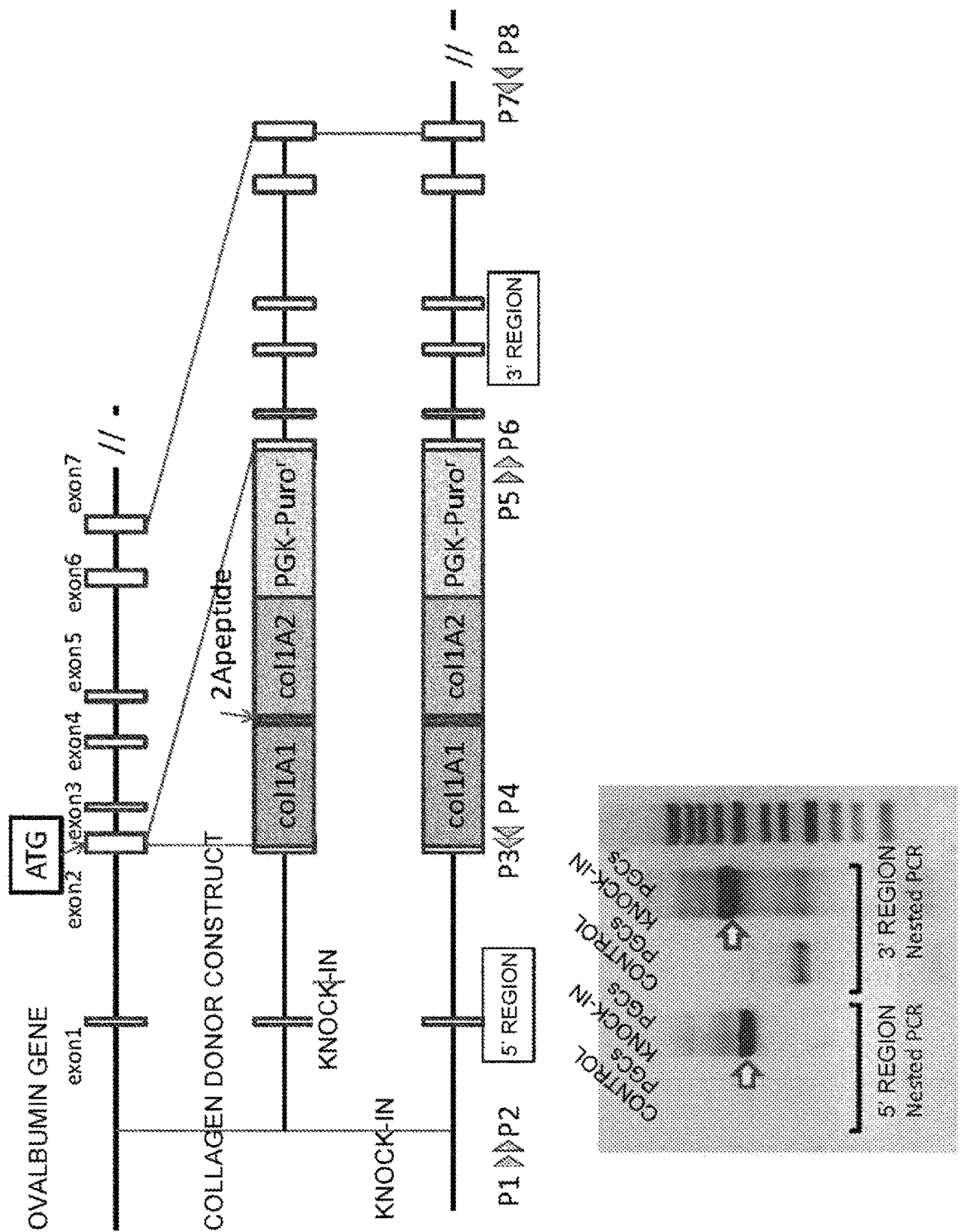

[Fig. 9]
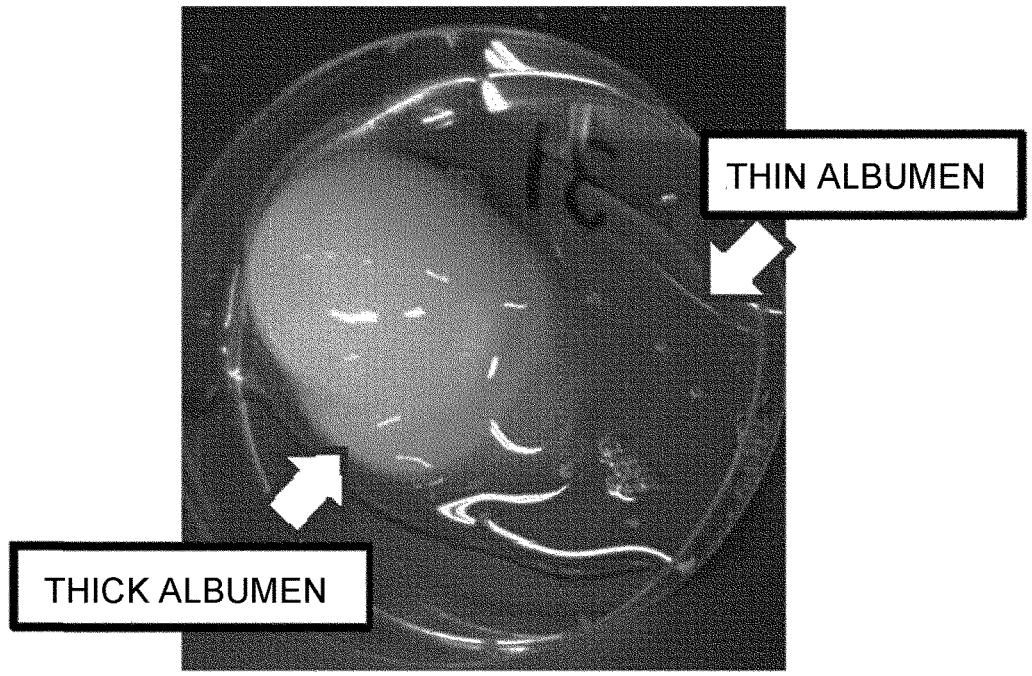
[Fig. 10]
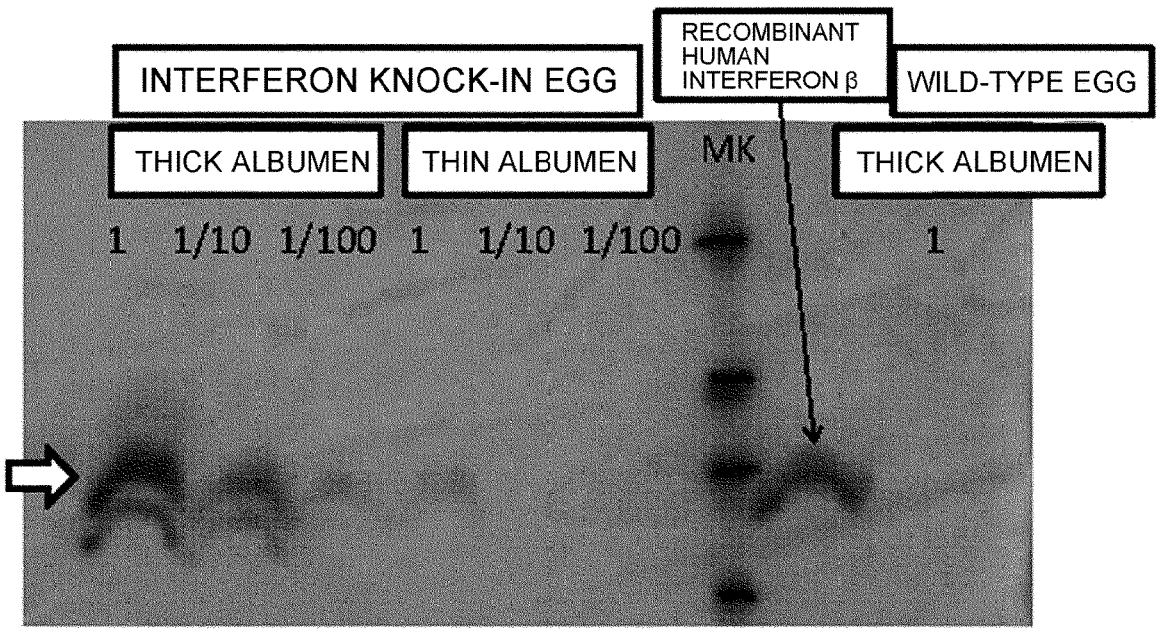

[Fig. 11]
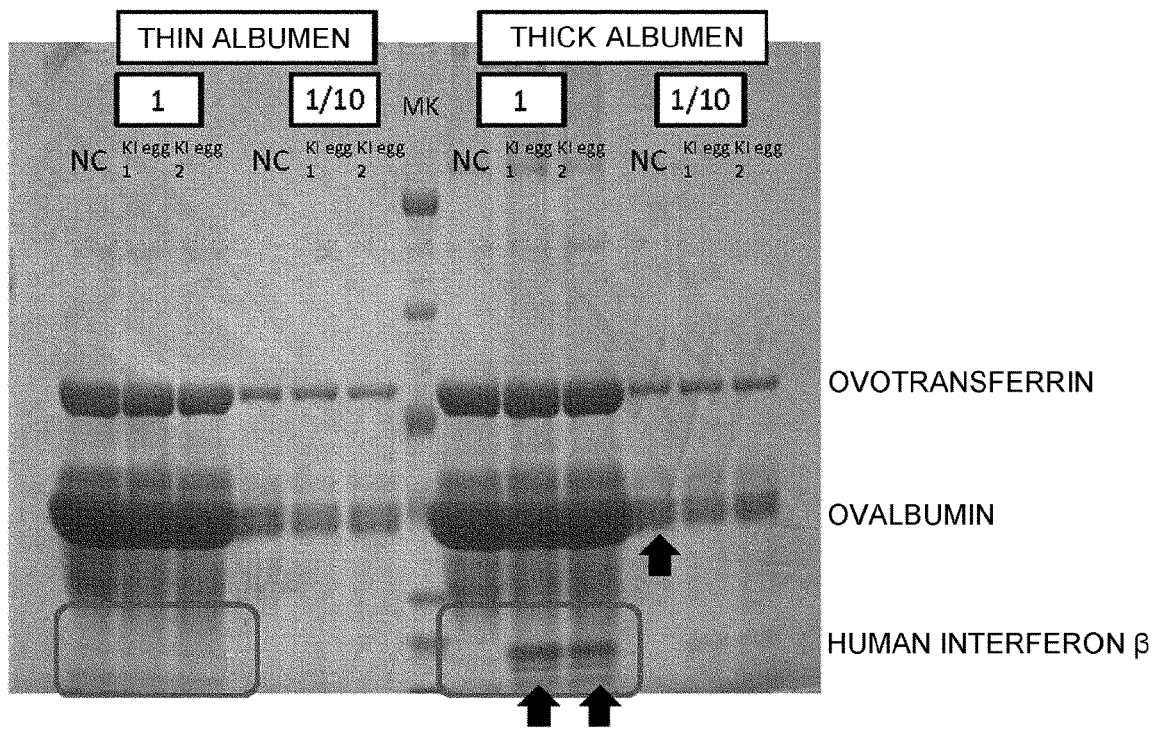
[Fig. 12]
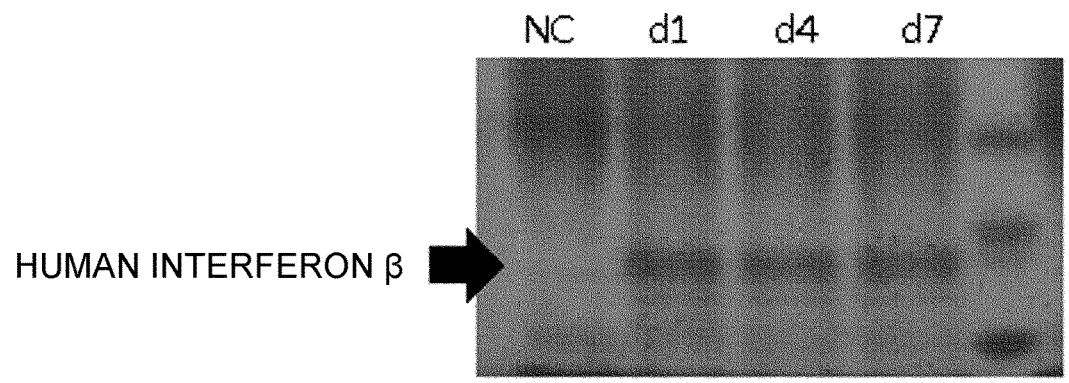
[Fig. 13]
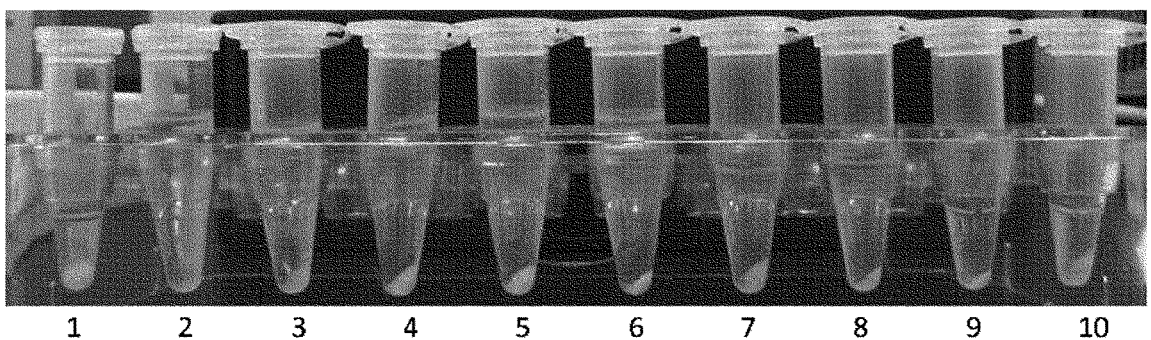

[Fig. 14]
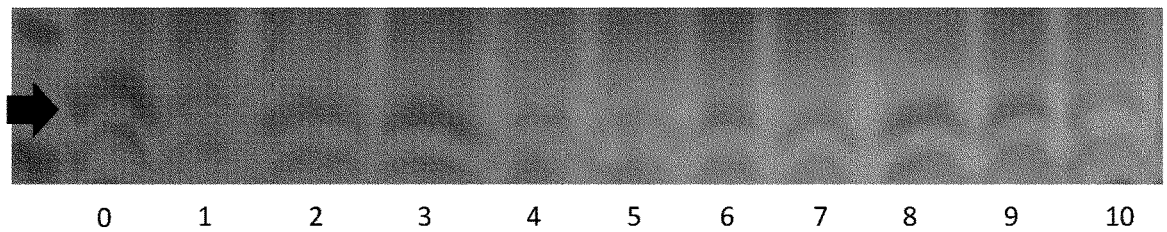
0  1  2  3  4  5  6  7  8  9  10
[Fig. 15]
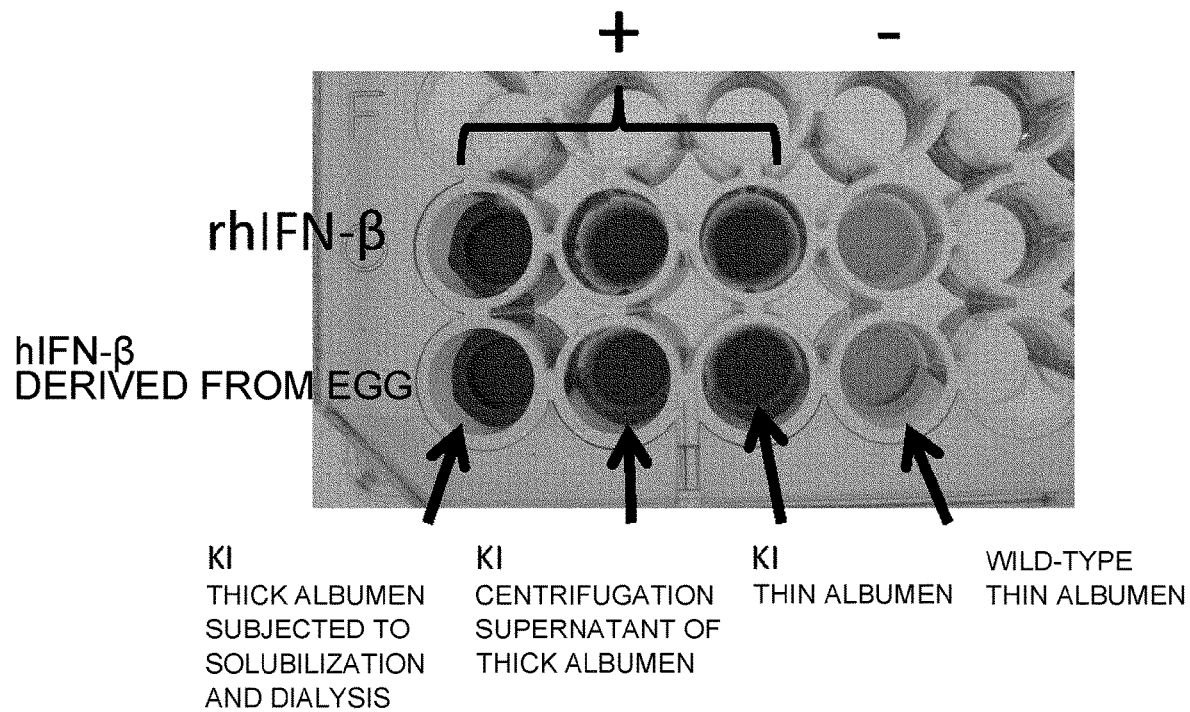

[Fig. 16]
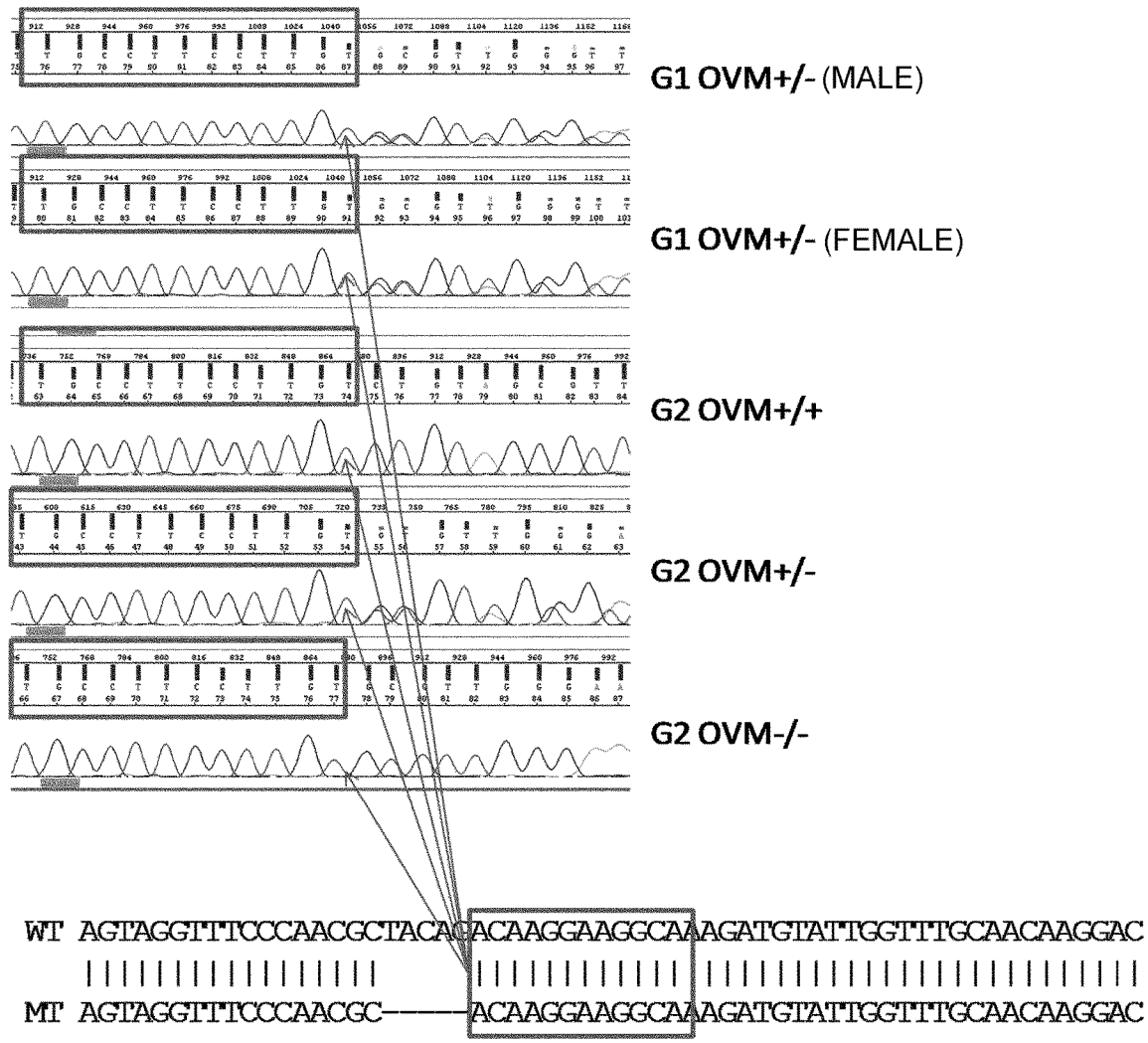

[Fig. 17]
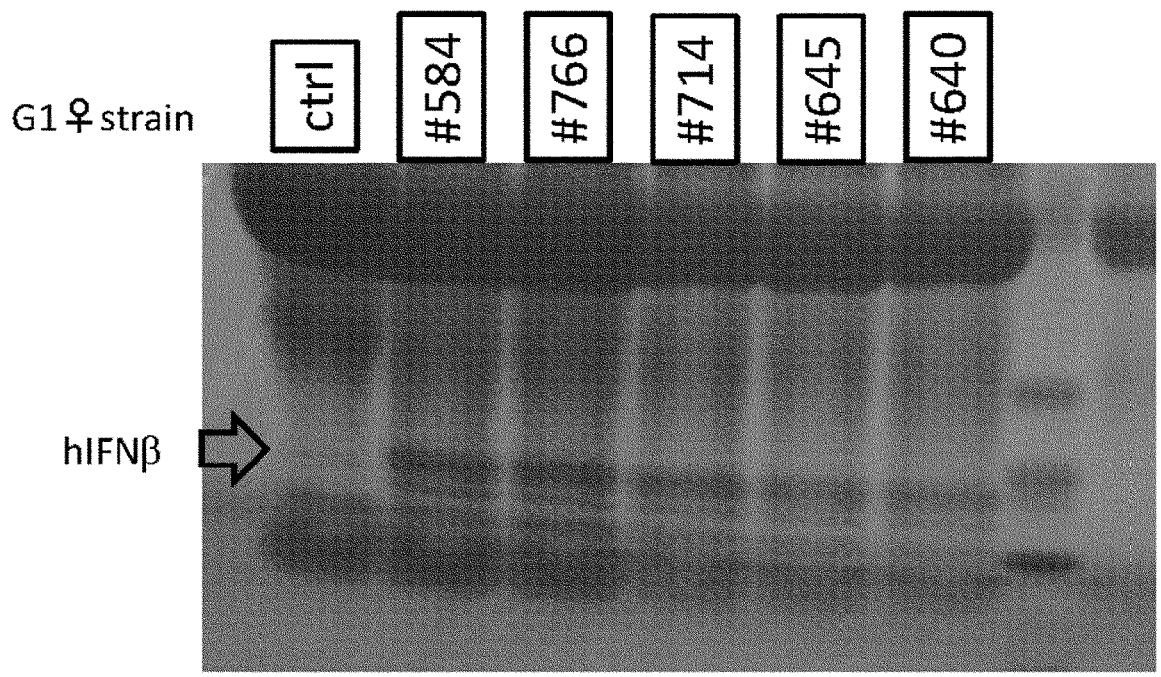

[Fig. 18]
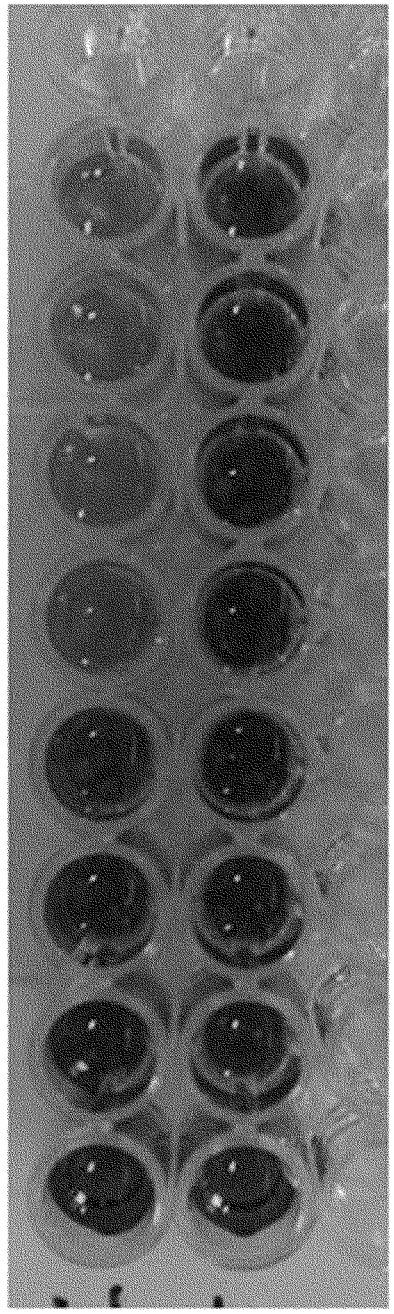

[Fig. 19]
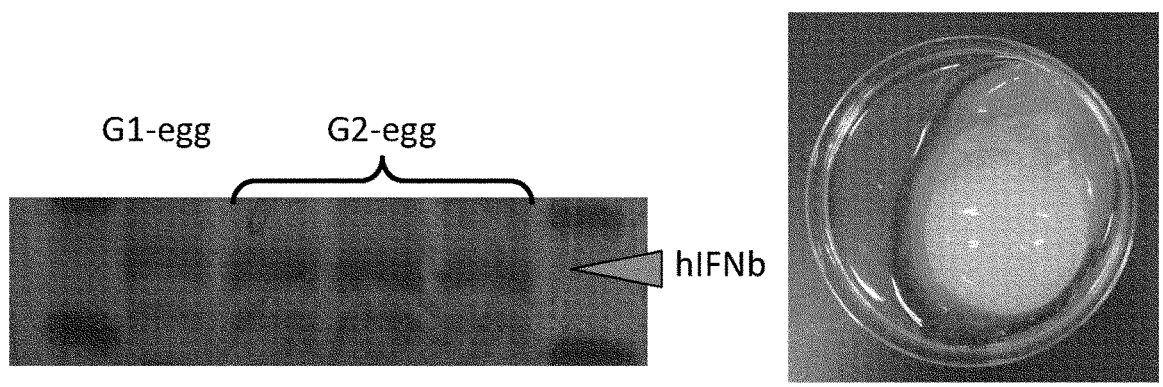

[Fig. 20]
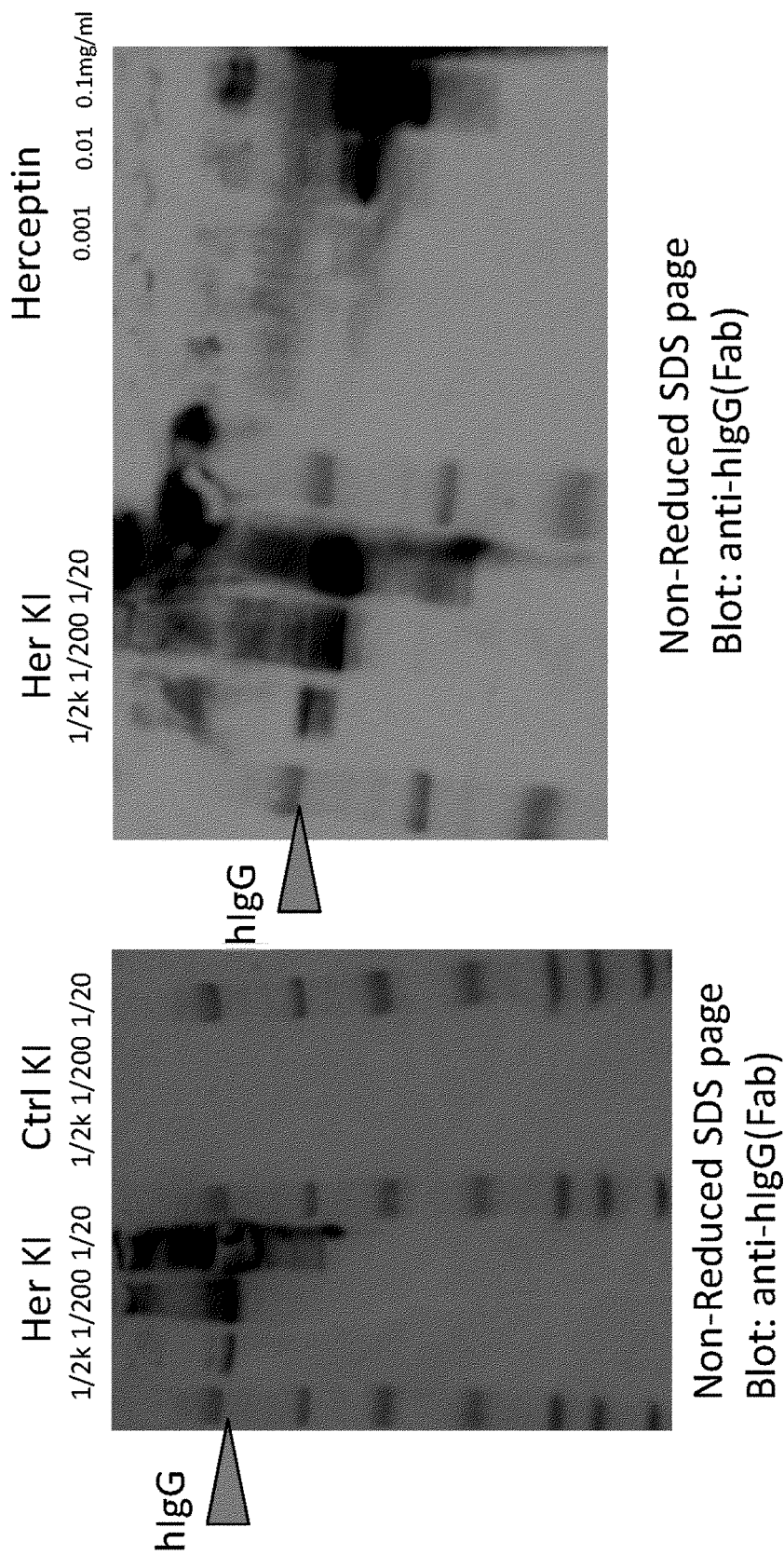

[Fig. 21]
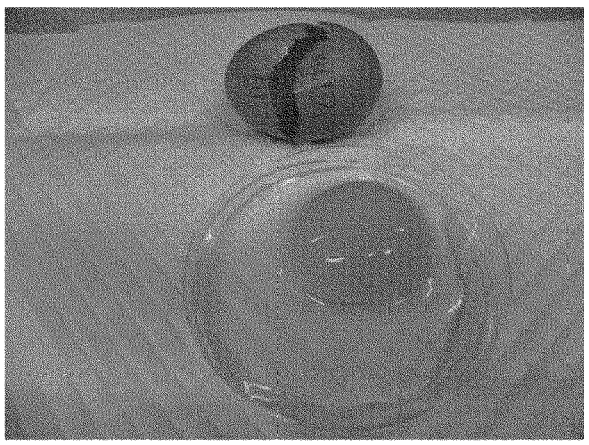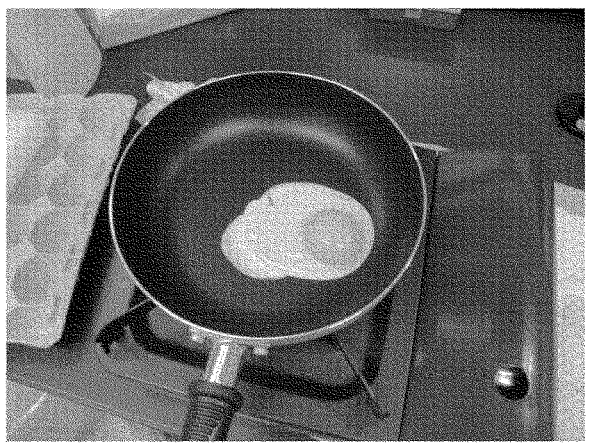

[Fig. 22]
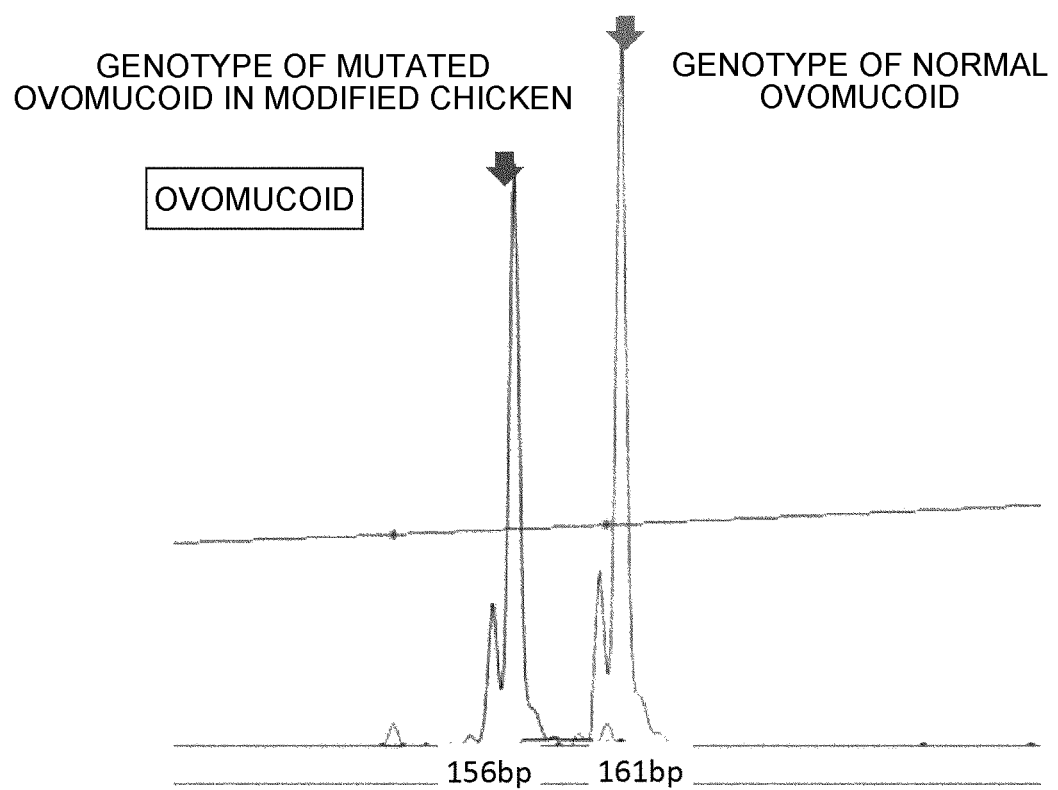

[Fig. 23]
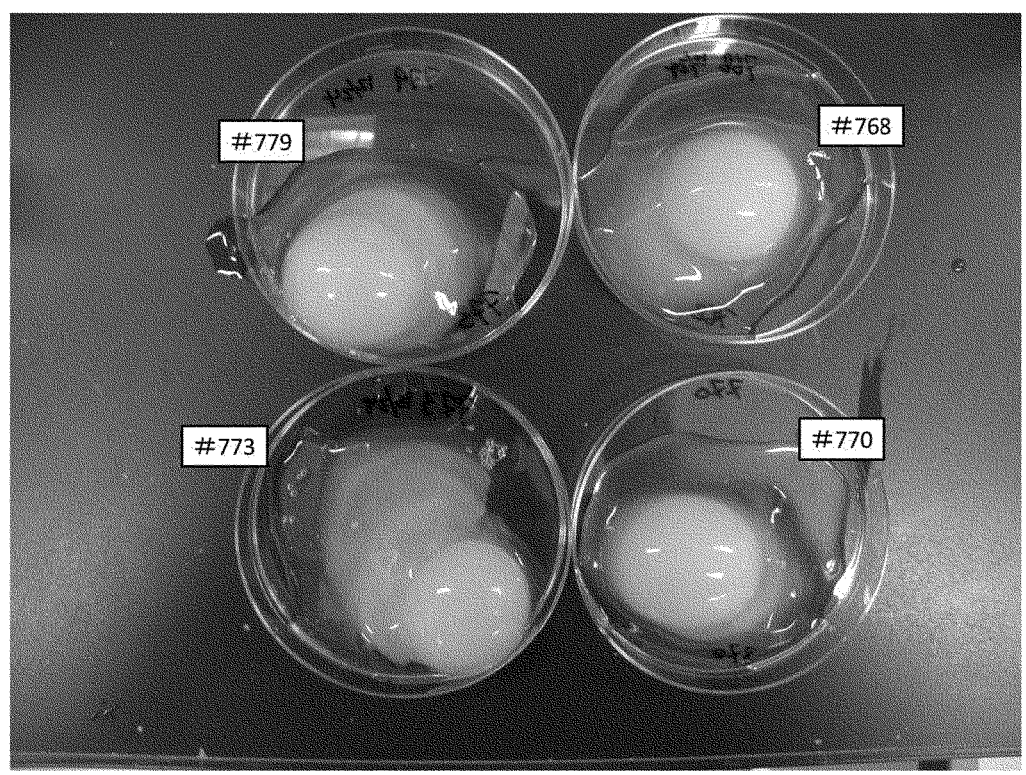

GENETICALLY MODIFIED CHICKEN EGG WITH AN EXOGENOUS SEQUENCE KNOCKED INTO THE OVALBUMIN GENE

TECHNICAL FIELD

The present invention relates to an egg of knock-out poultry and an individual derived therefrom, and an egg and a thick albumen of knock-in poultry.

Further, the present invention relates to a method of preparing an expression product of an exogenous gene.

BACKGROUND

It has been attempted to induce the expression of human interferon β in an egg using a promoter containing a 2.8 kbp upstream region of a translation starting site of ovalbumin, or a promoter to which a further upstream estrogen-responsive enhancer element is attached to the 2.8 kbp region (Non-Patent Literature 1). In this example, a gene transfection is carried out using a lentiviral vector instead of using a knock-in method, so that a vector gene is inserted in a various location in the genome, and several vector genes are inserted. Consistent with such a gene transfection form, a concentration of human interferon β secreted in the egg significantly varies, and an average concentration in 6 chickens is 3.5 to 426 μg/ml. Further, data show that the concentration significantly varies among eggs derived from the same individual, indicating that the expression of interferon β is very unstable. Further, because the genes inserted in various locations of chromosomes are subjected to a gene silencing effect or the like, in general offspring (G2) of G1 chickens expressing interferon β at a relatively high level tend to reduce the expression level of interferon β.

In Non-Patent Literature 2, transgenic chimeric chickens (G0) expressing a Fv-Fc protein in the whole body are created using an actin promoter causing an expression in the whole body and a retroviral vector. It was confirmed that some G0 chickens express the Fv-Fc protein at a high concentration of 5 mg/ml. However, because the gene transfection is performed by viral infection in a chicken embryo, the gene transfection is achieved in a mosaic manner in which the presence/absence of gene insertion, the copy number of insertion, and a location of insertion differ between cells in the same individual. As a result, the G0 chimeric individual expressing the protein at a high concentration produces offsprings of transgenic individuals having the inserted genes varied in numbers and positions, making it difficult to completely transmit the character of the G0 chimeric individual to the offsprings. In fact, the expression level is reduced to 2 mg/ml or less in the G1 generation and 0.8 mg/ml or less in the G2 generation. Further, in many cases, an exogenous gene is not introduced in germline cells of the chimeric chicken infected by viruses. Thus, although one or several chickens that express the protein at a high level can be occasionally obtained in the G0 generation, it is difficult to propagate individuals having the same character and genetic information from such chickens. Such non-uniformity among G0 individuals or between G0 and G1 generations causes a fatal disadvantage for building so-called an "animal factory" in which a large number of chickens expressing an exogenous protein are grown to obtain a large number of eggs for mass production of the proteins.

Non-Patent Literature 4 shows an example in which an oviduct-specific gene, ovalbumin, is disrupted using a TALEN method. However, this literature only shows that a chick having a heterozygous deletion (+/−) in ovalbumin is obtained, and it is difficult to predict whether such poultry can produce an egg in the future, whether an egg having a null (−/−) genotype or an individual derived therefrom can be obtained, whether a homozygous knockout female (−/−) produces an egg, or whether an individual can hatch from an egg lacking the ovalbumin protein.

CITATION LIST

Non-Patent Literature

Non-Patent Literature 1: Lillico, S. G. et al. Oviduct-specific expression of two therapeutic proteins in transgenic hens. Proc Natl Acad Sci USA 104, 1771-1776 (2007)

Non-Patent Literature 2: Kamihira et al. High-Level Expression of Single-Chain Fv-Fc Fusion Protein in Serum and Egg White of Genetically Manipulated Chickens by Using a Retroviral Vector. Journal of Virology, p. 10864-10874 (2005)

Non-Patent Literature 3: van de Lavoir M C, Diamond J H, Leighton P A, Mather-Love C, Heyer B S, Bradshaw R, Kerchner A, Hooi L T, Gessaro T M, Swanberg S E et al: Germline transmission of genetically modified primordial germ cells. Nature 2006, 441(7094): 766-769

Non-Patent Literature 4: Park, T. S., Lee, H. J., Kim, K. H., Kim, J. S. & Han, J. Y. Targeted gene knockout in chickens mediated by TALENs. Proc Natl Acad Sci USA. 111, 12716-12721 (2014)

SUMMARY

Technical Problem

An object of the present invention is to provide a poultry egg in which an expression level of a protein encoded by an oviduct-specific gene is reduced or eliminated.

Further, another object of the present invention is to provide a poultry egg in which an exogenous gene is stably expressed, and a gene product thereof is highly expressed.

Further, another object of the present invention is to provide a technique for efficiently recovering an exogenous gene product, which is expressed in a chicken egg using a knock-in technique.

Solution to Problem

The present invention provides the following knock-out poultry egg and knock-in poultry egg. Further, the present invention provides a method of efficiently preparing an exogenous gene product from the knock-in poultry egg.

The present invention, in one aspect, relates to:

[1] a knock-out poultry egg in which at least one oviduct-specific gene is knocked out, the gene being selected from the group consisting of ovalbumin, ovomucoid, ovomucin, ovotransferrin, ovoinhibitor, and lysozyme, and at least one egg allergen protein is reduced or eliminated, the protein being selected from the group consisting of ovalbumin, ovomucoid, ovomucin, ovotransferrin, ovoinhibitor, and lysozyme.

Further, in one embodiment of the present invention,

[2] the knock-out poultry egg according to the item [1] above is characterized in that a base sequence encoding the knocked-out oviduct-specific gene includes deletion, substitution, or insertion of a base or bases in a region near a 5' side or 3' side of a PAM sequence.

Further, in one embodiment of the present invention, [3] the knock-out poultry egg according to the item [1] or [2] above is characterized in that the oviduct-specific gene is homozygously knocked-out and a genotype of the oviduct-specific gene is null (−/−).

Further, in one embodiment of the present invention, [4] the knock-out poultry egg according to any of the items [1] to [3] above is characterized in that the oviduct-specific gene is ovalbumin.

Further, in one embodiment of the present invention, [5] the knock-out poultry egg according to the item [4] above is characterized in that a base sequence encoding ovalbumin includes deletion, substitution, or insertion of a base or bases in a region corresponding to a base sequence represented by SEQ ID NO: 1 (OVATg1) and a vicinity thereof.

Further, in one embodiment of the present invention, [6] the knock-out poultry egg according to any of the items [1] to [3] above is characterized in that the oviduct-specific gene is an ovomucoid gene.

Further, in one embodiment of the present invention, [7] the knock-out poultry egg according to the item [6] above is characterized in that a base sequence encoding ovomucoid includes deletion, substitution, or insertion of a base or bases in a region corresponding to a base sequence represented by SEQ ID NO: 6 (OVMTg2) and a vicinity thereof.

Further, in one embodiment of the present invention, [8] the knock-out poultry egg according to the item [6] or [7] above is characterized by being substantially free of endogenous ovomucoid.

Further, the present invention, in another aspect, relates to:
[9] a knock-out poultry derived from the knock-out poultry egg according to any of the items [1] to [8] above.

Further, the present invention, in another aspect, relates to:
[10] a knock-in poultry egg, in which:
an exogenous gene under control of an oviduct-specific gene promoter is knocked-in as homozygous or heterozygous and an expression product of the exogenous gene is stably and highly expressed in an egg; and
the oviduct-specific gene promoter is at least one of promoters of oviduct-specific genes selected from the group consisting of ovalbumin, ovomucoid, ovomucin, ovotransferrin, ovoinhibitor, and lysozyme.

Further, in one embodiment of the present invention, [11] the knock-in poultry egg according to the item [10] above is characterized in that the oviduct-specific gene promoter is an ovalbumin gene promoter, and the exogenous gene and a drug-resistant gene are both inserted in an exon 2 of an ovalbumin gene.

Further, in one embodiment of the present invention, [12] the knock-in poultry egg according to the item [10] or [11] above is characterized in that the exogenous gene is inserted in a region corresponding to a base sequence represented by SEQ ID NO: 1 (OVATg1) or a vicinity thereof or a region corresponding to a base sequence represented by SEQ ID NO: 24 (OVATg2) or a vicinity thereof in a base sequence encoding ovalbumin.

Further, in one embodiment of the present invention, [13] the knock-in poultry egg according to any of the items [10] to [12] above is characterized in that a protein encoded by the exogenous gene is contained in an amount of 1 mg or more per egg.

Further, in one embodiment of the present invention, [14] the knock-in poultry egg according to any of the items [10] to [13] above is characterized in that an expression product of the exogenous gene is dominantly expressed in a thick albumen.

Further, in one embodiment of the present invention, [15] the knock-in poultry egg according to any of the items [10] to [14] above is characterized in that the exogenous gene is a gene encoding interferon β, immunoglobulin, or collagen.

Further, in one embodiment of the present invention, [16] the knock-in poultry egg according to any of the items [10] to [15] above is characterized in that the exogenous gene is a gene derived from a human being.

Further, the present invention, in another aspect, relates to:
[17] a thick albumen derived from a knock-in poultry egg in which an exogenous gene under control of an ovalbumin gene promoter is knocked-in homozygously or heterozygously, the thick albumen dominantly containing an expression product of the exogenous gene that is stably and highly expressed.

Further, the present invention, in another aspect, relates to:
[18] a method of producing a knock-in poultry egg containing an expression product of an exogenous gene that is stably and highly expressed, the method comprising:
a step (a) of knocking-in the exogenous gene under control of an oviduct-specific gene promoter in a poultry primordial germ cell;
a step (b) of producing female poultry in which the exogenous gene under control of the oviduct-specific gene promoter is knocked-in as homozygous or heterozygous using the poultry germ cell; and
a step (c) obtaining a poultry egg expressing the exogenous gene from the female poultry.

Further, in one embodiment of the present invention, [19] the method of producing the knock-in poultry egg containing the expression product of the exogenous gene that is stably and highly expressed according to the item [18] above is characterized in that the step (a) is a step of introducing the exogenous gene by genome editing using (i) a donor construct that includes a 5' side region of a translation starting site under control of the oviduct-specific gene promoter, the exogenous gene, a drug-resistant gene unit, and a 3' side region of the translation starting site, and (ii) a vector that includes a target sequence and a different drug-resistant gene unit.

Further, in one embodiment of the present invention, [20] the method of producing the knock-in poultry egg containing the expression product of the exogenous gene that is stably and highly expressed according to the item [19] above is characterized in that:
the oviduct-specific gene promoter in the step (a) is an ovalbumin gene promoter.

Further, in one embodiment of the present invention, [21] the method of producing the knock-in poultry egg containing the expression product of the exogenous gene that is stably and highly expressed according to the item [19] or [20] above is characterized in that the step (a) is a step of introducing the exogenous gene by CRISPR using (i) a donor construct that includes a 2.8 kb 5' side region of a translation starting site of ovalbumin, the exogenous gene, a neomycin-resistant gene unit, and a 3.0 kb 3' side region of the translation starting site of ovalbumin, and (ii) a vector that includes a base sequence represented by SEQ ID NO: 24 as the target sequence and a neomycin-resistant gene unit.

Further, the present invention, in another aspect, relates to:

[22] a method of preparing an expression product of an exogenous gene from a knock-in poultry egg, further comprising a step (d) of recovering the expression product of the exogenous gene from the poultry egg after the step (c) in the method according to any of items [18] to [21] above.

Effects of Invention

The knock-in poultry egg of the present invention is produced from a knock-in poultry individual in which an identical exogenous gene (a gene not derived from the poultry) is inserted in an identical location in the whole body, thus the difference in a protein expression level between individuals is small and genetic information and character of the exogenous gene can be properly transmitted over generations. Further, the expression of the exogenous gene can be restricted to an oviduct by performing gene knock-in at a location of the oviduct-specific gene. In this manner, a possibility of affecting a development process and the health of chicken is clearly lower as compared to a case where the exogenous gene is expressed in the whole body, which produces excellent effects. In addition, it is further preferable that the exogenous gene is expressed under control of a gene that is highly expressing in the albumen, such as ovomucoid, to increase an expression efficiency of the exogenous gene. Moreover, the knock-in chicken can be efficiently established by the gene knock-in using genome editing. It is confirmed that using such a new technique also allows the expression of the exogenous gene in the oviduct and the accumulation of the exogenous gene expression product in the albumen. Further, it is found, for the first time, that the exogenous gene-derived product mainly localizes to the thick albumen in the albumen. Based on this observation, the exogenous gene-derived product can be efficiently recovered by recovering a portion including the thick albumen from the egg containing the exogenous gene product, in a preferred embodiment, from the egg in which the exogenous gene is knocked-in at an albumen gene locus.

Because the oviduct-specific gene is knocked-out in the knock-out poultry egg of the present invention, the impact on the development is a matter of concern. However, it is confirmed by the inventor that such knock-out poultry can produce an egg.

BRIEF DESCRIPTION OF DRAWINGS

FIG. 1 shows a target sequence of a chicken ovalbumin gene (a target sequence of OVATg1). An sgRNA recognition site is indicated in capitals and a PAM sequence is indicated by an adjacent underline.

FIG. 2 shows a target sequence of a chicken ovomucoid gene (a target sequence of OVMTg2). An sgRNA recognition site is indicated in capitals and a PAM sequence is indicated by an adjacent underline.

FIG. 3 shows an example of disruption of the ovalbumin gene by CRISPR. An sgRNA recognition site is indicated in capitals (underlined) and a PAM sequence is indicated by an adjacent box. A deletion site of mutated sequence is indicated by a hyphen (-) and mutated sites are indicated in capitals. A translation starting site of OVATg1 is indicated by Met.

FIG. 4A shows an example of disruption of the ovomucoid gene by CRISPR. An sgRNA recognition site is indicated in capitals (underlined) and a PAM sequence is indicated by an adjacent box.

FIG. 4B (upper panel): An example of a chicken in which the ovomucoid gene is disrupted. A chicken (black) in a photograph is derived from a transplanted primordial germ cell and one allele of the ovomucoid gene has a 5-base deletion in a Tg2 region shown in FIG. 2. A base sequence of the Tg2 region in the chicken genome is analyzed both on a sense side and an antisense side. (lower panel): An example of ovomucoid gene mutations found in chicken individuals (F1 chickens). Deletions of 1 to 31 bases are found.

FIG. 5A shows knock-in of a human interferon β gene at an ovalbumin gene locus and demonstration of the knock-in by genome PCR. Primer 1 (P1) to primer 8 (P8) correspond to the following sequences. P1: SEQ ID NO: 15, P2: SEQ ID NO: 17, P3: SEQ ID NO: 16, P4: SEQ ID NO: 14, P5: SEQ ID NO: 18, P6: SEQ ID NO: 20, P7: SEQ ID NO: 21, P8: SEQ ID NO: 19. As a result of nested PCR, amplification products in predicted sizes are detected only in genome derived from the knock-in primordial germ cells (PGCs) (indicated by arrows in an image).

FIG. 5B shows knock-in of the human interferon β gene at the ovalbumin gene locus in a chimeric chicken sperm. Semen genomes from 4 chimeric chickens (411 to 414) and 1 negative control chicken (416, NC), and genome of knock-in cells (PCIFNKI #4) are amplified using primer sets of SEQ ID NO: 18 and 19 (3' UTR), SEQ ID NO: 15 and 14 (5' OVAp_out-IFN), and SEQ ID NO: 15 and 22 (5' OVAp_out-OVA(ATG)). Detected bands in predicted sizes are indicated by "*". In 411 and 412, knock-in signals having almost the same relative intensities as that of the positive control are detected.

FIG. 5C shows chickens in which the human interferon β gene is knocked-in at the ovalbumin gene locus. Photographs show chickens (female) which are offsprings of 411 and 412 in FIG. 5B. A PCR analysis of genomes derived from blood of the offsprings demonstrates that an IFN donor construct is knocked-in at the ovalbumin gene locus. A genome derived from blood of a wild-type (WT: a negative control) chicken, the genomes derived from blood of the knock-in chicken offsprings (KI), and a genome derived from a knock-in cell (KI PGC: a positive control) are amplified using primer sets of SEQ ID NO: 18 and 19 (a knock-in 3' region), SEQ ID NO: 15 and 14 (a knock-in 5' region), and SEQ ID NO: 15 and 22 (endogenous ovalbumin). Detected bands in predicted sizes are indicated by "*". In the offsprings of 411 and 412, signals having the same patterns as that of the positive control are detected, indicating that the IFN donor construct is knocked-in at the ovalbumin gene locus in the chicken offsprings.

FIG. 6A shows target sequences (2 locations, the target sequences of OVATg1 and OVATg2) of the chicken ovalbumin gene. sgRNA recognition sites are indicated in capitals and PAM sequences are indicated by adjacent underlines.

FIG. 6B shows an efficiency of gene knock-in at the ovalbumin gene locus of the chicken primordial germ cell. The knock-in efficiency is the same between a transfection group 1 and a transfection group 2. Since the transfection group 2 has more cells, a transfection method of the transfection group 2 is more preferable. The knock-in efficiency seems to be higher in a transfection group 3 than that in the transfection group 2, thus a transfection method of the transfection group 3 is more preferable.

FIG. 7 shows knock-in of a human immunoglobulin gene at the ovalbumin gene locus and demonstration of the knock-in by genome PCR. Primer 1 (P1) to primer 8 (P8) correspond to the following sequences. P1: SEQ ID NO: 15, P2: SEQ ID NO: 17, P3: SEQ ID NO: 29, P4: SEQ ID NO: 28, P5: SEQ ID NO: 18, P6: SEQ ID NO: 20, P7: SEQ ID NO: 21, P8: SEQ ID NO: 19. As a result of nested PCR, amplification products in predicted sizes are detected only in the genome derived from the knock-in primordial germ cells (PGCs) (indicated by arrows in an image).

FIG. 8 shows knock-in of a human collagen gene at the ovalbumin gene locus and demonstration of the knock-in by genome PCR. Primer 1 (P1) to primer 8 (P8) correspond to the following sequences. P1: SEQ ID NO: 15, P2: SEQ ID NO: 17, P3: SEQ ID NO: 29, P4: SEQ ID NO: 28, P5: SEQ ID NO: 18, P6: SEQ ID NO: 20, P7: SEQ ID NO: 21, P8: SEQ ID NO: 31. As a result of nested PCR, amplification products in predicted sizes are detected only in the genome derived from the knock-in primordial germ cells (PGCs) (indicated by arrows in an image).

FIG. 9 shows an image of an egg produced from an interferon β knock-in female chicken. It is found that a thick albumen surrounding an egg yolk is cloudy.

FIG. 10 shows an image of western blotting of albumen components using an anti-human interferon β antibody. Recombinant human interferon β (indicated by an arrow) is expressed in an egg derived from a knock-in chicken. A thick albumen contains more human interferon β proteins than a thin albumen per unit volume. It is found that the thick albumen contains 100 times more human interferon β proteins than the thin albumen in terms of a relative concentration.

FIG. 11 shows a distribution of human interferon β in the albumen produced by the human interferon β knock-in chicken. In eggs derived from multiple chickens (KI egg 1 and 2), the thick albumen contains more interferon β proteins than the thin albumen (indicated by boxes). A concentration of recombinant human interferon β in the thick albumen is one tenth of the ovalbumin proteins present in a concentration of about 50 mg/ml (indicated by black arrows), thus the concentration of recombinant human interferon β is estimated to be about 5 mg/ml.

FIG. 12 shows how stably the interferon β protein is expressed in an egg produced from the interferon β knock-in chicken. Eggs were collected for a week (d1 to d7) and human interferon β contained in the thick albumen was identified by CBB staining. It is found that interferon β is stably expressed during the test period.

FIG. 13 shows an image of white precipitates obtained after centrifugation of the thick albumen. The thick albumen of the egg produced from the interferon β knock-in chicken is centrifuged without any treatment (1) or after various treatments (2 to 10) to compare amounts of white precipitate. The amounts of the white precipitates are reduced in 2 to 10 as compared to 1. In FIG. 13, a thick albumen liquid in an amount of 200 µl is added in each tube and subjected to the following treatments. The thick albumen liquid is added and mixed by inversion with 4 times volume (800 µl) of a 3M saturated arginine solution (tube 2), added with 4 times volume (800 µl) of the 3M saturated arginine solution and subjected to ultrasonic crushing (tube 3), added and mixed by inversion with a small amount of arginine (20 mg) and filled up with PBS to 1 ml (tube 4), added and mixed by inversion with a small amount of arginine hydrochloride (20 mg) and filled up with PBS to 1 ml (tube 5), filled up with PBS to 1 ml and subjected to the ultrasonic crushing (tube 6), added and mixed by inversion with arginine hydrochloride in a saturating amount or more (200 mg) (tube 7), added with twice volume (400 µl) of the 3M saturated arginine solution and subjected to the ultrasonic crushing (tube 8), added with a small amount of arginine hydrochloride (20 mg) and subjected to the ultrasonic crushing (tube 9), or added with a small amount of sodium chloride (40 mg) and subjected to the ultrasonic crushing (tube 10). Although the white precipitates were still observed after centrifugation at 20 k×g for 15 minutes, the amounts of the white precipitates were reduced by all of these treatments as compared to the case where no treatment was performed (tube 1). In particular, the amounts of the white precipitates were markedly reduced in the tubes 3, 6, 8, and 9, which were subjected to the ultrasonic crushing.

FIG. 14 shows an image of electrophoresis of supernatants of the thick albumen after various treatments. The thick albumen without the centrifugation treatment (lane 0) and the supernatants of the tubes 1 to 10 in FIG. 13 (lanes 1 to 10) were subjected to electrophoresis after adjusting their loading amounts to be equal on the basis of the original amounts of the thick albumen. Bands of human interferon β are indicated by a black arrow.

FIG. 15 shows activity of human interferon β contained in an egg derived from the human interferon β knock-in chicken. The activity of human interferon β is detected in all of a thick albumen rough purification product, a centrifugation supernatant of the thick albumen, and the thin albumen.

FIG. 16 shows genomes of ovomucoid heterozygous knock-out (in a G1 generation: 5-base deletion in ORF) male and female, and genomes of ovomucoid heterozygous and homozygous knock-out and wild-type chickens obtained from the heterozygous knock-out chickens in the next generation.

FIG. 17 shows an image of electrophoresis of the thick albumen obtained from different G1 individuals. The thick albumen derived from a wild-type chicken (ctrl) and the thick albumen derived from 5 human interferon β knock-in chickens (#584, #766, #714, #645, and #640) are subjected to electrophoresis. Bands of human interferon β are indicated by an arrow.

FIG. 18 shows a comparison of activity between human interferon β contained in the egg derived from the human interferon β knock-in chicken (lower stage) and commercially available recombinant human interferon β (upper stage). In the image, culture supernatants of bioassay cells are added to a QUANTI-Blue substrate solution. The albumen supernatant and commercially available interferon β are serially diluted by 5-fold and added to the bioassay cells. Judging from a color change of the substrate solution, the albumen supernatant contains interferon β at a concentration of 625 or more times greater than a 0.01 µg/µl concentration of commercially available interferon β.

FIG. 19 shows the interferon β proteins (left panel) in the eggs derived from the human interferon β knock-in chickens in the G1 generation and G2 generation. Concentrations of human interferon β in the thick albumen of the eggs derived from G1 and G2 (3 female chickens) are approximately equal to each other. Further, the egg derived from G2 is cloudy as is the case for the egg derived from G1.

FIG. 20 shows an image of western blotting of the albumen derived from a chicken in which a human antibody gene is knocked-in at the ovalbumin gene locus using an anti-human immunoglobulin antibody. A recombinant human antibody (indicated by an arrow with a sign of hIgG) is expressed in an egg derived from the knock-in chicken (hIgG KI) but not in the albumen derived from a wild type (ctrl) (left panel). Further, the recombinant human antibody has the same electrophoretic mobility as a commercially available human antibody (Herceptin) under a non-reduced condition, indicating that the recombinant human antibody can form an antibody complex (right panel). A dilution ratio of the albumen is indicated by ½k (½000), ½00, and ½0. Judging from band intensities, a concentration of the antibody complex is 1 mg/ml or more.

FIG. 21 shows an egg derived from an ovomucoid homozygous knock-out (OVM −/− in a G2 generation). The egg is not markedly different from a wild-type egg in appearance (left panel) and the albumen and egg yolk of the egg are coagulated by heating (right panel), thus the egg can be processed similarly to the wild-type egg for cooking or other purposes.

FIG. 22 shows an ovomucoid homozygous knock-out individual in a G3 generation obtained by incubating an egg derived from the ovomucoid homozygous knock-out (OVM −/− in a G2 generation) (upper panel). The G3 generation was obtained by mating an OVM −/− female and OVM −/− male. A chicken can be developed without an endogenous ovomucoid gene or an ovomucoid gene product in the egg. It is found that the ovomucoid gene has a homozygous 5 bp deletion by a fragment analysis (lower panel).

FIG. 23 shows an image of eggs derived from 4 lines of interferon β knock-in female chickens. The thick albumen is cloudy in all 4 eggs as seen in FIG. 9.

DESCRIPTION OF EMBODIMENTS

In the present invention, a gene in a poultry primordial germ cell is modified by genome editing to obtain knock-in or knock-out female poultry that is derived from the genetically modified primordial germ cell, thereby obtaining a knock-in or knock-out poultry egg of the present invention from the knock-in or knock-out female.

In the present specification, the "knock-out poultry egg" includes both eggs produced from female poultry having heterozygous (+/−) genotypes of a knock-out gene and eggs produced from female poultry having homozygous (−/−; null) genotype of the knock-out gene. In a case where a knock-out gene is expressed in an oviduct and encodes an egg allergen accumulated in the albumen, an egg of the heterozygous knock-out poultry has a reduced amount of the egg allergen protein. On the other hand, an egg produced from the homozygous knock-out female poultry lacks the egg allergen protein.

In the present specification, the "knock-in poultry egg" includes both eggs produced from female poultry having heterozygous (+/−) genotype of a knock-in gene and eggs produced from female poultry having homozygous (+/+) genotype of the knock-in gene. An egg produced from the female poultry having the homozygous (+/+) genotype of the knock-in gene contains more expression products of an exogenous gene than an egg produced from the female poultry having the heterozygous (+/−) genotype of the knock-in gene.

The genome editing is a technique for gene modification using a cleavage of double-stranded DNA and an error in repairing the cleavage and includes a nuclease capable of cleaving the target double-stranded DNA and a DNA recognition component that binds to or forms a complex with the nuclease. Examples of the genome editing technique include ZEN (zinc finger nuclease), TALEN, and CRISPR. For example, ZFN uses FokI (a nuclease) and a zinc finger motif (a DNA recognition component), TALEN uses FokI (a nuclease) and a TAL effector (a DNA recognition component), and CRISPR uses Cas9 (a nuclease) and a guide RNA (gRNA, a DNA recognition component). The nuclease used in the genome editing is only required to have nuclease activity, and a DNA polymerase, a recombinase, and the like may be used other than the nuclease.

Examples of the poultry include a chicken, a quail, a turkey, a duck, a goose, a long-tailed cock, a Japanese bantam, a pigeon, an ostrich, a green pheasant, a helmeted guineafowl, and the like. Preferable examples of the poultry include the chicken, the quail, and the like.

The primordial germ cell may be from male or female. The primordial germ cell of the poultry such as a chicken is a floating cell and cultured in the presence of a feeder cell, such as a BRL cell and STO cell. Alternatively, the primordial germ cell may be cultured in the absence of the feeder cell by adding an appropriate cytokine in a medium.

A gene modified by the genome editing is an oviduct-specific gene, and specific examples thereof include ovalbumin, ovomucoid, ovomucin, ovotransferrin, ovoinhibitor, lysozyme, and the like.

A gene function is eliminated by knock-out performed by the gene editing. In a case where at least one base is deleted or inserted in a gene by the gene editing, the gene function may be eliminated by a frame shift. The gene function may be eliminated without a frame shift by missing a part of amino acids. Further, the gene function may be eliminated by generating a stop codon by deletion or substitution.

In a case where an exogenous gene is knocked-in by the genome editing, the exogenous gene is preferably knocked-in at an oviduct-specific gene locus to obtain an egg containing an expression product of the exogenous gene instead of an expression product of the oviduct-specific gene. Examples of a protein as the expression product of the exogenous gene include various secreted proteins and peptides, and specific examples thereof include a functional peptide, such as an antibody (a monoclonal antibody) or a fragment thereof (e.g., scFv, Fab, Fab', F(ab')2, Fv, a single-chain antibody, dsFv, etc.), an enzyme, a hormone, a growth factor, a cytokine, an interferon, a collagen, an extracellular matrix molecule, and a vaccine, an agonistic protein, an antagonistic protein, and the like. In a case where the protein encoded by the exogenous gene is a biologically active protein that can be administered to human as a medicine, such a protein is derived from a mammal, preferably from human. Further, in a case where the protein encoded by the exogenous gene is an industrially applicable protein, such as a protein A and a protein constituting a spider thread, examples of the exogenous gene include a gene that encodes a protein derived from any organisms including a microorganism (bacteria, yeast, etc.), a plant, and an animal, or an artificial protein.

As the exogenous gene, a single gene or a plurality of genes may be used. In a case where a plurality of genes are used, the plurality of genes are expressed under control of the oviduct-specific gene. For example, the plurality of genes may be expressed by interposing a sequence such as IRES between the plurality of genes. Alternatively, the plurality of genes may be expressed by interposing a sequence encoding a 2A peptide or the like between the plurality of genes. In such a case, the plurality of genes are simultaneously expressed as a single peptide under control of an ovalbumin promoter and the peptide is cleaved to produce a plurality of proteins.

The exogenous protein may include an appropriate signal peptide. Codon usage of the exogenous protein may be changed to facilitate its expression in the poultry.

In a preferred embodiment of the knock-in poultry egg of the present invention, the expression product of the exogenous gene is dominantly expressed in the thick albumen. The term "dominant" herein refers to (a) a state in which an expression amount of the exogenous gene in the thick albumen is 50% or more, 60% or more, 65% or more, 70% or more, 75% or more, 80% or more, 85% or more, 90% or more, 95% or more, or 98% or more by mass with respect to an expression amount of the exogenous gene in a whole knock-in egg or (b) a state in which an expression amount of the exogenous gene in the thick albumen is 1.1 times or more, preferably 2 times or more, more preferably 10 times or more of an expression amount of the exogenous gene in an egg other than the thick albumen in a relative concentration. The expression product of the knock-in exogenous gene is concentrated in the thick albumen and can thus be easily purified. Further, the expression product of the exogenous gene can be expressed in an active form. The thick albumen may become cloudy due to the expression product of the exogenous gene. However, a cloudy protein can be easily solubilized by an ultrasonic treatment, adding a solubilizing agent such as arginine hydrochloride, or the like.

In a preferred embodiment of the present invention, the expression product of the knock-in gene expressed in the thick albumen may be in a soluble form or in an insoluble form. The expression product of the knock-in gene in the insoluble form can be purified as an active protein. The expression product of the knock-in gene is preferably purified after solubilized. For purification, a conventional purification method, such as a column and dialysis, may be used. As the genome editing, a zinc finger, TALEN, and CRISPR can be mentioned. Of these, TALEN and CRISPR are preferable and CRISPR is more preferable. As a new genome editing method has been continuously developed, the present invention is not limited to the existing methods and any genome editing methods to be developed in the future may be used in the present invention.

When performing knock-in by the genome editing, it is preferable that a drug-resistant gene is stably integrated in the genome together with the useful exogenous gene to select a knock-in primordial germ cell by the drug-resistant gene. Examples of the drug-resistant gene include a neomycin-resistant gene (Neor), a hydromycin-resistant gene (Hygr), a puromycin-resistant gene (Puror), a blasticidin-resistant gene (blastr), a zeocin-resistant gene (Zeor), and the like. Of these, the neomycin-resistant gene (Neor) or the puromycin-resistant gene (Puror) is preferable.

When performing knock-in of the exogenous gene at the oviduct-specific gene locus, a translation starting site of the exogenous gene is preferably coincided with a translation starting site of the oviduct-specific gene. The exogenous gene may be introduced into the primordial germ cell as single- or double-stranded nucleic acids. The double-stranded nucleic acids may be introduced in a form of a plasmid vector, a BAC (bacterial artificial chromosome) vector, or the like. A gene sequence around the translation starting site of the oviduct-specific gene may be inserted immediately before the translation starting site of the exogenous gene to match the translation starting site of the exogenous gene with the translation starting site of the oviduct-specific gene by the knock-in.

In a case where the ovalbumin gene is selected as the oviduct-specific gene and the exogenous gene is introduced under control of the ovalbumin gene promoter, a 5' end of the exogenous gene is preferably inserted in a base sequence encoding ovalbumin in a region corresponding to a base sequence represented by SEQ ID NO: 1 (OVATg1) or in a region corresponding to a base sequence represented by SEQ ID NO: 24 (OVATg2). More preferably, the translation starting site of the exogenous gene is inserted in the translation starting site of the ovalbumin gene.

In a case where the exogenous gene is knocked-in at the oviduct-specific gene locus to obtain a knock-in chicken individual and its egg, it is desirable that the albumen of the egg is recovered to recover the exogenous gene product. More desirably, a portion including the thick albumen surrounding the egg yolk is recovered to efficiently recover the exogenous gene product.

In a case where a gene function is eliminated by knock-out using the genome editing, the above-mentioned drug-resistant gene is preferably introduced into a primordial germ cell during the gene transfection by the gene editing to perform a selection on the basis of the drug-resistant gene. For the introduction of the drug-resistant gene and drug-based selection, the drug-resistant gene may be stably or transiently introduced. The drug-resistant gene is preferably transiently introduced in the case of the knock-out. Examples of the drug-resistant gene include the ones described above. Of these, the puromycin-resistant gene (Puror) or the zeocin-resistant gene (Zeor) is preferable. The drug-resistant gene may be introduced independently from a zinc finger, TALEN, or CRISPR plasmid or integrated into these plasmids. The drug-resistant gene is preferably integrated into the plasmid used for the genome editing.

In the present invention, performing knock-out of the oviduct-specific gene can induce deletion, substitution, or insertion of a base or bases in a base sequence encoding the oviduct-specific gene to be knocked-out and thus causes a frame shift or a nonsense mutation in the oviduct-specific gene, whereby a protein expression can be eliminated. For example, performing the knock-out by using CRISPR can induce deletion, substitution, or insertion of a base or bases in a region near a 5' side or 3' side of a PAM sequence. The region near the 5' side or 3' side of the PAM sequence is within, for example, about 1 to 50 bases, preferably about 1 to 15 bases, from the PAM sequence.

One embodiment of the present invention can include the knock-out poultry egg in which ovalbumin or ovomucoid is knocked-out as the oviduct-specific gene, although the present invention is not limited thereto. In a preferable embodiment of the knock-out of ovalbumin as the oviduct-specific gene, deletion, substitution, or insertion of a base or bases can be induced in a region corresponding to a base sequence represented by SEQ ID NO: 1 (OVATg1) and its vicinity. Further, in a preferable embodiment of the knock-out of ovomucoid as the oviduct-specific gene, deletion, substitution, or insertion of a base or bases can be induced in a region corresponding to a base sequence represented by SEQ ID NO: 6 (OVMTg2) and its vicinity.

In this description, for example, the "region corresponding to a base sequence represented by SEQ ID NO: 6 (OVMTg2)" includes a corresponding region in a homolog of the ovomucoid gene, and a person skilled in the art can recognize the region corresponding to the base sequence in the poultry of interest.

The ovomucoid protein before secretion contains 210 amino acids (210aa) (an initiation methionine is counted as the first amino acid) and has a signal peptide from 1 to 24th aa. Further, the PAM sequence of SEQ ID NO: 6 (OVMTg2) corresponds to 38 and 39th aa. Thus, in one embodiment of the present invention, the ovomucoid gene knock-out poultry egg expresses an ovomucoid mutant protein that lacks at least 160th aa and aa thereafter, preferably 100th aa and aa thereafter, more preferably 38th aa and aa thereafter.

Further, in a preferable embodiment of the present invention, the ovomucoid gene knock-out poultry egg is substantially free from endogenous ovomucoid. Being substantially free from endogenous ovomucoid means that endogenous ovomucoid is eliminated in an egg produced from an ovomucoid knock-out female poultry in which the ovomucoid gene is homozygously knocked-out.

One embodiment of the present invention can include the knock-out poultry egg in which ovalbumin or ovomucoid is knocked-out as the oviduct-specific gene, although the present invention is not limited thereto. In a preferable embodiment of the knock-out of ovalbumin as the oviduct-specific gene, deletion, substitution, or insertion of a base or bases can be induced in a region corresponding to a base sequence represented by SEQ ID NO: 1 (OVATg1) and its vicinity. Further, in a preferable embodiment of the knock-out of ovomucoid as the oviduct-specific gene, deletion, substitution, or insertion of a base or bases can be induced in a region corresponding to a base sequence represented by SEQ ID NO: 6 (OVMTg2) and its vicinity.

In this description, for example, the "region corresponding to a base sequence represented by SEQ ID NO: 1 (OVATg1)" includes a corresponding region in a homolog of the ovomucoid gene, and a person skilled in the art can recognize the region corresponding to the base sequence in the poultry of interest.

The ovomucoid protein before secretion contains 210 amino acids (210aa) (an initiation methionine is counted as the first amino acid) and has a signal peptide from 1 to 24th aa. Further, the PAM sequence of SEQ ID NO: 1 (OVATg1) corresponds to 38 and 39th aa. Thus, in one embodiment of the present invention, the ovomucoid gene knock-out poultry egg expresses an ovomucoid mutant protein that lacks at least 160th aa and aa thereafter, preferably 100th aa and aa thereafter, more preferably 38th aa and aa thereafter.

Further, in a preferable embodiment of the present invention, the ovomucoid gene knock-out poultry egg is substantially free from endogenous ovomucoid. Being substantially free from endogenous ovomucoid means that endogenous ovomucoid is eliminated in an egg produced from an ovomucoid knock-out female poultry in which the ovomucoid gene is homozygously knocked-out.

Genetically modified poultry can be produced by a conventional method from the genetically modified poultry primordial germ cell that is obtained by the gene modification method in one embodiment of the present invention. Further, a (knock-in and knock-out) egg can be obtained from the genetically modified poultry. Specific procedures will be described below.

The genetically modified primordial germ cell is transplanted in a blastoderm, blood stream, or gonadal region of a recipient early embryo. Several hundreds to several thousands of the cells are transplanted by microinjection into the blood stream around the time of starting a blood circulation, preferably on the second or third day after the start of egg incubation. Further, the endogenous primordial germ cells of the recipient may be inactivated or reduced in number in advance by a drug or ionizing radiation before performing transplantation. The egg incubation is continued for the transplanted embryo according to a conventional method to obtain a transplanted individual. The transplantation and egg incubation may be performed in an ex-ovo culture system in which an eggshell is changed or a windowing method in which an eggshell is not changed. The hatched individual can be raised under a normal condition to sexual maturity to obtain a living individual (a chimeric individual). The chimeric individual is mated with a wild-type or genetically modified individual, or the genetically modified chimeric individual to produce a poultry offspring having the genetic modification derived from the transplanted cell. The primordial germ cell of the present invention obtained by the genome editing has high proliferation ability and differentiates into a large number of sperms or eggs having high fertilizability in the chimeric individual. In order to increase an efficiency of this process, a mating test may be performed after examining a frequency of gene modification in genomes of gametes or evaluating a contribution ratio of the transferred cells, or the offspring may be selected by a feather color. The genetically modified homozygous poultry can be obtained by mating the female chimeric poultry in which the genetically modified female primordial germ cells are transplanted with the male chimeric poultry in which the genetically modified male primordial germ cells are transplanted. Further, the present invention is not limited to internal fertilization of the poultry. In a case where a technique such as differentiating a primordial germ cell into a germ cell in vitro is developed in the future, the genetically modified poultry can be produced by artificial insemination or intracytoplasmic sperm injection using such a technique.

In FIG. 2, FIG. 4A, FIG. 4B, and FIG. 16, the PAM sequence of OVMTg2 is "agg", however, NCBI databases include two kinds of sequences corresponding to chicken ovomucoid OVMTg2. Thus, the OVMTg2 sequence can be represented by TTTCCCAACGCTACAGACA(t or a)gg. The present invention includes all kinds of polymorphisms such as above.

In another embodiment of the present invention, the genome editing may be performed without culturing the primordial germ cell. In such a case, the endogenous primordial germ cell is genetically manipulated by infecting the early embryo with various viral vectors or injecting a plasmid vector as a liposome complex into a blood stream of the early embryo to establish a chimeric individual and a recombinant offspring. The primordial germ cell obtained by the genome editing includes the gene modification at a high frequency and has sufficiently high fertility to produce a recombinant poultry offspring or a genetically modified poultry offspring, and is thus useful in the present embodiment. In the present embodiment, the (endogenous) primordial germ cell can be genetically modified without culturing the primordial germ cell.

Examples of the viral vector used for gene manipulation by the genome editing include a retroviral vector, an adenoviral vector, an adeno-associated viral vector, a lentiviral vector, and the like. These viral vectors may be used for the genome editing both in the cultured primordial germ cell and the endogenous primordial germ cell.

For example, in a case where the endogenous primordial germ cell is modified by the genome editing, the genome editing in the primordial germ cell may be performed by constructing a viral vector expressing a nuclease that recognizes and cleaves any target sequences and an sgRNA using a genome editing viral vector commercially available from various companies, processing the viral vector into an infectious form by packaging, and administering a resulting material into a place where the primordial germ cell exits, such as a blastoderm, blood stream, or gonadal region of the poultry early embryo. In this manner, a genetically modified individual and a genetically modified product can be obtained in the following generation. The commercially available genome editing viral vectors are offered by a number of companies worldwide, and examples thereof include an "AAVpro (registered trademark) CRISPR/Cas9 Helper Free System (AAV2)" available from Takara Bio Inc., which uses the adeno-associated viral vector, a "Lentiviral CRISPR/Cas9 System" available from System Biosciences, LLC, which uses the lentiviral vector, and the like. In a case where the gene modification involves knock-in, the viral vector required for the gene editing may be used with, for example, a viral vector, plasmid, Bac vector, or single- or double-stranded DNA including a gene to be knocked-in.

Further, a genome editing plasmid and a donor construct, either without or in combination with the viral vector, may be prepared in a cell membrane permeable form, such as a liposome complex, and administered into a place where the primordial germ cell exits, such as a blastoderm, blood stream, or gonadal region of the poultry early embryo, to perform the genome editing in the primordial germ cell and obtain a genetically modified individual and a genetically modified product in the following generation.

In the knock-in poultry egg of the present invention obtained by the above method, an expression product of the exogenous gene is stably and highly expressed in the egg. Herein, "the expression product of the exogenous gene being stably and highly expressed in the egg" means that a protein encoded by the exogenous gene is expressed in an amount of about 1 mg or more per egg in each egg derived from different individuals. The expression amount of the exogenous protein is preferably about 10 mg or more, more preferably 100 mg or more, per egg. Further, for example, in a case where the exogenous gene is knocked-in at the chicken oviduct-specific gene locus, the exogenous gene product (protein) is expressed in the thick albumen of the egg produced from the knock-in female chicken in a concentration of 5 mg/ml. This concentration is much higher than that obtained by a conventional gene transfection method that does not rely on knock-in and thus causes random gene insertions. Since the exogenous gene is inserted in an identical location, variation in expression level is small between individuals and in the same individual. Further, because the present invention uses a technique to perform knock-in at a translation starting site of a gene that is actually expressing in a chicken individual, the gene expression is not reduced by an effect of gene silencing or the like in a G2 generation or later.

In the case where the exogenous gene is knocked-in at the oviduct-specific gene locus by the present method, the exogenous gene product (protein) in the egg produced from the knock-in female chicken is distributed to the thick albumen at a higher concentration than that distributed to the thin albumen. Thus, the exogenous gene product can be efficiently recovered by recovering a portion including the thick albumen.

An egg deprived of an albumen allergen protein can be obtained by raising an albumen allergen gene homozygous knock-out chicken generated by the present method and obtaining an egg thereof. Such an egg is expected to have low allergenicity. Non-Patent Literature 4 discloses an example of a heterozygous ovalbumin knock-out chicken. However, it is impossible to predict whether a homozygous knock-out chicken can be obtained or whether such a homozygous knock-out chicken can produce an egg in light of the overall common technical knowledge at that time or from the literature.

EXAMPLES

Hereinafter, the present invention will be described in detail by way of examples.

Production Example 1

Genome Editing Using Chicken Male Primordial Germ Cell

Production Example 1-1

Gene Constructions for Knock-in at Ovalbumin (OVA) Gene Locus and Knock-Out of Ovomucoid (OVM)

A CRISPR method was applied to a chicken male primordial germ cell line for targeting an ovalbumin and ovomucoid genes. As shown in FIG. 1 (ovalbumin) and FIG. 2 (ovomucoid), OVATg1 and OVMTg2 were tested respectively if they were suitable as targets.

A CRISPR plasmid for targeting the target sequence of the ovalbumin gene shown in FIG. 1 was constructed.

First, for targeting SEQ ID NO: 1 (OVATg1), oligo DNAs represented by SEQ ID NO: 2 and SEQ ID NO: 3 were synthesized, subjected to 5' phosphorylation by T4 polynucleotide kinase, and then annealed by heating a mixture of both oligo DNAs to 98° C. and slowly cooling the mixture to the room temperature. This DNA fragment was inserted into a BbsI cleavage site of a plasmid px330-Puro$^r$ in which a puromycin-resistant gene unit represented by SEQ ID NO: 4 was inserted into a NotI site of a plasmid px330 (Add-GENE, USA) to obtain px330-Puro$^r$-OVATg1. Further, the puromycin-resistant gene unit in px330-Puro$^r$-OVATg1 was replaced with a neomycin-resistant gene unit represented by SEQ ID NO: 5 to construct px330-Neo$^r$-OVATg1.

A CRISPR plasmid for targeting the target sequence of the ovomucoid gene shown in FIG. 2 was constructed. For targeting SEQ ID NO: 6 (OVMTg2), oligo DNAs represented by SEQ ID NO: 7 and SEQ ID NO: 8 were synthesized, phosphorylated, annealed, and inserted into a BbsI cleavage site of the plasmid px330-Puro$^r$ to obtain px330-Puro$^r$-OVMTg2.

Production Example 1-2

Knock-Out of Ovalbumin and Ovomucoid Genes

A chicken male primordial germ cell was collected from the blood stream of a male embryo of Barred Plymouth Rock to establish a cell line (the cell line was prepared according to Non-Patent Literature 3). The cell line was transiently transfected with the above genes (plasmids). After $1\times10^5$ to $5\times10^5$ male primordial germ line cells were rinsed with PBS and suspended into OPTI-MEM, 1.6 µg of px330-Neo$^r$-OVATg1 was transfected into the cells using 3 µl of Lipofectamine 2000 (Life Technologies, USA). Specifically, Lipofectamine 2000 and the plasmid were mixed in the 80 µl of OPTI-MEM, and the resulting mixture was added to the male primordial germ line cells. The primordial germ line cells mixed with the mixture were left still for about 5 minutes at the room temperature and then added with 500 it of medium containing no antibiotics. After being left still at 37° C. for about 1 to 4 hours, the primordial germ line cells were seeded onto feeder cells. The cell culture was added with neomycin (G418 disulfate salt, Nacalai, Japan) at a final concentration of 0.5 mg/ml from day 2 to day 4 after gene transfection. Then, the primordial germ line cells were rinsed to remove neomycin and cultured for another 1 to 2 weeks. After the cultured cells were collected and their genomic DNA was extracted, a PCR method was performed to amplify a part of the ovalbumin gene with oligo DNA primers represented by SEQ ID NO: 9 and SEQ ID NO: 10. The amplified DNA was sub-cloned into a TA vector (pGEM-T Easy, Promega, USA) to analyze a genome base sequence of a region including SEQ ID NO: 1 (OVATg1). As shown in FIG. 3, mutations including a deletion or substitution of the start codon were confirmed.

Next, a similar analysis was performed by targeting the ovomucoid gene. As described above, $1\times10^5$ to $5\times10^5$ male primordial germ line cells were transfected with 1.6 µg of px330-Puro$^r$-OVMTg2 using Lipofectamine 2000. The cell culture was added with puromycin at a final concentration of 1 µg/ml from day 2 to day 4 after gene transfection. The cells were rinsed to remove puromycin and cultured for another 1 to 2 weeks. After the cells were collected and their genomic DNA was extracted, a PCR method was performed to amplify a part of the ovomucoid gene with oligo DNA primers represented by SEQ ID NO: 11 and SEQ ID NO: 12. The amplified DNA was sub-cloned into a TA vector to analyze a genome base sequence of a region including SEQ ID NO: 6 (OVMTg2). Gene deletion was observed in 21 out of 23 clones analyzed (91%) in the region including SEQ ID NO: 6 (OVMTg2) of the ovomucoid gene. On the other hand, gene deletion was observed in 0 out of 24 clones (0%) in a control group not selected by a drug. An example of gene mutations found in the region including OVMTg2 are shown in FIG. 4A. These results show that a mutation efficiency can be markedly increased in the genome editing of a gene of the poultry primordial germ cell by introducing a drug-resistant gene and transiently performing a drug selection, in particular, a high mutation efficiency can be obtained by the puromycin-resistant gene and the drug selection using puromycin.

Production Example 1-3

Establishing Genome Edited Chicken

The px330-Puro$^r$-OVMTg2 plasmid was transfected into Barred. Plymouth Rock primordial germ cells in a manner described in Production example 1-2 and the drug selected cells were cultured. The cultured cells were transplanted into a blood stream of a 2.5-day-old White Leghorn embryo (a recipient embryo) by microinjection. Prior to transplantation, a fertilized egg was irradiated with ionizing radiation at 5 Gy or 6 Gy before incubation to reduce the number of endogenous primordial germ cells in the recipient embryo. The ionizing radiation was performed by gamma irradiation using a Gammacell 40 irradiator (Atomic Energy of Canada Ltd.).

After 2.5 days of incubation, a window having a diameter of about 2 cm was cut in the egg shell on a protruding side to expose an embryo. About 1,000 to 5,000 drug selected cells (suspended in 1 to 2 μl PBS) were transplanted in the blood stream of the recipient embryo at a hamburger-hamilton stage of 13 to 15 using a glass micropipette. After the window was sealed by a cellophane tape, the egg was incubated and hatched at a temperature of 38.5° C. and a humidity of 60 to 80% (a chimeric chick (G0)). Eight male chimeric chicks were raised to sexual maturity and their sperms were collected. After the genomic DNA was extracted from the sperms, a PCR method was performed to amplify a part of the ovomucoid gene with oligo DNA primers represented by SEQ ID NO: 11 and SEQ ID NO: 12. The amplified DNA was sub-cloned into a TA vector to analyze a genome base sequence of the region including SEQ ID NO: 6 (OVMTg2). Chimeric chickens #372 and #376 having a high mutation frequency (in both cases, the ovomucoid gene was mutated in 10 out of 11 clones after sub-cloning) were mated with wild-type Barred Plymouth Rock females to find 11 and 6 ovomucoid mutated chickens (chicks) out of 19 and 14 offsprings, respectively. One example of mutation in the ovomucoid gene is shown in an upper panel of FIG. 4S. This individual has a 5-base deletion immediately after a signal peptide of the ovomucoid protein, which causes a frame shift mutation in one allele of the ovomucoid gene. Further, representative examples of mutations (gene deletions) found around the target region of ovomucoid genome are shown in a lower panel of FIG. 4B. Several female and male individuals of ovomucoid heterozygous knock-out having frame shift mutations immediately after the signal peptide of the ovomucoid protein as represented above were obtained, allowing the production of a homozygous ovomucoid knock-out chicken by mating these individuals after sexual maturity.

Production Example 2

Human Interferon Gene Knock-in at Ovalbumin Gene Locus

Production Example 2-1

Knock-in for Establishing Primordial Germ Cell and Establishment of Knock-in Chimeric Chicken In order to insert an exogenous gene (human interferon β; IFNβ) at a translation starting site of the ovalbumin gene, a donor construct (an IFNβ donor construct) including a human interferon β gene represented by SEQ ID NO: 13 was created. This donor construct contains an about 2.8 kb 5' side of a translation starting site of ovalbumin, the human interferon β gene, a drug-resistant gene unit (PGK-puro$^r$), and an about 3.0 kb 3' side of the translation starting site of ovalbumin. This donor construct was inserted in a plasmid pBlue ScriptII (SK+) (Stratagene, USA, current Agilent Technologies) to create a pBS-IFNβ donor. As with production example 1, $1 \times 10^5$ to $5 \times 10^5$ primordial germ line cells were simultaneously transfected with 0.8 μg of px330-Neo$^r$-OVATg1 and 0.8 μg of the pBS-IFNβ donor using Lipofectamine 2000. The cell culture was added with puromycin at a final concentration of 1 μg/ml on the third day after gene transfection. After the medium was replaced as needed, cells capable of growing in the presence of puromycin at a final concentration of 1 μg/ml were recovered to prepare their genomic DNA. The genome PCR was performed to confirm that the donor construct was knocked-in at the ovalbumin gene locus. PCR in the 5' region was conducted as described below using a primer recognizing the exogenous gene on the donor construct and a primer recognizing a 5' region of ovalbumin not included in the donor construct. The PCR was conducted using an antisense primer recognizing interferon β, represented by SEQ ID NO: 14, and a sense primer recognizing a region of an about 3.0 kb 5' side of the translation starting site of ovalbumin, represented by SEQ ID NO: 15. Another round of PCR (nested PCR) was conducted with an amplification product using an antisense primer recognizing interferon β, represented by SEQ ID NO: 16, and a sense primer recognizing an about 2.85 kb 5' side of the translation starting site of ovalbumin not included in the donor construct, represented by SEQ ID NO: 17. As shown in FIG. 5A, when px330-Neo$^r$-OVATg1 and the donor construct were transfected and genome derived from the drug selected primordial germ cells (knock-in PGCs) was used as a template, an amplification product was detected at a position of about 2.9 k that was expected when the donor construct was inserted. In contrast, when genome derived from the control primordial germ cells not subjected to gene transfection (control PGCs) was used as a template, such an amplification product was not detected.

Similarly, a 3' region was examined by the genome PCR using a primer recognizing the exogenous gene on the donor construct and a primer recognizing a 3' region of ovalbumin not included in the donor construct. The PCR was conducted using a sense primer recognizing the drug-resistant gene unit, represented by SEQ ID NO: 18, and an antisense primer recognizing a region of an about 3.4 kb 3' side of the translation starting site of ovalbumin, represented by SEQ ID NO: 19. Another round of PCR (nested PCR) was conducted with an amplification product using a sense primer recognizing the drug-resistant gene unit, represented by SEQ ID NO: 20, and an antisense primer recognizing an about 3.2 kb 3' side of the translation starting site of ovalbumin not included in the donor construct, represented by SEQ ID NO: 21. As shown in FIG. 5A, when px330-Neo$^r$-OVATg1 and the donor construct were transfected and genome derived from the drug selected primordial germ cells (knock-in PGCs) was used as a template, an amplification product was detected at a position of about 3.4 k that was expected when the donor construct was inserted. In contrast, when genome derived from the control primordial germ cells not subjected to gene transfection (control PGCs) was used as a template, such an amplification product was not detected. These results suggest that the drug selected cell group includes a cell in which the donor construct including the exogenous gene portion is knocked-in at the ovalbumin gene locus. NO: 19. Another round of PCR (nested PCR) was conducted with The primordial germ cells containing the cell in which the IFNβ donor construct was knocked-in were transplanted into recipient embryos by the same method as described in Production example 1-3 and the embryos were incubated to obtain 4 chimeric male chickens (#411 to #414). After semen was collected from each chicken to isolate genomic DNA, PCR was conducted using primers represented by SEQ ID NO: 18 and SEQ ID NO: 19 (for amplifying a 3' side of interferon knocked-in at the ovalbumin gene), primers represented by SEQ ID NO: 15 and SEQ ID NO: 14 (for amplifying a 5' side of interferon knocked-in at the ovalbumin gene), and primers represented by SEQ ID NO: 15 and SEQ ID NO: 22 (for amplifying ovalbumin without a knock-in event) (FIG. 5B). The chimeric chickens #411 and #412 show signals that clearly prove the interferon knock-in at the ovalbumin gene locus at both the 3' side and 5' side. In particular, signal intensities of #411 are comparable to that of the transplanted parental cell line, suggesting that the sperms contain the interferon knock-in cells to the same extent as the parental cell line.

The chimeric chickens #411 and #412 were mated with wild-type female chickens (Barred Plymouth Rock) to obtain 28 and 19 offsprings, respectively. After wing shafts were collected from the offsprings to isolate their genomic DNA, PCR was conducted as described above using primers represented by SEQ ID NO: 18 and SEQ ID NO: 19 (for amplifying the 3' side of interferon knocked-in at the ovalbumin gene), primers represented by SEQ ID NO: 15 and SEQ ID NO: 14 (for amplifying the 5' side of interferon knocked-in at the ovalbumin gene), and primers represented by SEQ ID NO: 15 and SEQ ID NO: 22 (for amplifying ovalbumin without a knock-in event). Further, the same PCR was conducted with genome derived from a wild-type wing shaft (a negative control (NC)) and genome derived from the transplanted interferon donor vector knock-in primordial germ cells (a positive control (PC)). Eight out of 28 offsprings derived from #411 and 5 out of 19 offsprings derived from #412 showed signals that clearly proved the interferon knock-in at the ovalbumin gene locus at both the 3' side and 5' side, as were seen in the positive control. FIG. 5C shows an image of electrophoresis of PCR products from the offspring (female) derived from #411 and the offspring (female) derived from #412. These results indicate that the interferon donor vector is knocked-in at the ovalbumin gene locus in these female chicken offsprings.

(Production Example 2-2)
Improvement of Knock-in Efficiency

Studies were conducted to improve a gene knock-in efficiency. First, the drug resistance unit of the interferon β donor construct in the above production example 2-1 was changed from PGK-Puro$^r$ to SV40Pe-Neo$^r$ (SEQ ID NO: 23) to create an IFNβ-Neo donor construct <SEQ ID NO: 33>. This donor construct contains an about 2.8 kb 5' side of the translation starting site of ovalbumin, the human interferon β gene, the drug resistant gene unit (SV40Pe-Neo$^r$), and an about 3.0 kb 3' side of the translation starting site of ovalbumin. This donor construct was inserted in the plasmid pBlue ScriptII (SK+) to create a pBS-IFNβ-Neo donor. Further, as shown in FIG. 6A, a CRISPR plasmid for targeting the target sequence OVATg2 (SEQ ID NO: 24) of ovalbumin partially overlapping with OVATg1 was constructed. Oligo DNAs represented by SEQ ID NO: 25 and SEQ ID NO: 26 were synthesized and, as described in production example 1-1, they were phosphorylated, annealed, and inserted, as a DNA fragment, into the BbsI cleavage site of px330 to construct a plasmid, px330-Puro$^r$-OVATg2, which also has the puromycin-resistant unit represented by SEQ ID NO: 4 inserted into a NotI site. After about $5\times10^5$ primordial germ line cells were prepared and divided into 3 groups, as described in production example 2-1, the cells were simultaneously transfected with 0.8 µg of px330-Neo$^r$-OVATg1 and 0.8 µg of the pBS-IFNβ donor (including the puromycin-resistant gene unit) (transfection group 1), or 0.8 µg of px330-Puro$^r$-OVATg1 and 0.8 µg of the pBS-IFNβ-Neo donor (transfection group 2), or 0.8 µg of px330-Puro$^r$-OVATg2 and 0.8 µg of the pBS-IFNβ-Neo donor (transfection group 3) using Lipofectamine 2000. The transfected group 1 was added with puromycin at a final concentration of 1 µg/ml on the third day after gene transfection as was the case in production example 2-1. On the other hand, the transfection group 2 and transfection group 3 were cultured in the presence of puromycin at a final concentration of 1 µg/ml from day 2 to day 4 after gene transfection as was the case in production example 1-2. After rinsed, the cells were added with neomycin at a final concentration of 0.5 mg/ml and cultured. The number of cells was counted in each transfection group on day 24 after gene transfection. As a result, the transfection group 1 had $2\times10^4$ drug-resistant cells while the transfection groups 2 and 3 had $1\times10^5$ drug-resistant cells. Further, the cells in each transfection group were recovered to prepare their genomic DNA. Then, as described in production example 2-1, PCR was conducted using primers represented by SEQ ID NO: 18 and SEQ ID NO: 19 (for amplifying a 3' side of interferon knocked-in at the ovalbumin gene), primers represented by SEQ ID NO: 15 and SEQ ID NO: 14 (for amplifying a 5' side of interferon knocked-in at the ovalbumin gene), and primers represented by SEQ ID NO: 15 and SEQ ID NO: 22 (for amplifying ovalbumin without a knock-in event). Note that a primer represented by SEQ ID NO: 71 was used instead of the primer represented by SEQ ID NO: 18 in the transfection groups 2 and 3 (FIG. 6B). There is no considerable difference between the transfection groups 1 and 2 in terms of a PCR signal intensity ratio, suggesting that preparation of desired cells can be quicker in the method of the transfection group 2, in which the cells are briefly selected by puromycin and then selected by neomycin. Further, as compared to the transfection group 2, the transfection group 3 rarely contains ovalbumin not having a knock-in event, suggesting a better knock-in efficiency in the transfection group 3. These results suggest that the exogenous gene can be quickly and highly efficiently knocked-in at the ovalbumin gene locus by transfecting the primordial germ cells with the CRISPR construct targeting the OVATg2 sequence, inserting the puromycin-resistant gene and the neomycin-resistant gene into the CRISPR construct and the donor construct, respectively, and temporarily selecting with puromycin, and then selecting with neomycin.

Production Example 3

Human Antibody Gene Knock-in at Ovalbumin Gene Locus

Human interferon β in the interferon β donor construct in the above production example 2-1 was replaced with a human immunoglobulin gene represented by SEQ ID NO: 27 to create a donor construct (an immunoglobulin donor construct). In this donor construct, genes encoding an albumen lysozyme signal peptide, a human immunoglobulin heavy chain, a cleavage target sequence of furin protein, a 2A self-processing peptide, an albumen lysozyme signal peptide, and a human immunoglobulin light chain gene are arranged in tandem at a downstream of an about 2.8 kb 5' side of the translation starting site of ovalbumin, which are followed by the drug-resistant gene unit (PGK-Puro$^r$) and an about 3.0 kb 3' side of the translation starting site of ovalbumin. This donor construct is transcribed and translated to express an antibody protein composed of immunoglobulin heavy chains and light chains.

The immunoglobulin donor construct was inserted into the plasmid pBlue ScriptII (SK+) to create a pBS-immunoglobulin donor (a pBS-IgG(Hc+Lc) donor). After the donor construct was knocked-in into the male chicken primordial germ cells by the same method used for the pBS-IFNβ donor described above, the primordial germ cells were selected by puromycin and PCR was performed using genome of the selected cells as a template. The PCR in a 5' side was conducted using a primer represented by SEQ ID NO: 15 and an antisense primer recognizing the albumen lysozyme signal peptide, represented by SEQ ID NO: 28. Another round of PCR (nested PCR) was conducted with an amplification product using a primer represented by SEQ ID NO: 17 and an antisense primer recognizing the albumen lysozyme signal peptide, represented by SEQ ID NO: 29. The PCR in a 3' side was conducted in the same manner as for the knock-in of pBS-IFNβ donor described above. That is, the PCR was conducted using the primers represented by SEQ ID NO: 18 and SEQ ID NO: 19 and nested PCR was conducted with an amplification product using the primers represented by SEQ ID NO: 20 and SEQ ID NO: 21. As shown in FIG. 7, knock-in at the ovalbumin gene in the primordial germ cells was also observed using the immunoglobulin donor.

Further, similarly to production example 2-2, the drug resistance unit of the immunoglobulin donor construct was changed from PGK-Puro$^r$ to SV40Pe-Neo$^r$ (SEQ ID NO: 23) to create an immunoglobulin-Neo donor construct (SEQ ID NO: 30). In this donor construct, genes encoding an albumen lysozyme signal peptide, a human immunoglobulin heavy chain, a cleavage target sequence of furin protein, a 2A self-processing peptide, an albumen lysozyme signal peptide, and a human immunoglobulin light chain gene are arranged in tandem at a downstream of an about 2.8 kb 5' side of the translation starting site of ovalbumin, which are followed by the drug-resistant gene unit (SV40Pe-Neo$^r$) and an about 3.0 kb 3' side of the translation starting site of ovalbumin. This donor construct was inserted into the plasmid pBlue ScriptII (SK+) to create a pBS-immunoglobulin-Neo donor. With the same method used in production example 1-2, about 2×10$^5$ primordial germ line cells were transfected with 0.8 μg of px330-Puro$^r$-OVATg2 and 0.8 μg of the pBS-immunoglobulin-Neo donor using 3 μl of Lipofectamine 2000. The cells were cultured in the presence of puromycin at a final concentration of 1 μg/ml from day 2 to day 4 after gene transfection. After rinsed, the cells were added with neomycin at a final concentration of 0.5 mg/ml and cultured. A cell group containing immunoglobulin knock-in cells was obtained after about 3 weeks of culturing. Using the same method as described in production example 1-3, the cell group was transplanted into a recipient embryo and the embryo was incubated to establish an immunoglobulin knock-in germline chimeric chicken. A chicken in which the human immunoglobulin gene is knocked-in at the ovalbumin gene locus is obtained in the following generation and such a chicken expresses an antibody protein composed of the human immunoglobulin heavy chains and light chains in the albumen.

Production Example 4

Human Collagen Gene Knock-in at Ovalbumin Gene Locus

Human interferon β in the interferon β donor construct in the above production example 2-1 was replaced with a human type I collagen gene represented by SEQ ID NO: 31 to create a donor construct (a collagen donor construct). In this donor construct, genes encoding an albumen lysozyme signal peptide, a human type I collagen α1 chain (COLLAGEN1A1), a cleavage target sequence of a furin protein, a 2A self-processing peptide, an albumen lysozyme signal peptide, and a human type I collagen α2 chain (COLLAGEN1A2) gene are arranged in tandem at a downstream of an about 2.8 kb 5' side of the translation starting site of ovalbumin, which are followed by the drug-resistant gene unit (PGK-Puro$^r$) and an about 3.0 kb 3' side of the translation starting site of ovalbumin. This donor construct is transcribed and translated to express a type I collagen protein composed of the human type I collagen α1 chains and α2 chain.

The collagen donor construct was inserted into the plasmid pBlue ScriptII (SK+) to create a pBS-COL1(A1+A2) donor. The pBS-COL1(A1+A2) donor was knocked-in into the male chicken primordial germ cells by the same method used for the pBS-IFNβ donor and pBS-IgG(Hc+Lc) donor described above. After knock-in, the primordial germ cells were selected by puromycin and PCR was conducted using genome of the selected cells as a template. The PCR in a 5' side was conducted in the same manner as for the pBS-IgG (Hc+Lc) donor. That is, the PCR was conducted using the primer represented by SEQ ID NO: 15 and the antisense primer recognizing the albumen lysozyme signal peptide, represented by SEQ ID NO: 28. Then, another round of PCR (nested PCR) was conducted with an amplification product using the primer represented by SEQ ID NO: 17 and the antisense primer recognizing the albumen lysozyme signal peptide, represented by SEQ ID NO: 29. The PCR in a 3' side was conducted in the same manner as for the knock-in of the pBS-IFNβ donor and pBS-IgG(Hc+Lc) donor described above. That is, the PCR was conducted using the primers represented by SEQ ID NO: 18 and SEQ ID NO: 19 and then nested PCR was conducted with an amplification product using the primers represented by SEQ ID NO: 20 and SEQ ID NO: 21. As shown in FIG. 8, knock-in at the ovalbumin gene in the primordial germ cells was also observed using the collagen donor.

Further, similarly to production example 2-2, the drug resistance unit of the collagen donor construct was changed from PGK-Puro$^r$ to SV40Pe-Neo$^r$ (SEQ ID NO: 23) to create a collagen-Neo donor construct (SEQ ID NO: 32). In this donor construct, genes encoding an albumen lysozyme signal peptide, the human type I collagen α1 chain (COLLAGEN1A1), the cleavage target sequence of furin protein, the 2A self-processing peptide, the albumen lysozyme signal peptide, and the human type I collagen α2 chain (COLLAGEN1A2) gene are arranged in tandem at a downstream of an about 2.8 kb 5' side of the translation starting site of ovalbumin, which are followed by the drug-resistant gene unit (SV40Pe-Neo$^r$) and an about 3.0 kb 3' side of the translation starting site of ovalbumin. This donor construct was inserted into the plasmid pBlue ScriptII (SK+) to create a pBS-collagen-Neo donor. Using the same method as described in production example 1-2, about $2\times10^5$ primordial germ line cells were transfected with 0.8 µg of px330-Puro$^r$-OVATg2 and 0.8 µg of the pBS-collagen-Neo donor using 3 µl of Lipofectamine 2000. The cells were cultured in the presence of puromycin at a final concentration of 1 µg/ml from day 2 to day 4 after gene transfection. After rinsed, the cells were added with neomycin at a final concentration of 0.5 mg/ml and cultured. A cell group containing collagen knock-in cells was obtained after about 3 weeks of culturing. Using the same method as described in production example 1-3, the cell group was transplanted into a recipient embryo and the embryo was incubated to establish a collagen knock-in germline chimeric chicken. A chicken in which the human collagen gene is knocked-in at the ovalbumin gene locus is obtained in the following generation and such a chicken expresses a protein complex composed of the human type I collagen α1 and α2 in the albumen.

Example 1

As described in above production example 2-1, the female and male chickens in which the human interferon β donor vector was knocked-in at the translation starting site of the ovalbumin gene locus were established.

(1) Characteristics of Knock-in Chicken and Knock-in Egg

The established knock-in chickens reached sexual maturity without showing a developmental abnormality or significant disease condition. The female knock-in chicken laid eggs. A content of the egg was examined by opening an eggshell. As a result, a cloudy thick albumen was found around an egg yolk. On the other hand, similar to a wild-type egg, a thin albumen having a low viscosity was observed. A typical image of opened egg is shown in FIG. 9.

(2) Identification of Interferon and Possible Enrichment in Thick Albumen

Next, the presence of human interferon β in the albumen was examined. The thick albumen and the thin albumen were recovered by a dropper and added with an equal volume of a sample buffer (0.125M Tris pH6.8, 10% 2-ME, 4% SDS, 10% glycerol, 0.1% BPB). These samples were serially diluted 10 folds 3 times, separated by electrophoresis using a 5-20% acrylamide gel, and transferred to a PVDF membrane. After the membrane was blocked from a non-specific binding of an antibody molecule by skim milk, the membrane was subjected to western blotting using an anti-human interferon β antibody (abcam ab85803, a rabbit polyclonal antibody) diluted 1,000 times as a primary antibody and an anti-rabbit HRP conjugated antibody (GE Healthcare NA934V) diluted 1,000 times as a secondary antibody. A result is shown in FIG. 10.

The antibodies detected bands of about 30 kDa at the same position as that of purified recombinant human interferon β (WAKO rhIFN-β). Further, this band was not detected in a wild-type egg at all. In FIG. 10, numbers of 1, $\frac{1}{10}$, and $\frac{1}{100}$ in each lane indicate relative amounts of samples subjected to electrophoresis and the lanes having the same number include the same amount of albumen liquid. Interestingly, only a small amount of interferon was identified in the thin albumen.

These results suggest the possibility that a relatively large amount of recombinant proteins expressed by gene knock-in are accumulated in the thick albumen.

(3) Large Amount of Interferon Proteins Detected in Thick Albumen (Estimated to be about 5 mg/ml)

Next, the thin albumen and thick albumen were collected from a wild-type egg (NC: negative control) and eggs (KI egg 1 and 2) derived from 2 human interferon β knock-in chickens. After each sample was diluted twice, an equal amount of sample was subjected to electrophoresis using a 5-20% acrylamide gel to visualize proteins contained in the albumen by Coomassie Brilliant Blue staining (CBB Stain One, Nacalai). A result is shown in FIG. 11. Similar to the previous western blotting result, clear bands are detected at a position of about 30 kDa in 2 knock-in eggs but not in the wild-type egg, indicating that these bands are human interferon β. Further, similar to the western blotting result, these human interferon β bands are hardly detected in the thin albumen subjected to electrophoresis. A comparison of ORB stained band signals revealed that amounts of human interferon β were significantly different between the thin albumen and the thick albumen although amounts of other albumen components such as ovotransferrin and ovalbumin were almost the same, demonstrating that human interferon β expressed by knock-in at the ovalbumin gene locus was dominantly accumulated in the thick albumen.

Further, a concentration of human interferon in the albumen can be estimated by analyzing the CBB staining image. An intensity of blue color caused by CBB staining is substantially proportional to an amount of proteins. A signal concentration of human interferon β having a relative amount of 1 is compared to that of ovalbumin having a relative amount of $\frac{1}{10}$ through a quantification analysis of NIH image to obtain a ratio between them of 1.01:1. A concentration of ovalbumin that accounts for nearly half of albumen proteins is about 50 mg/ml, thus a concentration of human interferon β is estimated to be about 5 mg/ml.

The present method achieves the expression of the exogenous gene at a very high concentration of 5 mg/ml. Further, the exogenous gene is inserted in an identical location, thus variation in an expression level is small between individuals and in the same individual. Further, the present method uses a technique to perform knock-in at a translation starting site of a gene that is actually expressing in a chicken individual, thus gene expression is not reduced by an effect of gene silencing or the like in a G2 generation or later. FIG. 12 compares amounts of interferon in the albumen of eggs that have been collected 3 times (day 1, day 4 and day 7) over a week. The amounts of interferon in 3 eggs are compared through a quantification analysis of NIH image to obtain a ratio between them of 1:0.92:0.96, thus there is almost no variation in the concentration of interferon in the thick albumen. Further, these knock-in eggs were kept at 18° C. after collection and cracked open at the same time. This shows that the exogenous protein interferon can stably exist in the albumen over a week without undergoing significant degradation or the like.

(4) Expression of Interferon in Eggs Derived from Different Individuals (Consistency of Interferon Expression)

Eggs were obtained from 4 interferon knock-in females 3 months after they laid the first eggs and then cracked open (FIG. 23). Every egg had cloudy thick albumen. Further, eggs were obtained from 5 chickens (#584, #766, #714, #645, and #640) and the thick albumen of each egg was subjected to electrophoresis and CBB staining in the same manner as described in above (3). Interferon bands were detected in all eggs (FIG. 17). The concentrations of interferon of #584, #766, #714, #645, and #640 are compared through a quantification analysis of NIH image to obtain a ratio between them of 1.0:1.0:0.94:0.91:0.89. In this ratio, a difference between the maximum concentration and minimum concentration is within 11%, demonstrating a very stable expression as compared to a variation in secretion concentrations observed between individuals (5 µg/ml to 100 µg/ml) in Non-Patent Literature 1. Having little individual difference is advantageous for obtaining a large amount of recombinant proteins using a plurality of recombinant chickens.

Example 2

(1) Attempt of Efficiently Extracting Interferon from Thick Albumen (Applicable Solubilization Treatment)

It is found that interferon β is in the thick albumen at a high concentration. This interferon β is preferably extracted and purified from the albumen for a general use. A purification technique includes various column treatments on the basis of molecular weight and chemical properties, however proteins are preferably solubilized in an aqueous solution before being subjected to the column treatment. An aqueous solution and an insoluble matter can be separated by a centrifugal operation. Thus, studies were conducted to examine whether interferon β in the thick albumen was collected in an aqueous solution or included in an insoluble matter.

The thick albumen in an amount of 200 µl was collected and subjected to centrifugation at 20,000×g for 15 minutes to separate a white precipitate fraction from a liquid fraction (a tube 1 in FIG. 13). Electrophoresis using an acrylamide gel shows that the liquid fraction contains human interferon β (lane 1 in FIG. 14), however an amount of human interferon β is clearly less than that included in an equivalent amount of the thick albumen before separation (lane 0 in FIG. 14). Thus, it was speculated that a majority of interferon β was included in the white precipitate caused by centrifugation. In order to solve this, several attempts have been made to reduce the white precipitate and increase a yield of interferon. In FIG. 13, a thick albumen liquid in an amount of 200 µl was added in each tube and subjected to the following treatments. The thick albumen liquid is added and mixed by inversion with a 4 times volume (800 µl) of a 3M saturated arginine solution (tube 2), added with a 4 times volume (800 µl) of the 3M saturated arginine solution and subjected to ultrasonic crushing (tube 3), added and mixed by inversion with a small amount of arginine (20 mg) and filled up with PBS to 1 ml (tube 4), added and mixed by inversion with a small amount of arginine hydrochloride (20 mg) and filled up with PBS to 1 ml (tube 5), filled up with PBS to 1 ml and subjected to the ultrasonic crushing (tube 6), added and mixed by inversion with arginine hydrochloride in a saturating amount or more (200 mg) (tube 7), added with a twice volume (400 µl) of the 3M saturated arginine solution and subjected to the ultrasonic crushing (tube 8), added with a small amount of arginine hydrochloride (20 mg) and subjected to the ultrasonic crushing (tube 9), or added with a small amount of sodium chloride (40 mg) and subjected to the ultrasonic crushing (tube 10). Although the white precipitates were still observed after centrifugation at 20,000×g for 15 minutes, the amounts of the white precipitates were reduced by all of these treatments as compared to that without a treatment (tube 1). In particular, the amounts of the white precipitate's were markedly reduced in the tubes 3, 6, 8, and 9, which were subjected to the ultrasonic crushing.

After supernatants were recovered, samples were prepared by adjusting their loading amounts to be equal on the basis of the original amounts of the thick albumen and subjected to electrophoresis using an acrylamide gel (FIG. 14). The lane number in FIG. 14 corresponds to the tube number in FIG. 13 except lane 0, in which the thick albumen in an equivalent amount was applied to electrophoresis without separation. Although there were some differences between lanes, lane 2 to lane 10 contained more interferon β than lane 1 of the non-treatment sample. In particular, the sample prepared by adding a 4 times volume of the 3M saturated arginine solution and performing the ultrasonic crushing (tube 3) contained a significant amount of interferon β. These results show that an amount of interferon β extracted in an aqueous solution from the thick albumen increases by a physical treatment such as the ultrasonic crushing and a chemical treatment such as adding arginine or an arginine buffer (more restrictively, a solubilization treatment of insoluble protein). The sample in tube 3 prepared by adding a 4 times volume of the 3M saturated arginine solution and performing the ultrasonic crushing was subjected to centrifugation at 20 k×g for 15 minutes to recover a supernatant. The supernatant was subjected to dialysis in PBS for 24 hours (hereinafter referred to as a thick albumen rough purification product). The thick albumen rough purification product is transparent without any precipitates, suggesting that some of the white precipitates were solubilized and transferred to the supernatant by a series of treatments.

(2) Activity of Interferon Produced in Chicken Egg.

Activity of interferon in the thin albumen, thick albumen, and thick albumen rough purification product was examined by a bioassay. HEK-blue IFN-α/β (Invivogen) is a cultured cell that secretes alkaline phosphatase by human interferon β added in a medium. Activity of human interferon β can be detected by adding a medium after reaction to an alkaline phosphatase substrate solution (Quanti-Blue; Invivogen) and examining a change in the substrate solution (a color change from red to blue for Quanti-Blue). The thin albumen, the thick albumen (the supernatant after centrifugation at 20 k×g for 15 minutes), and the thick albumen rough purification product (derived from tube 3) derived from the human interferon knock-in eggs were added to the culture media of HEK-blue IFN-α/β. Further, the thin albumen derived form a wild-type chicken egg and PBS were added to the media as a negative control and recombinant human interferon was added to the media as a positive control. The cells were cultured for 20 hours and supernatants of the culture media were added to the Quanti-Blue substrate solution to perform reactions at 37° C. for 1 hour. A result is shown in FIG. 15.

The human interferon β activity is detected in any of the thin albumen, the thick albumen centrifugation supernatant, and the thick albumen rough purification product derived from the interferon knock-in (IFN-KI) eggs, demonstrating that an unpurified knock-in egg product exhibits the interferon activity and such an activity remains after the solubilization treatment by the ultrasonic crushing or the arginine buffer. Thus, interferon derived from the chicken egg can be used as it is in the egg without a processing, after a simple processing such as a centrifugation fractionation, or after a processing such as solubilization and purification.

(3) Activity Quantification of Interferon Produced in Chicken Egg

Activity of interferon in the thick albumen was measured by a bioassay. As described in (2), the thick albumen (a supernatant obtained by the ultrasonic crushing followed by centrifugation at 20,000×g for 15 minutes) derived from a human interferon knock-in egg (collected 3 months after the first egg) was serially diluted 5 folds and 10 µl of each dilution was added to the HEK-blue IFN-α/β culture medium. As a comparison, commercially available recombinant human interferon β (Wako Pure Chemical Industries, Ltd.) in a concentration of 10 µg/ml was serially diluted 5 folds in the same manner and 10 µl of each dilution was added to the culture medium. The cells were cultured for 20 hours and supernatants of the culture media were added to the Quanti-Blue substrate solution to perform reactions at 37° C. for 1 hour. A result is shown in FIG. 18. In an upper series of reactions using supernatants of the culture media to which commercially available human interferon was added, a fourth well from the left has a color in which red and blue is mixed, whereas, in a lower series of reactions using supernatants of the media to which the thick albumen was added, an eighth well from the left has a color in which red and blue is mixed (in both dilution series, concentration decreases from left to right). Thus, the interferon activity in the thick albumen is 625 or more times higher than that of the 10 µ/ml commercially available interferon and a concentration of interferon in the thick albumen is estimated to be 6.25 mg/ml or more. About 16 ml of the thick albumen was recovered at this point, meaning that human interferon having activity equivalent to about 100 mg of the commercially available interferon could be obtained from one egg. As for price, 20 µg of the recombinant human interferon β available from Wako Pure Chemical Industries, Ltd. costs 39,000 Japanese Yen, thus 100 mg of interferon is worthy of 195,000,000 Japanese Yen (about 200 million Japanese Yen). Using the present method allows the production of a very large amount of human recombinant proteins in terms of activity.

(4) Analysis of Egg of Knock-in Chicken in G2 Generation

A G1 knock-in chicken (male) was mated with a wild-type female to establish G2 knock-in chickens (male and female). The G2 knock-in chickens were raised to sexual maturity to obtain eggs and the eggs were cracked open (right in FIG. 19). All obtained eggs had cloudy thick albumen as was the case for the egg derived from G1. Further, eggs were obtained from 3 G2 knock-in chickens and their thick albumen was subjected to electrophoresis. The thick albumen of the G1 derived egg was also subjected to electrophoresis for comparison. In a CBB staining image, interferon signals were detected in the G2 derived eggs as in the G1 derived egg. These results showed that the exogenous gene knocked-in at the oviduct gene could be stably expressed in the chicken egg over generations. This observation can guarantee a large-scale and long-term stable operation of the production of recombinant proteins using a knock-in chicken.

Example 3

An egg was obtained from the chicken in which the human antibody gene was knocked-in at the ovalbumin gene locus in a manner as described in production example 3. The presence of a human antibody protein in the albumen was examined. The albumen was added with an equal volume of a sample buffer (0.125M Tris pH6.8, 4% SDS, 10% glycerol, 0.1% BPB, note that 2-ME is not included). These samples were serially diluted 10 folds 3 times, separated by electrophoresis using a 5-20% acrylamide gel, and transferred to a PVDF membrane. After the membrane was blocked from a non-specific binding of an antibody molecule by skim milk, the membrane was subjected to western blotting using an anti-human immunoglobulin antibody (Jackson Immuno Research, Anti-Human IgG F(ab)) diluted 1,000 times as a primary antibody and an anti-rabbit HRP conjugated antibody (Jackson Immuno Research, Peroxidase-conjugated AffiniPure Goat Anti-Rabbit IgG (H+L)) diluted 1,000 times as a secondary antibody. A result is shown in FIG. 20.

The antibodies detected bands of about 200 kDa at the same position as that of a purified recombinant human antibody (trade name: Herceptin, Roche Ltd.) (right in FIG. 20). Further, this band was not detected in a wild-type egg at all (left in FIG. 20). These results suggest that a human antibody complex maintains a normal subunit structure in the chicken egg. In FIG. 20, numbers of 1/20, 1/200, and 1/2 k (=1/2000) in each lane indicate relative amounts of the samples subjected to electrophoresis when the undiluted albumen is taken as 1. A concentration of the antibody complex is estimated to be 1 mg/ml or more by comparison with a loaded amount of Herceptin of a known concentration (right in FIG. 20).

Example 4

(1) Ovomucoid Homozygous Gene Knock-Out Chicken

Ovomucoid is an albumen protein, however an expression dynamic of ovomucoid in an early developmental process or a function of ovomucoid in development has not been studied. An effect of loss of function of ovomucoid is completely unknown. As shown in production example 1-3, the inventors created the heterozygous ovomucoid knock-out chickens (male and female) using the genome editing technique. Further, the inventors established the chicken having a complete deletion of ovomucoid (the homozygous ovomucoid knock-out chicken) by mating the heterozygous chickens. As shown in FIG. 16, the male and female heterozygous knock-out chickens having the same 5-base deletion in an exon 3 encoding the ovomucoid protein were mated with each other after sexual maturity to obtain offsprings. As shown in FIG. 16, the offsprings included a homozygous knock-out chicken in addition to a wild-type and heterozygous knock-out chickens. Further, both male and female ovomucoid homozygous knock-out chickens were obtained and they have been growing healthily like a wild-type chicken without any morphological abnormalities. These results showed, for the first time, that loss of function of ovomucoid did not cause any effect on an initial development, such as lethality or morphological abnormalities.

(2) Usefulness of Ovomucoid Knock-Out Chicken Egg

The homozygous ovomucoid knock-out chicken does not secrete ovomucoid and thus produces an egg having no ovomucoid. Ovomucoid is a very strong allergen substance and it is known that allergenicity of ovomucoid is not lost by heating or enzymatic degradation. Needless to say, an ovomucoid deficient egg does not exhibit strong allergenicity caused by ovomucoid, thus it is clearly understood that the ovomucoid deficient egg is useful, as a low allergenic egg, for significantly reducing allergenicity in all products that use an egg, such as a raw food, a processed food, a vaccine produced in an egg, and a cosmetic raw material.

(3) Characteristics of Ovomucoid Knock-Out Chicken Egg

The homozygous knock-out female can produce an egg as it produced an egg almost every day at least for 6 months in a manner similar to that of a wild type. An image of a cracked open egg is shown in a left panel of FIG. 21. The knock-out egg is not visually different from a wild-type egg. Further, the knock-out egg is not markedly different from a normal chicken egg in processability as, for example, it is coagulated by heating (right in FIG. 21).

Further, a chicken individual can be produced by mating the homozygous knock-out chickens with each other. An egg, which was obtained by mating 5 bp-deletion homozygous male and female individuals with each other, was incubated to obtain an ovomucoid 5 bp-deletion homozygous individual in the G3 generation (FIG. 23). This result shows that a chicken can develop without the ovomucoid gene or the ovomucoid protein, that is, ovomucoid is not essential for the development of chicken.

INDUSTRIAL APPLICABILITY

Further Improvement in Expression Level of Knock-in Gene

Interferon β obtained in the present example had a very high concentration of 5 mg/ml, however a concentration of a recombinant protein in an egg can be further increased.

1. Homozygousing Knock-in Gene

The analyzed chicken egg was produced from the parental chickens having a genotype in which human interferon β was inserted into one allele of the ovalbumin gene locus (heterozygous gene knock-in). It is possible to obtain an individual that expresses a recombinant protein at a higher concentration by mating heterozygous gene knock-in parents with each other or mating germ line chimeric individuals having knock-in primordial germ cells with each other to create an individual in which human interferon β is inserted into both alleles (homozygous gene knock-in).

2. Improving Signal Peptide and Codon Usage

In the present example, human interferon β cDNA was knocked-in at the translation starting site of the ovalbumin gene. In this case, a signal peptide in use was from human interferon β, and it was not optimized for a chicken oviduct cell. Examples of the signal peptide that allows secretion in the chicken oviduct at a high efficiency include a signal peptide of a protein that is actually secreted from the oviduct. Specific examples of such a signal peptide include "MRSLLILVLCFLPLAALG" of albumen lysozyme and "MKLILCTVLSLGIAAVCFA" of ovotransferrin. Further, the present invention is not limited thereto and an artificial or natural signal peptide that allows protein secretion in a chicken cell at a high efficiency may be used. Knock-in of a desired protein having these signal peptides at its N terminus at the ovalbumin gene locus allows the production of the desired protein at a higher concentration. Further, protein production can be improved by optimizing a base sequence of cDNA to be knocked-in in accordance with a codon usage used in a chicken.

3. Increasing Copy Number of Inserted Gene

In the present example, only one gene was knocked-in, however a plurality of genes can be knocked-in in a tandem form that allows transcription and translation to simultaneously express the plurality of genes, thereby increasing their expression levels. The plurality of genes may be composed of a single gene or a plurality of kinds of genes and the number of genes may be any number. Specifically, when performing gene knock-in, a plurality of genes may be inserted by interposing a sequence such as IRES between them to facilitate transcription and translation and increase gene products. Further, a plurality of proteins may be arranged by interposing a 2A peptide or the like between them and simultaneously expressed under control of the ovalbumin promoter. In this manner, a larger amount of proteins can be produced by cleaving the peptides.

As a preferable embodiment, the light chain gene and heavy chain gene of the human antibody gene and α1 and α2 of the human type I collagen gene are each tandemly connected via the 2A peptide gene and knocked-in into a chicken.

4. Usefulness of Knock-Out Chicken Egg

The homozygous ovomucoid knock-out chicken does not secrete ovomucoid and thus produce an egg having no ovomucoid. Ovomucoid is a very strong allergen substance and it is known that allergenicity of ovomucoid is not lost by heating or enzymatic degradation. Needless to say, an ovomucoid deficient egg does not have strong allergenicity caused by ovomucoid, thus it is obvious that the ovomucoid deficient egg is useful, as a low allergenic egg, for significantly reducing allergenicity in all products that use an egg, such as a raw food, a processed food, a vaccine produced in an egg, and a cosmetic raw material. Further, an exogenous gene can be expressed in an albumin allergen knock-out chicken egg by breeding or using a genome edited primordial germ cell, and it is clearly understood that purification of the exogenous gene product produced in this manner can simplify an allergen removing process.

A poultry egg in which an oviduct-specific gene other than ovomucoid is knocked-out is useful for significantly reducing allergenicity as is the case for ovomucoid.

The invention claimed is:

1. A genetically modified chicken egg whose genome comprises an exogenous nucleotide sequence comprising a nucleic acid sequence encoding an exogenous protein and a stop codon in exon 2 of an endogenous ovalbumin gene, wherein:
   i) the nucleic acid sequence encoding the exogenous protein and the stop codon are operably linked to an endogenous ovalbumin promoter;
   ii) the endogenous ovalbumin gene is inactivated;
   iii) the chicken egg expresses the exogenous protein; and
   iv) the chicken egg has reduced expression of functional endogenous albumin.

2. The chicken egg of claim 1, wherein the nucleotide sequence further comprises a nucleic acid sequence encoding a drug-resistance protein operably linked to the ovalbumin promoter, and the chicken egg expresses the drug-resistance protein.

3. The chicken of claim 1, wherein the 5' end of the exogenous nucleotide sequence is within the nucleotides of SEQ ID NO: 1 or SEQ ID NO: 24.

4. The chicken egg of claim 1, wherein the protein is expressed in the egg in an amount of 1 mg or more.

5. The chicken egg of claim 1, wherein the protein is expressed in the albumen of the egg.

6. The chicken egg of claim 1, wherein the protein is interferon β, immunoglobulin, or collagen.

7. The chicken egg of claim 1, wherein the protein is a human protein.

8. A method of producing a genetically modified knock-in chicken egg, the method comprising:
  a) inserting an exogenous nucleotide sequence into exon 2 of an endogenous ovalbumin gene of an isolated chicken primordial germ cell (PGC), wherein:
    i) the exogenous nucleotide sequence comprises a nucleic acid sequence encoding an exogenous protein and a stop codon;
    ii) the nucleic acid sequence encoding the exogenous protein and the stop codon are operably linked to an endogenous ovalbumin promoter; and
    iii) the endogenous ovalbumin gene is inactivated;
  b) transplanting the PGC obtained in step a) into a recipient chicken embryo;
  c) producing a genetically modified knock-in chicken from the chicken embryo in step b); and
  d) obtaining a genetically modified knock-in chicken egg from the knock-in chicken of step c), wherein the chicken egg:
    i) has a genome comprising the exogenous nucleotide sequence comprising the nucleic acid sequence encoding the exogenous protein and a stop codon in exon 2 of the endogenous ovalbumin gene operably linked to the endogenous ovalbumin promoter;
    ii) functionally expresses the exogenous protein; and
    iii) has reduced expression of functional endogenous albumin.

9. The method of claim 8, the exogenous nucleotide sequence in step a) is inserted using CRISPR and guide RNA.

10. The method of claim 9, wherein the nucleotide sequence in step a) is inserted into the nucleotide sequence contains a 2.8 kb 5' homology arm and a 3.0 kb homology arm that allow insertion into exon 2 of the endogenous ovalbumin gene.

11. A method of expressing an exogenous protein in a genetically modified knock-in chicken egg, the method comprising:
  a) producing a genetically modified knock-in chicken egg using the method of claim 8; and
  b) recovering the exogenous protein from the chicken egg.

12. A genetically modified chicken whose genome comprises an exogenous nucleotide sequence comprising a nucleic acid sequence encoding an exogenous protein and a stop codon in exon 2 of an endogenous ovalbumin gene, wherein:
  i) the nucleic acid sequence encoding the protein and the stop codon are operably linked to an endogenous ovalbumin promoter;
  ii) the endogenous ovalbumin gene is inactivated;
  iii) the chicken is capable of laying an egg that expresses the exogenous protein and has reduced expression of functional endogenous albumin.

13. The genetically modified chicken according to claim 12, wherein the chicken is female.

* * * * *

SEQUENCE LISTING

<160> NUMBER OF SEQ ID NOS: 71

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
acaactcaga gttcaccatg gg                                            22

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2

```
caccgacaac tcagagttca ccat                                              24
```

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3

```
aaacatggtg aactctgagt tgtc                                              24
```

<210> SEQ ID NO 4
<211> LENGTH: 1383
<212> TYPE: DNA
<213> ORGANISM: Artificial Sequence
<220> FEATURE:
<223> OTHER INFORMATION: puromycin resistant gene unit

<400> SEQUENCE: 4

```
gcggccgcgg gaattcgatt gtcgaccctc gacctcgaaa ttctaccggg taggggaggc        60
gcttttccca aggcagtctg gagcatgcgc tttagcagcc ccgctgggca cttggcgcta       120
cacaagtggc ctctggcctc gcacacattc cacatccacc ggtaggcgcc aaccggctcc       180
gttctttggt ggccccttcg cgccaccttc tactcctccc ctagtcagga agttcccccc       240
cgccccgcag ctcgcgtcgt gcaggacgtg acaaatggaa gtagcacgtc tcactagtct       300
cgtgcagatg gacagcaccg ctgagcaatg aagcgggta ggcctttggg gcagcggcca       360
atagcagctt tgctccttcg ctttctgggc tcagaggctg ggaaggggtg ggtccggggg       420
cgggctcagg ggcgggctca ggggcggggc gggcgcccga aggtcctccg gaggcccggc       480
attctgcacg cttcaaaagc gcacgtctgc cgcgctgttc tcctcttcct catctccggg       540
cctttcgacc tgcatccatc tagatctaga tcagcttacc atgaccgagt acaagcccac       600
ggtgcgcctc gccacccgcg acgacgtccc cagggccgta cgcaccctcg ccgccgcgtt       660
cgccgactac cccgccacgc gccacaccgt cgatccggac cgccacatcg agcgggtcac       720
cgagctgcaa gaactcttcc tcacgcgcgt cgggctcgac atcggcaagg tgtgggtcgc       780
ggacgacggc gccgcggtgg cggtctggac cacgccggag agcgtcgaag cggggcggt       840
gttcgccgag atcggcccgc gcatggccga gttgagcggt tcccggctgg ccgcgcagca       900
acagatggaa ggcctcctgg cgccgcaccg gcccaaggag cccgcgtggt tcctggccac       960
cgtcggcgtc tcgcccgacc accagggcaa gggtctgggc agcgccgtcg tgctccccgg      1020
agtggaggcg gccgagcgcg ccggggtgcc cgccttcctg gagacctccg cgccccgcaa      1080
cctcccttc tacgagcggc tcggcttcac cgtcaccgcc gacgtcgagg tgcccgaagg      1140
accgcgcacc tggtgcatga cccgcagccc ggtgcctgac gcccgcccca cgacccgcag      1200
cgcccgaccg aaaggagcgc acgaccccat gcatcgatga tgccaataaa gatatcattg      1260
atgagtttgg acaaaccaca actagaatgc agtgaaaaaa atgctttatt tgtgaaattt      1320
gtgatgctat tgctttattt gtaaccatta taagctgcaa atcactagtg aattcgcggc      1380
cgc                                                                   1383
```

<210> SEQ ID NO 5
<211> LENGTH: 1834
<212> TYPE: DNA
<213> ORGANISM: Artificial Sequence

```
<220> FEATURE:
<223> OTHER INFORMATION: neomycin resistant gene unit

<400> SEQUENCE: 5
gcggccgcgg gaattcgatt aagtcgactc aggtggcact tttcggggaa atgtgcgcgg      60
aaccccatt  tgtttatttt  tctaaataca ttcaaatatg tatccgctca tgagacaata    120
```

```
<220> FEATURE:
<223> OTHER INFORMATION: neomycin resistant gene unit

<400> SEQUENCE: 5
gcggccgcgg gaattcgatt aagtcgactc aggtggcact tttcggggaa atgtgcgcgg      60
aaccccatt  tgtttatttt tctaaataca ttcaaatatg tatccgctca tgagacaata    120
accctgataa atgcttcaat aatattgaaa aaggaagagt cctgaggcgg aaagaaccag    180
ctgtggaatg tgtgtcagtt agggtgtgga aagtccccag gctccccagc aggcagaagt    240
atgcaaagca tgcatctcaa ttagtcagca accaggtgtg gaaagtcccc aggctcccca    300
gcaggcagaa gtatgcaaag catgcatctc aattagtcag caaccatagt cccgccccta    360
actccgccca tcccgcccct aactccgccc agttccgccc attctccgcc ccatggctga    420
ctaattttt  ttatttatgc agaggccgag gccgcctcgg cctctgagct attccagaag    480
tagtgaggag cttttttgg aggcctaggc ttttgcaaag atcgatcaag agacaggatg    540
aggatcgttt cgcatgattg aacaagatgg attgcacgca ggttctccgg ccgcttgggt    600
ggagaggcta ttcggctatg actgggcaca acagacaatc ggctgctctg atgccgccgt    660
gttccggctg tcagcgcagg ggcgcccggt tcttttttgtc aagaccgacc tgtccggtgc    720
cctgaatgaa ctgcaagacg aggcagcgcg gctatcgtgg ctggccacga cgggcgttcc    780
ttgcgcagct gtgctcgacg ttgtcactga agcgggaagg gactggctgc tattgggcga    840
agtgccgggg caggatctcc tgtcatctca ccttgctcct gccgagaaag tatccatcat    900
ggctgatgca atgcggcggc tgcatacgct tgatccggct acctgcccat tcgaccacca    960
agcgaaacat cgcatcgagc gagcacgtac tcggatggaa gccggtcttg tcgatcagga   1020
tgatctggac gaagagcatc aggggctcgc gccagccgaa ctgttcgcca ggctcaaggc   1080
gagcatgccc gacggcgagg atctcgtcgt gacccatggc gatgcctgct tgccgaatat   1140
catggtggaa aatggccgct tttctggatt catcgactgt ggccggctgg gtgtggcgga   1200
ccgctatcag gacatagcgt tggctacccg tgatattgct gaagagcttg gcggcgaatg   1260
ggctgaccgc ttcctcgtgc tttacggtat cgccgctccc gattcgcagc gcatcgcctt   1320
ctatcgcctt cttgacgagt tcttctgagc gggactctgg ggttcgaaat gaccgaccaa   1380
gcgacgccca acctgccatc acgagatttc gattccaccg ccgccttcta tgaaaggttg   1440
ggcttcggaa tcgttttccg gacgccggc tggatgatcc tccagcgcgg ggatctcatg   1500
ctggagttct cgcccaccc  taggggagg ctaactgaaa cacggaagga acaataccg   1560
gaaggaaccc gcgctatgac ggcaataaaa agacagaata aaacgcacgg tgttgggtcg   1620
tttgttcata acgcggggt  tcggtcccag ggctggcact ctgtcgatac cccaccgaga   1680
ccccattggg gccaatacgc ccgcgtttct tccttttccc cacccaccc  cccaagttcg   1740
ggtgaaggcc cagggctcgc agccaacgtc ggggcggcag gccctgccat agcctcaggt   1800
tactcgagtt aatcactagt gaattcgcgg ccgc                                1834

<210> SEQ ID NO 6
<211> LENGTH: 22
<212> TYPE: DNA
<213> ORGANISM: chiken

<400> SEQUENCE: 6
tttcccaacg ctacagacat gg                                               22

<210> SEQ ID NO 7
```

-continued

```
<211> LENGTH: 24
<212> TYPE: DNA
<213> ORGANISM: Artificial Sequence
<220> FEATURE:
<223> OTHER INFORMATION: primer

<400> SEQUENCE: 7
caccgtttcc caacgctaca gaca                                          24

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
aaactgtctg tagcgttggg aaac                                          24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
ctatgtacag cattccatcc ttac                                          24

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
ttcagcctct gagctatgca gtt                                           23

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
ctacaaaatg tcactttgtc c                                             21

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
tgatgtctag gcaaccgagt gt                                            22

<210> SEQ ID NO 13
<211> LENGTH: 8136
<212> TYPE: DNA
<213> ORGANISM: human

<400> SEQUENCE: 13
gtcgacctta agtcctcaga cttggcaagg agaatgtaga tttctacagt atatatgttt   60
```

```
tcacaaaagg aaggagagaa acaaaagaaa atggcactga ctaaacttca gctagtggta      120
taggaaagta attctgctta acagagattg cagtgatctc tatgtatgtc ctgaagaatt      180
atgttgtact ttttccctc attttaaat caaacagtgc tttacagagg tcagaatggt        240
ttctttactg tttgtcaatt ctattatttc aatacagaac aatagcttct ataactgaaa      300
tatatttgct attgtatatt atgattgtcc ctcgaaccat gaacactcct ccagctgaat      360
ttcacaattc ctctgtcatc tgccaggcca ttaagttatt catggaagat ctttgaggaa      420
cactgcaagt tcatatcata aacacatttg aaattgagta ttgttttgca ttgtatggag      480
ctatgttttg ctgtatcctc agaaaaaaag tttgttataa agcattcaca cccataaaaa      540
gatagattta atattccag ctataggaaa gaaagtgcgt ctgctcttca ctctagtctc       600
agttggctcc ttcacatgca cgcttcttta tttctcctat tttgtcaaga aaataatagg      660
tcacgtcttg ttctcactta tgtcctgcct agcatggctc agatgcacgt tgtacataca     720
agaaggatca aatgaaacag acttctggtc tgttactaca accatagtaa taagcacact     780
aactaataat tgctaattat gttttccatc tccaaggttc ccacatttt  ctgttttctt     840 aaagatccca ttatctggtt gtaactgaag ctcaatggaa catgagcaat atttcccagt     900
cttctctccc atccaacagt cctgatggat tagcagaaca ggcagaaaac acattgttac     960
ccagaattaa aaactaatat ttgctctcca ttcaatccaa aatggaccta ttgaaactaa     1020
aatctaaccc aatcccatta atgatttct atggcgtcaa aggtcaaact tctgaaggga     1080
acctgtgggt gggtcacaat tcaggctata tattccccag ggctcagcca gtgtctgtac    1140
atacagctag aaagctgtat tgcctttagc actcaagctc aaaaggtaag caactctctg    1200
gaattacctt ctctctatat tagctcttac ttgcacctaa actttaaaaa attaacaatt    1260
attgtgttat gtgttgtatc tttaagggtg aagtacctgc gtgataccc  ctataaaaac    1320 ttctcacctg tgtatgcatt ctgcactatt ttattatgtg taaaagcttt gtgtttgttt    1380
tcaggaggct tattctttgt gcttaaaata tgtttttaat ttcagaacat cttatcctgt    1440
cgttcactat ctgatatgct ttgcagtttg cctgattaac ttctagccct acagagtgca    1500
cagagagcaa atcatggtg  ttcagtgaat tctggggagt tatttaatg tgaaaattct    1560 ctagaagttt aattcctgca aagtgcagct gctgatcact acacaagata aaaatgtggg    1620
gggtgcataa acgtatattc ttacaataat agatacatgt gaacttgtat acagaaaaga    1680
aaatgagaaa aatgtgtgtg cgtatactca cacacgtggt cagtaaaaac ttttgagggg    1740
tttaatacag aaaatccaat cctgaggccc cagcactcag tacgcatata aagggctggg    1800
ctctgaagga cttctgactt tcacagatta tataaatctc aggaaagcaa ctagattcat    1860
gctggctcca aaagctgtgc tttatataag cacactggct atacaatagt tgtacagttc    1920
agctctttat aatagaaaca gacagaacaa gtataaatct tctattggtc tatgtcatga    1980
acaagaattc attcagtggc tctgttttat agtaaacatt gctattttat catgtctgca    2040
tttctcttct gtctgaatgt caccactaaa atttaactcc acagaaagtt tatactacag    2100
tacacatgca tatctttgag caaagcaaac catacctgaa agtgcaatag agcagaatat    2160
gaattacatg cgtgtctttc tcctagacta catgaccca  tataaattac attccttatc    2220
tattctgcca tcaccaaaac aaaggtaaaa atactttga agatctactc atagcaagta    2280
gtgtgcaaca acagatatt  tctctacatt tattttagg gaataaaaat aagaaataaa    2340
atagtcagca agcctctgct ttctcatata tctgtccaaa cctaaagttt actgaaattt    2400
```

```
gctctttgaa tttccagttt tgcaagccta tcagattgtg ttttaatcag aggtactgaa    2460
aagtatcaat gaattctagc tttcactgaa caaaaatatg tagaggcaac tggcttctgg    2520
gacagtttgc tacccaaaag acaactgaat gcaaatacat aaatagattt atgaatatgg    2580
ttttgaacat gcacatgaga ggtggatata gcaacagaca cattaccaca gaattacttt    2640
aaaactactt gttaacattt aattgcctaa aaactgctcg taatttactg ttgtagccta    2700
ccatagagta ccctgcatgg tactatgtac agcattccat ccttacattt tcactgttct    2760
gctgtttgct ctagacaact cagagttcac catgaccaac aagtgtctcc tccaaattgc    2820
tctcctgttg tgcttctcca ctacagctct ttccatgagc tacaacttgc ttggattcct    2880
acaaagaagc agcaattttc agtgtcagaa gctcctgtgg caattgaatg ggaggcttga    2940
atattgcctc aaggacagga tgaactttga catccctgag gagattaagc agctgcagca    3000
gttccagaag gaggacgccg cattgaccat ctatgagatg ctccagaaca tctttgctat    3060
tttcagacaa gattcatcta gcactggctg gaatgagact attgttgaga acctcctggc    3120
taatgtctat catcagataa accatctgaa gacagtcctg gaagaaaaac tggagaaaga    3180
agatttcacc aggggaaaac tcatgagcag tctgcacctg aaaagatatt atgggaggat    3240
tctgcattac ctgaaggcca aggagtacag tcactgtgcc tggaccatag tcagagtgga    3300
aatcctaagg aacttttact tcattaacag acttacaggt tacctccgaa actgaagatc    3360
tcctagcctg tgcctctggt cgactcgctg atcagcctcg actttgcctt ctagttgcca    3420
gccatctgtt gtttgcccct ccccgtgcc ttccttgacc ctggaaggtg ccactcccac    3480
tgtcctttcc taataaaatg aggaaattgc atcgcattgt ctgagtaggt gtcattctat    3540 tctgggggt ggggtgggc aggacagcaa gggggaggat tgggaagaca atagcaggca    3600
ctcgaccctc gacctcgaaa ttctaccggg taggggaggc gcttttccca aggcagtctg    3660
gagcatgcgc tttagcagcc ccgctgggca cttggcgcta cacaagtggc ctctggcctc    3720
gcacacattc cacatccacc ggtaggcgcc aaccggctcc gttctttggt ggccccttcg    3780
cgccaccttc tactcctccc ctagtcagga agttcccccc cgccccgcag ctcgcgtcgt    3840
gcaggacgtg acaaatggaa gtagcacgtc tcactagtct cgtgcagatg acagcaccg    3900 ctgagcaatg gaagcgggta ggcctttggg gcagcggcca atagcagctt tgctccttcg    3960 cttctgggc tcagaggctg gaaggggtg ggtccggggg cgggctcagg ggcgggctca    4020
ggggcggggc gggcgcccga aggtcctccg gaggcccggc attctgcacg cttcaaaagc    4080
gcacgtctgc cgcgctgttc tcctcttcct catctccggg cctttcgacc tgcatccatc    4140
tagatctaga tcagcttacc atgaccgagt acaagcccac ggtgcgcctc gccacccgcg    4200
acgacgtccc cagggccgta cgcaccctcg ccgccgcgtt cgccgactac cccgccacgc    4260
gccacaccgt cgatccggac cgccacatcg agcgggtcac cgagctgcaa gaactcttcc    4320
tcacgcgcgt cggactcgac atcggcaagg tgtgggtcgc ggacgacggc gccgcggtgg    4380
cggtctggac cacgccggag agcgtcgaag cgggggcggt gttcgccgag atcggcccgc    4440
gcatggccga gttgagcggt tccggctgg ccgcgcagca acagatggaa ggcctcctgg    4500
cgccgcaccg gcccaaggag cccgcgtggt tcctggccac cgtcggcgtc tcgcccgacc    4560
accagggcaa gggtctgggc agcgccgtcg tgctccccgg agtggaggcg gccgagcgcg    4620
ccggggtgcc cgccttcctg gagacctccg cgccccgcaa cctccccttc tacgagcggg    4680
tcggcttcac cgtcaccgcc gacgtcgagg tgcccgaagg accgcgcacc tggtgcatga    4740
cccgcaagcc cggtgcctga cgcccgcccc acgacccgca gcgcccgacc gaaaggagcg    4800
```

```
cacgacccca tgcatcgatg atgccaataa agatatcatt gatgagtttg acaaaccac    4860 aactagaatg cagtgaaaaa aatgctttat ttgtgaaatt tgtgatgcta ttgctttatt    4920
tgtaaccatt ataagctgca tatcgaattc ccgcggccgc gggaattcga ttccatcggt    4980
gcagcaagca tggaatttg ttttgatgta ttcaaggagc tcaaagtcca ccatgccaat    5040
gagaacatct tctactgccc cattgccatc atgtcagctc tagccatggt atacctgggt    5100
gcaaaagaca gcaccaggac acagataaat aaggtgagcc tacagttaaa gattaaaacc    5160
tttgccctgc tcaatggagc cacagcactt aattgtatga taatgtccct tggaaactgc    5220
atagctcaga ggctgaaaat ctgaaaccag agttatctaa aagtgtggcc acctccaact    5280
cccagagtgt tacccaaatg cactagctag aaatcttgaa actggattgc ataacttctt    5340
tttgtcataa ccattatttc agctactatt attttcaatt acaggttgtt cgctttgata    5400
aacttccagg attcggagac agtattgaag ctcaggtaca gaaataattt cacctccttc    5460
tctatgtccc tttcctctgg aagcaaaata cagcagatga agcaatctct tagctgttcc    5520
aagccctctc tgatgagcag ctagtgctct gcatccagca gttgggagaa cactgttcat    5580
aagaacagag aaaagaagg aagtaacagg ggattcagaa caaacagaag ataaaactca    5640
ggacaaaaat accgtgtgaa tgaggaaact tgtggatatt tgtacgctta agcaagacag    5700
ctagatgatt ctggataaat gggtctggtt ggaaaagaag gaaagcctgg ctgatctgct    5760
ggagctagat tattgcagca ggtaggcagg agttccctag agaaaagtat gagggaatta    5820
cagaagaaaa acagcacaaa attgtaaata ttggaaaagg accacatcag tgtagttact    5880
agcagtaaga cagacaggat gaaaaatagt tttgtaaaca gaagtatcta actactttac    5940
tctgttcata cactatgtaa aacctactaa gtaataaaac tagaataaca acatctttct    6000
ttctctttgt attcagtgtg gcacatctgt aaacgttcac tcttcactta gagacatcct    6060
caaccaaatc accaaaccaa atgatgttta ttcgttcagc cttgccagta gactttatgc    6120
tgaagagaga tacccaatcc tgccagtaag ttgctctaaa atctgatctg agtgtatttc    6180
catgccaaag ctctaccatt ctgtaatgca aaaacagtca gagttccaca tgtttcacta    6240
agaaaatttc ttttctcttt gttttacaa atgaaagaga ggacaaataa catttctcta    6300
tcaccgacct gaaactctac agtcttcaga gaatgaatgg cttgctaaaa gaatgtcaaa    6360
tcttaccata cagctattt atattacact actaaataca ctataaggca tagcatgtag    6420
taatacactg taaatagct ttttacacta ctatattatt aatatctgtt aattccagtc    6480
ttgcatttca catttgcaaa cgttttgaa attcgtatct gaaagctgaa tactcttgct    6540
ttacaggaat acttgcagtg tgtgaaggaa ctgtatagag gaggcttgga acctatcaac    6600
tttcaaacag ctgcagatca agccagagag ctcatcaatt cctgggtaga aagtcagaca    6660
aatggtaagg tagaacatgc tttgtacata gtgagagttg gttcacccta atactgagaa    6720
cctggatata gctcagccag cgtgctttgc gttcaagctt accagagctg ttgtatgcct    6780
gttaagcagg gcatacagtc atgaggctct tgaaaaatct taacagacaa agggcaatgg    6840
aaaatcggag ttaagggatg gtagggataa aatgcataga aagaggtacc acgattttga    6900
tttttgccct aatgcctctc tgcgtggttc ctcaattttt ctacttcatt cctcatctcc    6960
tcagagcatt ccttcctc atgcttgaaa cacagatgaa agactgtgaa ttctaactga    7020
gatgaaaaca tccacaacca cacaacctct ggtgtggagt cacattctgt gaaggcaaaa    7080
actaggccac gtaatctatg tgtgcaagct acgtgtaagc tatgtgtgtg acaggacaat    7140
```

```
gtgaggaaca tactatgtgc acaaggactg cagaataaac aggagcaaag tttttgaaga   7200
aaacagagta aaatcccgtt ttcctctttt gttacattct ttacatatat ctcaaatttc   7260
ctctttggtt agaagcaagt aatatttatg tttcttggta ctgtttgggt tgaagaccat   7320
tctgggataa gagaaattcc agtggttctt cccctaatca taaaatgtac aggtttagtt   7380
tttttgtaac acagaaatct cttcatcttt tatcttttgt tgtgattctt tatagagaga   7440
gaaacaagac ttactgacaa tagcagcaag aaaatcaatc ttggaagaac aagattgcag   7500
ttgcaaaaac aaaccaatgt ccttgcccct acatcctctt ccccataaat tctacattct   7560
ctatctacct tgtgcttgcc aacatgatat acgtaaactc tcttttccta ttcattctta   7620
aaggaattat cagaaatgtc cttcagccaa gctccgtgga ttctcaaact gcaatggttc   7680
tggttaatgc cattgtcttc aaaggactgt gggagaaagc atttaaggat gaagacacac   7740
aagcaatgcc tttcagagtg actgaggtat atgggcatac cttagagatg taatctagaa   7800
tttatgaaga gagtagacat gttgttatat gaacactgca ttagcgtatc tgctcatttg   7860
tctgcatctc tttcagacac tgtgttaaaa gcagggaatt ttccttatgt ctctttcatc   7920
acaatattcc tgacattgca aagctcctga gaaataactt cagattccca cttttcctag   7980
ggaggtcttc ctggatgaga acaatcaatc atcttaactg taactagata tttctgcatc   8040
taagaataat ctttgttaaa actatattct ctctctcttt ttttttttt  ttggttctcc   8100 agcaagaaag caaacctgtg cagatgatgt ggatcc                             8136
```

<210> SEQ ID NO 14
<211> LENGTH: 27
<212> TYPE: DNA
<213> ORGANISM: Artificial Sequence
<220> FEATURE:
<223> OTHER INFORMATION: primer

<400> SEQUENCE: 14
gctgtagtgg agaagcacaa caggaga    27

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
ctctttctgc agactgacat gcatt    25

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
atttggagga gacacttgtt ggtcat    26

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17

-continued acctgtggtg tagacatcca gca                                    23

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
caacctcccc ttctacgagc ggct                                   24

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
aggacccagt gggacaaatc ta                                     22

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
accgaaagga gcgcacgacc ccat                                   24

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
caacttctag ggccatacct gct                                    23

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
aaaattccat gcttgctgca ccgat                                  25

<210> SEQ ID NO 23
<211> LENGTH: 1693
<212> TYPE: DNA
<213> ORGANISM: Artificial Sequence
<220> FEATURE:
<223> OTHER INFORMATION: SV40Pe-Neor

<400> SEQUENCE: 23
ttcaaatatg tatccgctca tgagacaata accctgataa atgcttcaat aatattgaaa      60
aaggaagagt cctgaggcgg aaagaaccag ctgtggaatg tgtgtcagtt agggtgtgga     120
aagtccccag gctccccagc aggcagaagt atgcaaagca tgcatctcaa ttagtcagca     180

```
accaggtgtg gaaagtcccc aggctccca gcaggcagaa gtatgcaaag catgcatctc      240
aattagtcag caaccatagt cccgcccta actccgccca tcccgcccct aactccgccc      300
agttccgccc attctccgcc ccatggctga ctaattttt ttatttatgc agaggccgag      360
gccgcctcgg cctctgagct attccagaag tagtgaggag gctttttgg aggcctaggc      420 ttttgcaaag atcgatcaag agacaggatg aggatcgttt cgcatgattg aacaagatgg      480
attgcacgca ggttctccgg ccgcttgggt ggagaggcta ttcggctatg actgggcaca      540
acagacaatc ggctgctctg atgccgccgt gttccggctg tcagcgcagg ggcgcccggt      600 tcttttgtc aagaccgacc tgtccggtgc cctgaatgaa ctgcaagacg aggcagcgcg      660
gctatcgtgg ctggccacga cgggcgttcc ttgcgcagct gtgctcgacg ttgtcactga      720
agcgggaagg gactggctgc tattgggcga agtgccgggg caggatctcc tgtcatctca      780
ccttgctcct gccgagaaag tatccatcat ggctgatgca atgcggcggc tgcatacgct      840
tgatccggct acctgcccat tcgaccacca agcgaaacat cgcatcgagc gagcacgtac      900
tcggatggaa gccggtcttg tcgatcagga tgatctggac gaagagcatc aggggctcgc      960
gccagccgaa ctgttcgcca ggctcaaggc gagcatgccc gacggcgagg atctcgtcgt     1020
gacccatggc gatgcctgct tgccgaatat catggtggaa aatggccgct ttctggatt      1080 catcgactgt ggccggctgg gtgtggcgga ccgctatcag acatagcgt tggctacccg      1140 tgatattgct gaagagcttg gcggcgaatg ggctgaccgc ttcctcgtgc tttacggtat     1200
cgccgctccc gattcgcagc gcatcgcctt ctatcgcctt cttgacgagt cttctgagc      1260 gggactctgg ggttcgaaat gaccgaccaa gcgacgccca acctgccatc acgagatttc     1320
gattccaccg ccgccttcta tgaaaggttg gcttcggaa tcgttttccg gacgccggc      1380 tggatgatcc tccagcgcgg ggatctcatg ctggagttct cgcccacccc tagggggagg     1440
ctaactgaaa cacggaagga gacaataccg gaaggaaccc gcgctatgac ggcaataaaa     1500
agacagaata aaacgcacgg tgttgggtcg tttgttcata acgcggggt tcggtcccag     1560 ggctggcact ctgtcgatac cccaccgaga ccccattggg gccaatacgc ccgcgtttct     1620
tccttttccc cacccaccc cccaagttcg ggtgaaggcc cagggctcgc agccaacgtc     1680
ggggcggcag gcc                                                        1693

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
agttcaccat gggctccatc gg                                                22

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
caccgagttc accatgggct ccat                                              24

<210> SEQ ID NO 26
<211> LENGTH: 24
```

```
<212> TYPE: DNA
<213> ORGANISM: Artificial Sequence
<220> FEATURE:
<223> OTHER INFORMATION: primer

<400> SEQUENCE: 26
aaacatggag cccatggtga actc                                          24

<210> SEQ ID NO 27
<211> LENGTH: 9735
<212> TYPE: DNA
<213> ORGANISM: human

<400> SEQUENCE: 27
```

| | | | | | |
|---|---|---|---|---|---|
| gtcgaccttm | agtcctcaga | cttggcaagg | agaatgtaga | tttctacagt atatatgttt | 60 |
| tcacaaaagg | aaggagagaa | acaaaagaaa | atggcactga | ctaaacttca gctagtggta | 120 |
| taggaaagta | attctgctta | acagagattg | cagtgatctc | tatgtatgtc ctgaagaatt | 180 |
| atgttgtact | tttttccctc | attttttaaat | caaacagtgc | tttacagagg tcagaatggt | 240 |
| ttctttactg | tttgtcaatt | ctattatttc | aatacagaac | aatagcttct ataactgaaa | 300 |
| tatatttgct | attgtatatt | atgattgtcc | ctcgaaccat | gaacactcct ccagctgaat | 360 |
| ttcacaattc | ctctgtcatc | tgccaggcca | ttaagttatt | catggaagat ctttgaggaa | 420 |
| cactgcaagt | tcatatcata | aacacatttg | aaattgagta | ttgttttgca ttgtatggag | 480 |
| ctatgttttg | ctgtatcctc | agaaaaaaag | tttgttataa | agcattcaca cccataaaaa | 540 |
| gatagattta | atattccag | ctataggaaa | gaaagtgcgt | ctgctcttca ctctagtctc | 600 |
| agttggctcc | ttcacatgca | cgcttcttta | tttctcctat | tttgtcaaga aaataatagg | 660 |
| tcacgtcttg | ttctcactta | tgtcctgcct | agcatggctc | agatgcacgt tgtacataca | 720 |
| agaaggatca | aatgaaacag | acttctggtc | tgttactaca | accatagtaa taagcacact | 780 |
| aactaataat | tgctaattat | gttttccatc | tccaaggttc | ccacattttt ctgttttctt | 840 |
| aaagatccca | ttatctggtt | gtaactgaag | ctcaatggaa | catgagcaat atttcccagt | 900 |
| cttctctccc | atccaacagt | cctgatggat | tagcagaaca | ggcagaaaac acattgttac | 960 |
| ccagaattaa | aaactaatat | ttgctctcca | ttcaatccaa | aatggaccta ttgaaactaa | 1020 |
| aatctaaccc | aatcccatta | aatgatttct | atggcgtcaa | aggtcaaact tctgaaggga | 1080 |
| acctgtgggt | gggtcacaat | tcaggctata | tattccccag | ggctcagcca gtgtctgtac | 1140 |
| atacagctag | aaagctgtat | tgcctttagc | actcaagctc | aaaaggtaag caactctctg | 1200 |
| gaattacctt | ctctctatat | tagctcttac | ttgcacctaa | actttaaaaa attaacaatt | 1260 |
| attgtgttat | gtgttgtatc | tttaagggtg | aagtacctgc | gtgataccc ctataaaaac | 1320 |
| ttctcacctg | tgtatgcatt | ctgcactatt | ttattatgtg | taaaagcttt gtgtttgttt | 1380 |
| tcaggaggct | tattctttgt | gcttaaaata | tgttttaat | ttcagaacat cttatcctgt | 1440 |
| cgttcactat | ctgatatgct | ttgcagtttg | cctgattaac | ttctagccct acagagtgca | 1500 |
| cagagagcaa | aatcatggtg | ttcagtgaat | tctggggagt | tatttaatg tgaaaattct | 1560 |
| ctagaagttt | aattcctgca | aagtgcagct | gctgatcact | acacaagata aaaatgtggg | 1620 |
| gggtgcataa | acgtatattc | ttacaataat | agatacatgt | gaacttgtat acagaaaaga | 1680 |
| aaatgagaaa | aatgtgtgtg | cgtatactca | cacacgtggt | cagtaaaaac ttttgagggg | 1740 |
| tttaatacag | aaaatccaat | cctgaggccc | cagcactcag | tacgcatata aagggctggg | 1800 |
| ctctgaagga | cttctgactt | tcacagatta | tataaatctc | aggaaagcaa ctagattcat | 1860 |

```
gctggctcca aaagctgtgc tttatataag cacactggct atacaatagt tgtacagttc    1920
agctctttat aatagaaaca gacagaacaa gtataaatct tctattggtc tatgtcatga    1980
acaagaattc attcagtggc tctgttttat agtaaacatt gctattttat catgtctgca    2040
tttctcttct gtctgaatgt caccactaaa atttaactcc acagaaagtt tatactacag    2100
tacacatgca tatctttgag caaagcaaac catacctgaa agtgcaatag agcagaatat    2160
gaattacatg cgtgtctttc tcctagacta catgaccca tataaattac attccttatc    2220
tattctgcca tcaccaaaac aaaggtaaaa atactttga agatctactc atagcaagta    2280
gtgtgcaaca aacagatatt tctctacatt tattttagg gaataaaaat aagaaataaa    2340
atagtcagca agcctctgct ttctcatata tctgtccaaa cctaaagttt actgaaattt    2400
gctctttgaa tttccagttt tgcaagccta tcagattgtg ttttaatcag aggtactgaa    2460
aagtatcaat gaattctagc tttcactgaa caaaaatatg tagaggcaac tggcttctgg    2520
gacagtttgc tacccaaaag acaactgaat gcaaatacat aaatagattt atgaatatgg    2580
ttttgaacat gcacatgaga ggtggatata gcaacagaca cattaccaca gaattacttt    2640
aaaactactt gttaacattt aattgcctaa aaactgctcg taatttactg ttgtagccta    2700
ccatagagta ccctgcatgg tactatgtac agcattccat ccttacattt tcactgttct    2760
gctgtttgct ctagacaact cagagttcac catgaggtct ttgctaatct tggtgctttg    2820
cttcctgccc ctggctgctc tggggggaggt ccagctggtg gagtccggcg gagggctggt    2880
ccagcctgga ggcagcctga gactgagctg tgctgccagc gggttcaata tcaaggatac    2940
ctacatccac tgggtgaggc aggcccccgg aaagggcctg gaatgggtgg ccaggattta    3000
cccaactaat gggtatactc ggtacgccga ttccgtcaaa ggcagattta ccattagcgc    3060
agacaccagc aaaaacacag catacctgca gatgaactcc ctgagagctg aagacacagc    3120
tgtgtattat tgctcccggt gggggggcga cggcttttat gccatggact actggggcca    3180
gggaaccctg gtcaccgtct cctcagcctc caccaagggc ccatcggtct tccccctggc    3240
accctcctcc aagagcacct ctgggggcac agcagccctg ggctgcctgg tcaaggacta    3300
cttccccgaa ccggtgacgg tgtcgtggaa ctcaggcgcc ctgaccagcg gcgtgcacac    3360
cttcccggct gtcctacagt cctcaggact ctactccctc agcagcgtgg tgaccgtgcc    3420
ctccagcagc ttgggcaccc agacctacat ctgcaacgtg aatcacaagc ccagcaacac    3480
caaggtggac aagaaagttg agcccaaatc ttgtgacaaa actcacacat gcccaccgtg    3540
cccagcacct gaactcctgg ggggaccgtc agtcttcctc ttccccccaa acccaaggac    3600
accctcatg atctcccgga cccctgaggt cacatgcgtg gtggtggacg tgagccacga    3660
agaccctgag gtcaagttca actggtacgt ggacggcgtg gaggtgcata atgccaagac    3720
aaagccgcgg gaggagcagt acaacagcac gtaccgtgtg gtcagcgtcc tcaccgtcct    3780
gcaccaggac tggctgaatg gcaaggagta caagtgcaag gtctccaaca aagccctccc    3840
agcccccatc gagaaaacca tctccaaagc caaagggcag cccgagaac acaggtgta    3900
caccctgccc ccatcccggg atgagctgac caagaaccag gtcagcctga cctgcctggt    3960
caaaggcttc tatcccagcg acatcgccgt ggagtgggag agcaatgggc agccggagaa    4020
caactacaag accacgcctc ccgtgctgga ctccgacggc tccttcttcc tctacagcaa    4080
gctcaccgtg gacaagagca ggtggcagca ggggaacgtc ttctcatgct ccgtgatgca    4140
tgaggctctg cacaaccact acacgcagaa gagcctctcc ctgtctccgg gtaaacgggc    4200
caagagagcc cccgtgaagc agaccctgaa cttcgacctg ctgaagctgg ccggcgacgt    4260
```

```
ggagtccaac cccggcccca tgcgctccct cttgattctc gtcttgtgtt ttttgccact    4320
ggccgctctc ggcgacatac agatgaccca gagcccctct tctctctcag catcagtcgg    4380
cgacagggtc acaattacct gccgggctag ccaagatgtg aacacagccg tggcttggta    4440
tcagcagaaa cctgggaagg ccccaaaact gctgatttat tctgctagct tcctgtattc    4500
tggggtgcct tccagattct ccggatccag atccggcact gatttcacac tgaccatcag    4560
cagcctccag cccgaggatt ttgcaacata ctactgtcag caacactaca ctactcctcc    4620
aacctttggc caaggcacca aggttgaaat caagcgtacg gtggctgcac catctgtctt    4680
catcttcccg ccatctgatg agcagttgaa atctggaact gcctctgttg tgtgcctgct    4740
gaataacttc tatcccagag aggccaaagt acagtggaag gtggataacg ccctccaatc    4800
gggtaactcc caggagagtg tcacagagca ggacagcaag gacagcacct acagcctcag    4860
cagcaccctg acgctgagca aagcagacta cgagaaacac aaagtctacg cctgcgaagt    4920
cacccatcag ggcctgagct cgcccgtcac aaagagcttc aacaggggag agtgttagtc    4980
gactcgctga tcagcctcga cttttgcctt c tagttgccag ccatctgttg tttgcccctc    5040
ccccgtgcct tccttgaccc tggaaggtgc cactcccact gtccttttcct aataaaatga    5100 ggaaattgca tcgcattgtc tgagtaggtg tcattctatt ctgggggggtg gggtggggca    5160 ggacagcaag ggggaggatt gggaagacaa tagcaggcac tcgaccctcg acctcgaaat    5220
tctaccgggt aggggaggcg ctttt cccaa ggcagtctgg agcatgcgct ttagcagccc    5280
cgctgggcac ttggcgctac acaagtggcc tctggcctcg cacacattcc acatccaccg    5340
gtaggcgcca accggctccg ttctttggtg gccccttcgc gccaccttct actcctcccc    5400
tagtcaggaa gttcccccccc gccccgcagc tcgcgtcgtg caggacgtga caaatggaag    5460
tagcacgtct cactagtctc gtgcagatgg acagcaccgc tgagcaatgg aagcgggtag    5520
gcctttgggg gcagcggccaa tagcagcttt gctccttcgc tttctgggct cagaggctgg    5580
gaaggggtgg gtccgggggc gggctcaggg gcgggctcag gggcggggcg ggcgcccgaa    5640
ggtcctccgg aggccccggca ttctgcacgc ttcaaaagcg cacgtctgcc gcgctgttct    5700
cctcttcctc atctccgggc cttt cgacct gcatccatct agatctagat cagcttacca    5760
tgaccgagta caagcccacg gtgcgcctcg ccacccgcga cgacgtcccc agggccgtac    5820
gcaccctcgc cgccgcgttc gccgactacc ccgccacgcg ccacaccgtc gatccggacc    5880
gccacatcga gcgggtcacc gagctgcaag aactcttcct cacgcgcgtc gggctcgaca    5940
tcggcaaggt gtgggtcgcg gacgacgggc ccgcggtggc ggtctggacc acgcggaga    6000 gcgtcgaagc gggggcggtg ttcgccgaga tcggcccgcg catggccgag ttgagcggtt    6060
cccggctggc cgcgcagcaa cagatggaag gcctcctggc gccgcaccgg cccaaggagc    6120
ccgcgtggtt cctggccacc gtcggcgtct cgcccgacca ccagggcaag gtctgggca    6180 gcgccgtcgt gctccccgga gtggaggcgg ccgagcgcgc cggggtgccc gccttcctgg    6240
agacctccgc gccccgcaac ctccccttct acgagcggct cggcttcacc gtcaccgccg    6300
acgtcgaggt gcccgaagga ccgcgcacct ggtgcatgac ccgcaagccc ggtgcctgac    6360
gcccgcccca cgacccgcag cgcccgaccg aaaggagcgc acgaccccat gcatcgatga    6420
tgccaataaa gatatcattg atgagtttgg acaaaccaca actagaatgc agtgaaaaaa    6480
atgctttatt tgtgaaattt gtgatgctat tgctttattt gtaaccatta taagctgcat    6540
atcgaattcc cgcggccgcg ggaattcgat tccatcggtg cagcaagcat ggaattttgt    6600
```

```
tttgatgtat tcaaggagct caaagtccac catgccaatg agaacatctt ctactgcccc    6660
attgccatca tgtcagctct agccatggta tacctgggtg caaaagacag caccaggaca    6720
cagataaata aggtgagcct acagttaaag attaaaacct ttgccctgct caatggagcc    6780
acagcactta attgtatgat aatgtcccTt ggaaactgca tagctcagag gctgaaaatc    6840
tgaaaccaga gttatctaaa agtgtggcca cctccaactc ccagagtgtt acccaaatgc    6900
actagctaga aatcttgaaa ctggattgca taacttcttt ttgtcataac cattatttca    6960
gctactatta ttttcaatta caggttgttc gctttgataa acttccagga ttcggagaca    7020
gtattgaagc tcaggtacag aaataatttc acctccttct ctatgtccct ttcctctgga    7080
agcaaaatac agcagatgaa gcaatctctt agctgttcca agccctctct gatgagcagc    7140
tagtgctctg catccagcag ttgggagaac actgttcata agaacagaga aaagaagga    7200
agtaacaggg gattcagaac aaacagaaga taaaactcag gacaaaaata ccgtgtgaat    7260
gaggaaactt gtggatattt gtacgcttaa gcaagacagc tagatgattc tggataaatg    7320
ggtctggttg gaaaagaagg aaagcctggc tgatctgctg gagctagatt attgcagcag    7380
gtaggcagga gttccctaga gaaaagtatg agggaattac agaagaaaaa cagcacaaaa    7440
ttgtaaatat tggaaaagga ccacatcagt gtagttacta gcagtaagac agacaggatg    7500
aaaaatagtt ttgtaaacag aagtatctaa ctactttact ctgttcatac actatgtaaa    7560
acctactaag taataaaact agaataacaa catctttctt tctctttgta ttcagtgtgg    7620
cacatctgta aacgttcact cttcacttag agacatcctc aaccaaatca ccaaaccaaa    7680
tgatgtttat tcgttcagcc ttgccagtag actttatgct gaagagagat acccaatcct    7740
gccagtaagt tgctctaaaa tctgatctga gtgtatttcc atgccaaagc tctaccattc    7800
tgtaatgcaa aaacagtcag agttccacat gtttcactaa gaaaatttct ttttctcttg    7860
ttttttacaaa tgaaagagag gacaaataac atttctctat caccgacctg aaactctaca    7920
gtcttcagag aatgaatggc ttgctaaaag aatgtcaaat cttaccatac agctatttca    7980
tattacacta ctaaatacac tataaggcat agcatgtagt aatacactgt aaaatagctt    8040
tttacactac tatattatta atatctgtta attccagtct tgcatttcac atttgcaaaa    8100
cgttttgaaa ttcgtatctg aaagctgaat actcttgctt tacaggaata cttgcagtgt    8160
gtgaaggaac tgtatagagg aggcttggaa cctatcaact ttcaaacagc tgcagatcaa    8220
gccagagagc tcatcaattc ctgggtagaa agtcagacaa atggtaaggt gaacatgct    8280
ttgtacatag tgagagttgg ttcaccctaa tactgagaac ctggatatag ctcagccagc    8340
gtgctttgcg ttcaagctta ccagagctgt tgtatgcctg ttaagcaggg catacagtca    8400
tgaggctctt gaaaatcttt aacagacaaa gggcaatgga aaatcggagt taagggatgg    8460
tagggataaa atgcatagaa agaggtacca cgattttgat ttttgcccta atgcctctct    8520
gcgtggttcc tcaattttc tacttcattc ctcatctcct cagagcattc ctttccctca    8580
tgcttgaaac acagatgaaa gactgtgaat tctaactgag atgaaaacat ccacaaccac    8640
acaacctctg gtgtggagtc acattctgtg aaggcaaaaa ctaggccacg taatctatgt    8700
gtgcaagcta cgtgtaagct atgtgtgtga caggacaatg tgaggaacat actatgtgca    8760
caaggactgc agaataaaca ggagcaaagt ttttgaagaa aacagagtaa aatcccgttt    8820
tcctcttttg ttacattctt tacatatatc tcaaatttcc tctttggtta gaagcaagta    8880
atatttatgt ttcttggtac tgtttgggtt gaagaccatt ctgggataag agaaattcca    8940
gtggttcttc ccctaatcat aaaatgtaca ggtttagttt ttttgtaaca cagaaatctc    9000
```

```
ttcatcttt  atcttttgtt  gtgattcttt  atagagagag  aaacaagact  tactgacaat      9060
agcagcaaga  aaatcaatct  tggaagaaca  agattgcagt  tgcaaaaaca  aaccaatgtc      9120 cttgcccta  catcctcttc  cccataaatt  ctacattctc  tatctacctt  gtgcttgcca      9180
acatgatata  cgtaaactct  cttttcctat  tcattcttaa  aggaattatc  agaaatgtcc      9240
ttcagccaag  ctccgtggat  tctcaaactg  caatggttct  ggttaatgcc  attgtcttca      9300
aaggactgtg  ggagaaagca  tttaaggatg  aagacacaca  agcaatgcct  ttcagagtga      9360
ctgaggtata  tgggcatacc  ttagagatgt  aatctagaat  ttatgaagag  agtagacatg      9420
ttgttatatg  aacactgcat  tagcgtatct  gctcatttgt  ctgcatctct  ttcagacact      9480
gtgttaaaag  cagggaattt  tccttatgtc  tctttcatca  caatattcct  gacattgcaa      9540
agctcctgag  aaataacttc  agattcccac  ttttcctagg  gaggtcttcc  tggatgagaa      9600
caatcaatca  tcttaactgt  aactagatat  ttctgcatct  aagaataatc  tttgttaaaa      9660
ctatattctc  tctctctttt  tttttttttt  tggttctcca  gcaagaaagc  aaacctgtgc      9720
agatgatgtg  gatcc                                                          9735
```

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28

```
ccccagagca gccaggggca ggaagcaaag                                             30
```

<210> SEQ ID NO 29
<211> LENGTH: 28
<212> TYPE: DNA
<213> ORGANISM: Artificial Sequence
<220> FEATURE:
<223> OTHER INFORMATION: primer

<400> SEQUENCE: 29

```
aaagcaccaa gattagcaaa gacctcat                                               28
```

<210> SEQ ID NO 30
<211> LENGTH: 10104
<212> TYPE: DNA
<213> ORGANISM: human

<400> SEQUENCE: 30

```
gtcgaccta  agtcctcaga  cttggcaagg  agaatgtaga  tttctacagt  atatatgttt        60
tcacaaaagg  aaggagagaa  acaaaagaaa  atggcactga  ctaaacttca  gctagtggta       120
taggaaagta  attctgctta  acagagattg  cagtgatctc  tatgtatgtc  ctgaagaatt       180
atgttgtact  ttttccctc   attttaaat   caaacagtgc  tttacagagg  tcagaatggt       240
ttctttactg  tttgtcaatt  ctattattc   aatacagaac  aatagcttct  ataactgaaa       300
tatatttgct  attgtatatt  atgattgtcc  ctcgaaccat  gaacactcct  ccagctgaat       360
ttcacaattc  ctctgtcatc  tgccaggcca  ttaagttatt  catggaagat  ctttgaggaa       420
cactgcaagt  tcatatcata  aacacatttg  aaattgagta  ttgttttgca  ttgtatggag       480
ctatgttttg  ctgtatcctc  agaaaaaaag  tttgttataa  agcattcaca  cccataaaaa       540
gatagattta  atattccag   ctataggaaa  gaaagtgcgt  ctgctcttca  ctctagtctc       600
```

```
agttggctcc ttcacatgca cgcttcttta tttctcctat tttgtcaaga aaataatagg    660
tcacgtcttg ttctcactta tgtcctgcct agcatggctc agatgcacgt tgtacataca    720
agaaggatca aatgaaacag acttctggtc tgttactaca accatagtaa taagcacact    780
aactaataat tgctaattat gttttccatc tccaaggttc ccacatttttt ctgttttctt    840 aaagatccca ttatctggtt gtaactgaag ctcaatggaa catgagcaat atttcccagt    900
cttctctccc atccaacagt cctgatggat tagcagaaca ggcagaaaac acattgttac    960
ccagaattaa aaactaatat tgctctccca ttcaatccaa aatggaccta ttgaaactaa   1020
aatctaaccc aatcccatta aatgatttct atggcgtcaa aggtcaaact tctgaaggga   1080
acctgtgggt gggtcacaat tcaggctata tattccccag ggctcagcca gtgtctgtac   1140
atacagctag aaagctgtat tgcctttagc actcaagctc aaaaggtaag caactctctg   1200
gaattacctt ctctctatat tagctcttac ttgcacctaa actttaaaaa attaacaatt   1260
attgtgttat gtgttgtatc tttaagggtg aagtacctgc gtgataccccc ctataaaaac   1320 ttctcacctg tgtatgcatt ctgcactatt ttattatgtg taaaagcttt gtgtttgttt   1380
tcaggaggct tattctttgt gcttaaaata tgttttttaat ttcagaacat cttatcctgt   1440
cgttcactat ctgatatgct ttgcagtttg cctgattaac ttctagccct acagagtgca   1500
cagagagcaa aatcatggtg ttcagtgaat tctggggagt tattttaatg tgaaaattct   1560
ctagaagttt aattcctgca aagtgcagct gctgatcact acacaagata aaaatgtggg   1620
gggtgcataa acgtatattc ttacaataat agatacatgt gaacttgtat acagaaaaga   1680
aaatgagaaa aatgtgtgtg cgtatactca cacacgtggt cagtaaaaac ttttgagggg   1740
tttaatacag aaaatccaat cctgaggccc cagcactcag tacgcatata aagggctggg   1800
ctctgaagga cttctgactt tcacagatta tataaatctc aggaaagcaa ctagattcat   1860
gctggctcca aaagctgtgc tttatataag cacactggct atacaatagt tgtacagttc   1920
agctctttat aatagaaaca gacagaacaa gtataaatct tctattggtc tatgtcatga   1980
acaagaattc attcagtggc tctgttttat agtaaacatt gctattttat catgtctgca   2040
tttctcttct gtctgaatgt caccactaaa atttaactcc acagaaagtt tatactacag   2100
tacacatgca tatctttgag caaagcaaac catacctgaa agtgcaatag agcagaatat   2160
gaattacatg cgtgtctttc tcctagacta catgaccccca tataaattac attccttatc   2220
tattctgcca tcaccaaaac aaaggtaaaa atactttga agatctactc atagcaagta   2280
gtgtgcaaca aacagatatt tctctacatt tattttagg gaataaaaat aagaaataaa   2340
atagtcagca agcctctgct ttctcatata tctgtccaaa cctaaagttt actgaaattt   2400 gctcttttgaa tttccagttt tgcaagccta tcagattgtg ttttaatcag aggtactgaa   2460
aagtatcaat gaattctagc tttcactgaa caaaaatatg tagaggcaac tggcttctgg   2520
gacagtttgc tacccaaaag acaactgaat gcaaatacat aaatagattt atgaatatgg   2580
ttttgaacat gcacatgaga ggtggatata gcaacagaca cattaccaca gaattacttt   2640
aaaactactt gttaacattt aattgcctaa aaactgctcg taatttactg ttgtagccta   2700
ccatagagta ccctgcatgg tactatgtac agcattccat ccttacattt tcactgttct   2760
gctgtttgct ctagacaact cagagttcac catgaggtct ttgctaatct tggtgctttg   2820
cttcctgccc ctggctgctc tgggggaggt ccagctggtg gagtccggcg gagggctggt   2880
ccagcctgga ggcagcctga gactgagctg tgctgccagc gggttcaata tcaaggatac   2940
ctacatccac tgggtgaggc aggcccccgg aaagggcctg gaatgggtgg ccaggattta   3000
```

```
cccaactaat gggtatactc ggtacgccga ttccgtcaaa ggcagattta ccattagcgc   3060
agacaccagc aaaaacacag catacctgca gatgaactcc ctgagagctg aagacacagc   3120
tgtgtattat tgctcccggt ggggggggcga cggcttttat gccatggact actggggcca   3180
gggaaccctg gtcaccgtct cctcagcctc caccaagggc ccatcggtct tccccctggc   3240
accctcctcc aagagcacct ctgggggcac agcagccctg gctgcctgg tcaaggacta   3300 cttccccgaa ccggtgacgg tgtcgtgaa ctcaggcgcc ctgaccagcg gcgtgcacac   3360
cttcccggct gtcctacagt cctcaggact ctactccctc agcagcgtgg tgaccgtgcc   3420
ctccagcagc ttgggcaccc agacctacat ctgcaacgtg aatcacaagc ccagcaacac   3480
caaggtggac aagaaagttg agcccaaatc ttgtgacaaa actcacacat gcccaccgtg   3540
cccagcacct gaactcctgg ggggaccgtc agtcttcctc ttccccccaa acccaaggac  3600
caccctcatg atctcccgga cccctgaggt cacatgcgtg gtggtggacg tgagccacga   3660
agaccctgag gtcaagttca actggtacgt ggacggcgtg gaggtgcata atgccaagac   3720
aaagccgcgg gaggagcagt acaacagcac gtaccgtgtg gtcagcgtcc tcaccgtcct   3780
gcaccaggac tggctgaatg gcaaggagta caagtgcaag gtctccaaca aagccctccc   3840
agcccccatc gagaaaacca tctccaaagc caaagggcag ccccgagaac acaggtgta   3900 caccctgccc ccatcccggg atgagctgac caagaaccag gtcagcctga cctgcctggt   3960
caaaggcttc tatcccagcg acatcgccgt ggagtgggag agcaatgggc agccggagaa   4020
caactacaag accacgcctc ccgtgctgga ctccgacggc tccttcttcc tctacagcaa   4080
gctcaccgtg gacaagagca ggtggcagca ggggaacgtc ttctcatgct ccgtgatgca   4140
tgaggctctg cacaaccact acacgcagaa gagcctctcc ctgtctccgg gtaaacgggc   4200
caagagagcc ccgtgaagc agaccctgaa cttcgacctg ctgaagctgg ccggcgacgt   4260
ggagtccaac cccggcccca tgcgctccct cttgattctc gtcttgtgtt ttttgccact   4320
ggccgctctc ggcgacatac agatgaccca gagcccctct tctctctcag catcagtcgg   4380
cgacagggtc acaattacct gccgggctag ccaagatgtg aacacagccg tggcttggta   4440
tcagcagaaa cctgggaagg ccccaaaact gctgatttat tctgctagct tcctgtattc   4500
tggggtgcct tccagattct ccggatccag atccggcact gatttcacac tgaccatcag   4560
cagcctccag cccgaggatt ttgcaacata ctactgtcag caacactaca ctactcctcc   4620
aacctttggc caaggcacca aggttgaaat caagcgtacg gtggctgcac catctgtctt   4680
catcttcccg ccatctgatg agcagttgaa atctggaact gcctctgttg tgtgcctgct   4740
gaataacttc tatcccagag aggccaaagt acagtggaag gtggataacg ccctccaatc   4800
gggtaactcc caggagagtg tcacagagca ggacagcaag gacagcacct acagcctcag   4860
cagcaccctg acgctgagca aagcagacta cgagaaacac aaagtctacg cctgcgaagt   4920
cacccatcag ggcctgagct cgcccgtcac aaagagcttc aacaggggag agtgttagtc   4980
gactcgctga tcagcctcga ctttgccttc tagttgccag ccatctgttg tttgcccctc   5040
ccccgtgcct tccttgaccc tggaaggtgc cactcccact gtcctttcct aataaaatga   5100
ggaaattgca tcgcattgtc tgagtaggtg tcattctatt ctggggggtg ggtggggca    5160 ggacagcaag gggaggatt gggaagacaa tagcaggcac tcgaccctcg acttcaaata   5220
tgtatccgct catgagacaa taaccctgat aaatgcttca ataatattga aaaggaaga   5280 gtcctgaggc ggaaagaacc agctgtggaa tgtgtgtcag ttagggtgtg gaaagtcccc   5340
```

```
aggctcccca gcaggcagaa gtatgcaaag catgcatctc aattagtcag caaccaggtg      5400
tggaaagtcc ccaggctccc cagcaggcag aagtatgcaa agcatgcatc tcaattagtc      5460
agcaaccata gtcccgcccc taactccgcc catcccgccc ctaactccgc ccagttccgc      5520
ccattctccg ccccatggct gactaatttt ttttatttat gcagaggccg aggccgcctc      5580
ggcctctgag ctattccaga agtagtgagg aggcttttt ggaggcctag cttttgcaa       5640 agatcgatca agagacagga tgaggatcgt ttcgcatgat tgaacaagat ggattgcacg      5700
caggttctcc ggccgcttgg gtggagaggc tattcggcta tgactgggca caacagacaa      5760
tcggctgctc tgatgccgcc gtgttccggc tgtcagcgca ggggcgcccg gttcttttg       5820 tcaagaccga cctgtccggt gccctgaatg aactgcaaga cgaggcagcg cggctatcgt      5880
ggctggccac gacgggcgtt ccttgcgcag ctgtgctcga cgttgtcact gaagcgggaa      5940
gggactggct gctattgggc gaagtgccgg ggcaggatct cctgtcatct caccttgctc      6000
ctgccgagaa agtatccatc atggctgatg caatgcggcg gctgcatacg cttgatccgg      6060
ctacctgccc attcgaccac caagcgaaac atcgcatcga gcgagcacgt actcggatgg      6120
aagccggtct tgtcgatcag gatgatctgg acgaagagca tcaggggctc gcgccagccg      6180
aactgttcgc caggctcaag gcgagcatgc ccgacggcga ggatctcgtc gtgacccatg      6240
gcgatgcctg cttgccgaat atcatggtgg aaaatggccg cttttctgga ttcatcgact      6300
gtggccggct gggtgtggcg gaccgctatc aggacatagc gttggctacc cgtgatattg      6360
ctgaagagct tggcggcgaa tgggctgacc gcttcctcgt gctttacggt atcgccgctc      6420
ccgattcgca gcgcatcgcc ttctatcgcc ttcttgacga gttcttctga gcgggactct      6480
ggggttcgaa atgaccgacc aagcgacgcc caacctgcca tcacgagatt tcgattccac      6540
cgccgccttc tatgaaaggt tgggcttcgg aatcgttttc cgggacgccg gctggatgat      6600
cctccagcgc ggggatctca tgctggagtt cttcgcccac cctaggggga gctaactga       6660 aacacggaag gagacaatac cggaaggaac ccgcgctatg acggcaataa aaagacagaa      6720
taaaacgcac ggtgttgggt cgtttgttca taaacgcggg gttcggtccc agggctggca      6780
ctctgtcgat accccaccga gaccccattg gggccaatac gcccgcgttt cttccttttc      6840 cccacccac ccccaagtt cgggtgaagg cccagggctc gcagccaacg tcgggcggc         6900 aggctgcata tcgaattccc gcggccgcgg gaattcgatt ccatcggtgc agcaagcatg      6960
gaattttgtt ttgatgtatt caaggagctc aaagtccacc atgccaatga aacatcttc       7020 tactgcccca ttgccatcat gtcagctcta gccatggtat acctgggtgc aaaagacagc      7080
accaggacac agataaataa ggtgagccta cagttaaaga ttaaaacctt tgccctgctc      7140
aatggagcca cagcacttaa ttgtatgata atgtcccttg gaaactgcat agctcagagg      7200
ctgaaaatct gaaaccagag ttatctaaaa gtgtggccac ctccaactcc cagagtgtta      7260
cccaaatgca ctagctagaa atcttgaaac tggattgcat aacttctttt tgtcataacc      7320
attatttcag ctactattat tttcaattac aggttgttcg ctttgataaa cttccaggat      7380
tcggagacag tattgaagct caggtacaga ataatttca cctccttctc tatgtcccctt      7440 tcctctggaa gcaaaataca gcagatgaag caatctctta gctgttccaa gccctctctg      7500
atgagcagct agtgctctgc atccagcagt tgggagaaca ctgttcataa gaacagagaa      7560
aaagaaggaa gtaacagggg attcagaaca aacagaagat aaaactcagg acaaaaatac      7620
cgtgtgaatg aggaaacttg tggatatttg tacgcttaag caagacagct agatgattct      7680
ggataaatgg gtctggttgg aaaagaagga aagcctggct gatctgctgg agctagatta      7740
```

-continued

```
ttgcagcagg taggcaggag ttccctagag aaaagtatga gggaattaca gaagaaaaac   7800
agcacaaaat tgtaaatatt ggaaaaggac cacatcagtg tagttactag cagtaagaca   7860
gacaggatga aaatagtttt tgtaaacaga agtatctaac tactttactc tgttcataca   7920
ctatgtaaaa cctactaagt aataaaacta gaataacaac atctttcttt ctctttgtat   7980
tcagtgtggc acatctgtaa acgttcactc ttcacttaga gacatcctca accaaatcac   8040
caaaccaaat gatgtttatt cgttcagcct tgccagtaga ctttatgctg aagagagata   8100
cccaatcctg ccagtaagtt gctctaaaat ctgatctgag tgtatttcca tgccaaagct   8160
ctaccattct gtaatgcaaa aacagtcaga gttccacatg tttcactaag aaaatttctt   8220
tttctcttgt ttttacaaat gaaagagagg acaaataaca tttctctatc accgacctga   8280
aactctacag tcttcagaga atgaatggct tgctaaaaga atgtcaaatc ttaccataca   8340
gctatttcat attacactac taaatacact ataaggcata gcatgtagta atacactgta   8400
aaatagcttt ttacactact atattattaa tatctgttaa ttccagtctt gcatttcaca   8460
tttgcaaaac gttttgaaat tcgtatctga aagctgaata ctcttgcttt acaggaatac   8520
ttgcagtgtg tgaaggaact gtatagagga ggcttggaac ctatcaactt tcaaacagct   8580
gcagatcaag ccagagagct catcaattcc tgggtagaaa gtcagacaaa tggtaaggta   8640
gaacatgctt tgtacatagt gagagttggt tcaccctaat actgagaacc tggatatagc   8700
tcagccagcg tgctttgcgt tcaagcttac cagagctgtt gtatgcctgt taagcagggc   8760
atacagtcat gaggctcttg aaaaatctta acagacaaag ggcaatggaa aatcggagtt   8820
aagggatggt agggataaaa tgcatagaaa gaggtaccac gattttgatt tttgccctaa   8880
tgcctctctg cgtggttcct caatttttct acttcattcc tcatctcctc agagcattcc   8940
tttccctcat gcttgaaaca cagatgaaag actgtgaatt ctaactgaga tgaaaacatc   9000
cacaaccaca caacctctgg tgtggagtca cattctgtga aggcaaaaac taggccacgt   9060
aatctatgtg tgcaagctac gtgtaagcta tgtgtgtgac aggacaatgt gaggaacata   9120
ctatgtgcac aaggactgca gaataaacag gagcaaagtt tttgaagaaa acagagtaaa   9180
atcccgtttt cctcttttgt tacattcttt acatatatct caaatttcct ctttggttag   9240
aagcaagtaa tatttatgtt tcttggtact gtttgggttg aagaccattc tgggataaga   9300
gaaattccag tggttcttcc cctaatcata aaatgtacag gtttagtttt tttgtaacac   9360
agaaatctct tcatcttttα tcttttgttg tgattcttta tagagagaga aacaagactt   9420
actgacaata gcagcaagaa aatcaatctt ggaagaacaa gattgcagtt gcaaaaacaa   9480
accaatgtcc ttgcccctac atcctcttcc ccataaattc tacattctct atctaccttg   9540
tgcttgccaa catgatatac gtaaactctc ttttcctatt cattcttaaa ggaattatca   9600
gaaatgtcct tcagccaagc tccgtggatt ctcaaactgc aatggttctg gttaatgcca   9660
ttgtcttcaa aggactgtgg gagaaagcat ttaaggatga agacacacaa gcaatgcctt   9720
tcagagtgac tgaggtatat gggcatacct tagagatgta atctagaatt tatgaagaga   9780
gtagacatgt tgttatatga acactgcatt agcgtatctg ctcatttgtc tgcatctctt   9840
tcagacactg tgttaaaagc agggaatttt cctatgtct ctttcatcac aatattcctg   9900
acattgcaaa gctcctgaga ataacttca gattcccact tttcctaggg aggtcttcct   9960
ggatgagaac aatcaatcat cttaactgta actagatatt tctgcatcta agaataatct  10020
ttgttaaaac tatattctct ctctcttttt tttttttttt ggttctccag caagaaagca  10080
```

```
aacctgtgca gatgatgtgg atcc                                        10104
```

<210> SEQ ID NO 31
<211> LENGTH: 16102
<212> TYPE: DNA
<213> ORGANISM: human

<400> SEQUENCE: 31

```
gtcgaccttt agtcctcaga cttggcaagg agaatgtaga tttctacagt atatatgttt    60
tcacaaaagg aaggagagaa acaaaagaaa atggcactga ctaaacttca gctagtggta   120
taggaaagta attctgctta acagagattg cagtgatctc tatgtatgtc ctgaagaatt   180
atgttgtact ttttcccctc atttttaaat caaacagtgc tttacagagg tcagaatggt   240
ttctttactg tttgtcaatt ctattatttc aatacagaac aatagcttct ataactgaaa   300
tatatttgct attgtatatt atgattgtcc ctcgaaccat gaacactcct ccagctgaat   360
ttcacaattc ctctgtcatc tgccaggcca ttaagttatt catggaagat ctttgaggaa   420
cactgcaagt tcatatcata aacacatttg aaattgagta ttgttttgca ttgtatggag   480
ctatgttttg ctgtatcctc agaaaaaaag tttgttataa agcattcaca cccataaaaa   540
gatagattta aatattccag ctataggaaa gaaagtgcgt ctgctcttca ctctagtctc   600
agttggctcc ttcacatgca cgcttcttta tttctcctat tttgtcaaga aaataatagg   660
tcacgtcttg ttctcactta tgtcctgcct agcatggctc agatgcacgt tgtacataca   720
agaaggatca aatgaaacag acttctggtc tgttactaca accatagtaa taagcacact   780
aactaataat tgctaattat gttttccatc tccaaggttc ccacattttt ctgttttctt   840
aaagatccca ttatctggtt gtaactgaag ctcaatggaa catgagcaat atttcccagt   900
cttctctccc atccaacagt cctgatggat tagcagaaca ggcagaaaac acattgttac   960
ccagaattaa aaactaatat ttgctctcca ttcaatccaa aatggaccta ttgaaactaa  1020
aatctaaccc aatcccatta aatgatttct atggcgtcaa aggtcaaact tctgaaggga  1080
acctgtgggt gggtcacaat tcaggctata tattccccag ggctcagcca gtgtctgtac  1140
atacagctag aaagctgtat tgcctttagc actcaagctc aaaaggtaag caactctctg  1200
gaattacctt ctctctatat tagctcttac ttgcacctaa actttaaaaa attaacaatt  1260
attgtgttat gtgttgtatc tttaagggtg aagtacctgc gtgatacccc ctataaaaac  1320
ttctcacctg tgtatgcatt ctgcactatt ttattatgtg taaaagcttt gtgtttgttt  1380
tcaggaggct tattctttgt gcttaaaata tgtttttaat ttcagaacat cttatcctgt  1440
cgttcactat ctgatatgct ttgcagtttg cctgattaac ttctagccct acagagtgca  1500
cagagagcaa aatcatggtg ttcagtgaat tctggggagt tattttaatg tgaaaattct  1560
ctagaagttt aattcctgca aagtgcagct gctgatcact acacaagata aaaatgtggg  1620
gggtgcataa acgtatattc ttacaataat agatacatgt gaacttgtat acagaaaaga  1680
aaatgagaaa aatgtgtgtg cgtatactca cacacgtggt cagtaaaaac ttttgagggg  1740
tttaatacag aaaatccaat cctgaggccc cagcactcag tacgcatata aagggctggg  1800
ctctgaagga cttctgactt tcacagatta tataaatctc aggaaagcaa ctagattcat  1860
gctggctcca aaagctgtgc tttatataag cacactggct atacaatagt tgtacagttc  1920
agctctttat aatagaaaca gacagaacaa gtataaatct tctattggtc tatgtcatga  1980
acaagaattc attcagtggc tctgttttat agtaaacatt gctatttat catgtctgca   2040
tttctcttct gtctgaatgt caccactaaa atttaactcc acagaaagtt tatactacag  2100
```

```
tacacatgca tatctttgag caaagcaaac catacctgaa agtgcaatag agcagaatat    2160
gaattacatg cgtgtctttc tcctagacta catgacccca tataaattac attccttatc    2220
tattctgcca tcaccaaaac aaaggtaaaa atactttga agatctactc atagcaagta     2280
gtgtgcaaca aacagatatt tctctacatt tattttagg gaataaaaat aagaaataaa     2340
atagtcagca agcctctgct ttctcatata tctgtccaaa cctaaagttt actgaatttt    2400
gctctttgaa tttccagttt tgcaagccta tcagattgtg ttttaatcag aggtactgaa    2460
aagtatcaat gaattctagc tttcactgaa caaaaatatg tagaggcaac tggcttctgg    2520
gacagtttgc tacccaaaag acaactgaat gcaaatacat aaatagattt atgaatatgg    2580
ttttgaacat gcacatgaga ggtggatata gcaacagaca cattaccaca gaattacttt    2640
aaaactactt gttaacattt aattgcctaa aaactgctcg taatttactg ttgtagccta    2700
ccatagagta ccctgcatgg tactatgtac agcattccat ccttacattt tcactgttct    2760
gctgtttgct ctagacaact cagagttcac catgaggtct ttgctaatct tggtgctttg    2820
cttcctgccc ctggctgctc tggggcaaga ggaaggccaa gtcgagggcc aagacgaaga    2880
catcccacca atcaccctgcg tacagaacgg cctcaggtac catgaccgag acgtgtggaa    2940
acccgagccc tgccggatct gcgtctgcga caacggcaag gtgttgtgcg atgacgtgat    3000
ctgtgacgag accaagaact gccccggcgc cgaagtcccc gagggcgagt gctgtcccgt    3060 ctgcccccgac ggctcagagt cacccaccga ccaagaaacc accggcgtcg agggacccaa    3120
gggagacact ggcccccgag gcccaagggg acccgcaggc ccccctggcc gagatggcat    3180
ccctggacag cctggacttc ccggaccccc cggaccccc ggacctcccg gacccctgg     3240 cctcggagga aactttgctc cccagctgtc ttatggctat gatgagaaat caaccggagg    3300
aatttccgtg cctggcccca tgggtccctc tggtcctcgt ggtctccctg gcccccctgg    3360
tgcacctggt ccccaaggct tccaaggtcc ccctggtgag cctggcgagc tggagcttc     3420 aggtcccatg ggtccccgag gtcccccagg tcccctggaa agaatggag atgatgggga    3480 agctggaaaa cctggtcgtc ctggtgagcg tgggcctcct gggcctcagg gtgctcgagg    3540
attgcccgga acagctggcc tcctggaat gaagggacac agaggtttca gtggtttgga    3600
tggtgccaag ggagatgctg gtcctgctgg tcctaagggt gagcctggca gccctggtga    3660
aaatggagct cctggtcaga tgggcccccg tggcctgcct ggtgagagag gtcgccctgg    3720
agcccctggc cctgctggtg ctcgtggaaa tgatggtgct actggtgctg ccgggccccc    3780
tggtcccacc ggccccgctg gtcctcctgg cttccctggt gctgttggtg ctaagggtga    3840
agctggtccc caagggccc gaggctctga aggtcccccag ggtgtgcgtg gtgagcctgg    3900 ccccctggc cctgctggtg ctgctggccc tgctggaaac cctggtgctg atggacagcc    3960
tggtgctaaa ggtgccaatg gtgctcctgg tattgctggt gctcctggtc ccctggtgc    4020 ccgaggcccc tctggacccc agggcccgg cggccctcct ggtcccaagg taacagcgg    4080 tgaacctggt gctcctggca gcaaaggaga cactggtgct aagggagagc tggccctgt    4140 tggtgttcaa ggaccccctg gccctgctgg agaggaagga aagcgaggag ctcgaggtga    4200
acccggaccc actggcctgc ccggaccccc tggcgagcgt ggtggacctg gtagccgtgg    4260
tttccctggc gcagatggtg ttgctggtcc caagggtccc gctggtgaac gtggttctcc    4320
tggccctgct ggccccaaag gatctcctgg tgaagctggt cgtccggtg aagctggtct    4380 gcctggtgcc aagggtctga ctggaagccc tggcagccct ggtcctgatg gcaaaactgg    4440
```

-continued

```
cccccctggt cccgccggtc aagatggtcg ccccggaccc ccaggcccac ctggtgcccg    4500
tggtcaggct ggtgtgatgg gattccctgg acctaaaggt gctgctggag agcccggcaa    4560
ggctggagag cgaggtgttc ccggacccccc tggcgctgtc ggtcctgctg gcaaagatgg   4620
agaggctgga gctcagggac cccctggccc tgctggtccc gctggcgaga gaggtgaaca    4680
aggccctgct ggctcccccg gattccaggg tctccctggt cctgctggtc ctccaggtga    4740
agcaggcaaa cctggtgaac agggtgttcc tggagacctt ggcgcccctg gcccctctgg    4800
agcaagaggc gagagaggtt tccctggcga gcgtggtgtg caaggtcccc ctggtcctgc    4860
tggtccccga ggggccaacg gtgctcccgg caacgatggt gctaagggtg atgctggtgc    4920
ccctggagct cccggtagcc agggcgcccc tggccttcag ggaatgcctg gtgaacgtgg    4980
tgcagctggt cttccagggc ctaagggtga cagaggtgat gctggtccca aggtgctga    5040 tggctctcct ggcaaagatg gcgtccgtgg tctgactggc cccattggtc ctcctggccc    5100
tgctggtgcc cctggtgaca agggtgaaag tggtcccagc ggccctgctg gtcccactgg    5160
agctcgtggt gcccccggag accgtggtga gcctggtccc ccggccctg ctggctttgc    5220 tggcccccct ggtgctgacg gccaacctgg tgctaaaggc gaacctggtg atgctggtgc    5280
taaaggcgat gctggtcccc ctggccctgc cggacccgct ggaccccctg gccccattgg    5340
taatgttggt gctcctggag ccaaaggtgc tcgcggcagc gctggtcccc ctggtgctac    5400
tggtttccct ggtgctgctg gccgagtcgg tcctcctggc ccctctggaa atgctggacc    5460
ccctggccct cctggtcctg ctggcaaaga aggcggcaaa ggtccccgtg gtgagactgg    5520
ccctgctgga cgtcctggtg aagttggtcc cctggtccc cctggccctg ctggcgagaa    5580
aggatcccct ggtgctgatg gtcctgctgg tgctcctggt actccgggc ctcaaggtat    5640 tgctggacag cgtggtgtgg tcggcctgcc tggtcagaga ggagagagag gcttccctgg    5700
tcttcctggc ccctctggtg aacctggcaa acaaggtccc tctggagcaa gtggtgaacg    5760 tggtcccccct ggtccatgg gccccctgg attggctgga cccccctggtg aatctggacg    5820 tgagggggct cctggtgccg aaggttcccc tggacgagac ggttctcctg gcgccaaggg    5880
tgaccgtggt gagaccggcc ccgctggacc cctggtgct cctggtgctc ctggtgcccc    5940
tggccccgtt ggccctgctg gcaagagtgg tgatcgtggt gagactggtc ctgctggtcc    6000
cgccggtcct gtcggccctg ttggcgcccg tggcccccgc ggaccccaag gccccgtgg    6060 tgacaagggt gagacaggcg aacagggcga cagaggcata aagggtcacc gtggcttctc    6120
tggcctccag ggtcccctg gcctcctgg ctctcctggt gaacaaggtc cctctggagc    6180
ctctggtcct gctggtcccc gaggtccccc tggctctgct ggtgctcctg gcaaagatgg    6240
actcaacggt ctccctggcc ccattgggcc cctggtcct cgcggtcgca ctggtgatgc    6300
tggtcctgtt ggtccccccg gccctcctgg acctcctggt ccccctggtc ctcccagcgc    6360
tggtttcgac ttcagcttcc tgccccagcc acctcaagag aaggctcacg atggtggccg    6420
ctactaccgg gctgatgatg ccaatgtggt tcgtgaccgt gacctcgagg tggacaccac    6480
cctcaagagc ctgagccagc agatcgagaa catccggagc cagagggca gccgcaagaa    6540 ccccgcccga acctgccgtg acctcaagat gtgccactct gactggaaga gtggagagta    6600
ctggattgac cccaaccaag gctgcaacct ggatgccatc aaagtcttct gcaacatgga    6660
gactggtgag acctgcgtgt accccactca gcccagtgtg gcccagaaga actggtacat    6720
cagcaagaac cccaaggaca gaggcatgt ctggttcggc gagagcatga ccgatggatt    6780
ccagttcgag tatggcggcc agggctccga ccctgccgat gtggccatcc agctgacctt    6840
```

```
cctgcgcctg atgtccaccg aggcctccca gaacatcacc taccactgca agaacagcgt    6900
ggcctacatg gaccagcaga ctggcaacct caagaaggcc ctgctcctcc agggctccaa    6960
cgagatcgag atccgcgccc agggcaacag ccgcttcacc tacagcgtca ctgtcgatgg    7020
ctgcacgagt cacaccggag cctggggcaa gacagtgatt gaatacaaaa ccaccaagac    7080
ctcccgcctg cccatcatcg atgtggcccc cttggacgtt ggtgcccag accaggaatt     7140 cggcttcgac gttggccctg tctgcttcct gcgggccaag agagccccg tgaagcagac      7200 cctgaacttc gacctgctga agctggccgg cgacgtggag tccaaccccg ccccatgcg     7260 ctccctcttg attctcgtct tgtgtttttt gccactggcc gctctcggcc aatctttaca    7320
agaggaaact gtaagaaagg gcccagccgg agatagagga ccacgtggag aaaggggtcc    7380
accaggcccc ccaggcagag atggtgaaga tggtcccaca ggccctcctg gtccacctgg    7440
tcctcctggc cccctggtc tcggtgggaa ctttgctgct cagtatgatg gaaaaggagt      7500
tggacttggc cctggaccaa tgggcttaat gggacctaga ggcccacctg gtgcagctgg    7560
agccccaggc cctcaaggtt tccaaggacc tgctggtgag cctggtgaac ctggtcaaac    7620
tggtcctgca ggtgctcgtg gtccagctgg ccctcctggc aaggctggtg aagatggtca    7680
ccctggaaaa cccggacgac ctggtgagag aggagttgtt ggaccacagg gtgctcgtgg    7740
tttccctgga actcctggac ttcctggctt caaaggcatt aggggacaca atggtctgga    7800
tggattgaag ggacagcccg tgctcctgg tgtgaagggt gaacctggtg ccctggtga      7860 aaatggaact ccaggtcaaa caggagcccg tgggcttcct ggtgagagag acgtgttgg     7920 tgcccctggc ccagctggtg cccgtggcag tgatggaagt gtgggtcccg tgggtcctgc    7980
tggtcccatt gggtctgctg gccctccagg cttcccaggt gccctggcc caagggtga      8040 aattggagct gttggtaacg ctggtcctgc tggtcccgcc ggtcccgtg gtgaagtggg     8100 tcttccaggc ctctccggcc ccgttggacc tcctggtaat cctggagcaa acggccttac    8160
tggtgccaag ggtgctgctg gccttcccgg cgttgctggg gctcccggcc tccctggacc    8220
ccgcggtatt cctggccctg ttggtgctgc cggtgctact ggtgccagag gacttgttgg    8280
tgagcctggt ccagctggct ccaaaggaga gagcggtaac aagggtgagc ccggctctgc    8340
tgggccccaa ggtcctcctg gtcccagtgg tgaagaagga agagaggcc ctaatgggga     8400 agctggatct gccggccctc caggacctcc tgggctgaga ggtagtcctg gttctcgtgg    8460
tcttcctgga gctgatggca gagctggcgt catgggccct cctggtagtc gtggtgcaag    8520
tggccctgct ggagtccgag gacctaatgg agatgctggt cgccctgggg agcctggtct    8580
catgggaccc agaggtcttc ctggttcccc tggaaatatc ggccccgctg gaaaagaagg    8640
tcctgtcggc ctccctggca tcgacggcag gcctggccca attggcccag ctggagcaag    8700
aggagagcct ggcaacattg gattccctgg acccaaaggc cccactggtg atcctggcaa    8760
aaacggtgat aaaggtcatg ctggtcttgc tggtgctcgg ggtgctccag gtcctgatgg    8820
aaacaatggt gctcagggac ctcctggacc acagggtgtt caaggtggaa aggtgaaca      8880 gggtcccgct ggtcctccag gcttccaggg tctgcctggc ccctcaggtc ccgctggtga    8940
agttggcaaa ccaggagaaa ggggtctcca tggtgagttt ggtctccctg gtcctgctgg    9000
tccaagaggg gaacgcggtc cccaggtga gagtggtgct gccggtccta ctggtcctat     9060
tggaagccga ggtccttctg gaccccagg gcctgatgga acaagggtg aacctggtgt      9120 ggttggtgct gtgggcactg ctggtccatc tggtcctagt ggactcccag gagagagggg    9180
```

```
tgctgctggc atacctggag gcaagggaga aaagggtgaa cctggtctca gaggtgaaat    9240
tggtaaccct ggcagagatg gtgctcgtgg tgctcctggt gctgtaggtg ccctggtcc     9300
tgctggagcc acaggtgacc ggggcgaagc tggggctgct ggtcctgctg gtcctgctgg    9360
tcctcgggga agcctggtg aacgtggtga ggtcggtcct gctggcccca atggatttgc     9420
tggtcctgct ggtgctgctg gtcaacctgg tgctaaagga gaagaggag ccaaagggcc     9480
taagggtgaa aacggtgttg ttggtcccac aggccccgtt ggagctgctg cccagctgg     9540
tccaaatggt ccccccggtc ctgctggaag tcgtggtgat ggaggccccc ctggtatgac    9600
tggtttccct ggtgctgctg gacggactgg tcccccagga ccctctggta tttctggccc    9660
tcctggtccc cctggtcctg ctgggaaaga agggcttcgt ggtcctcgtg gtgaccaagg    9720
tccagttggc cgaactggag aagtaggtgc agttggtccc cctggcttcg ctggtgagaa    9780
gggtcccctct ggagaggctg gtactgctgg acctcctggc actccaggtc ctcagggtct   9840
tcttggtgct cctggtattc tgggtctccc tggctcgaga ggtgaacgtg gtctaccagg    9900
tgttgctggt gctgtgggtg aacctggtcc tcttggcatt gccggccctc ctggggcccg    9960
tggtcctcct ggtgctgtgg gtagtcctgg agtcaacggt gctcctggtg aagctggtcg   10020
tgatggcaac cctgggaacg atggtccccc aggtcgcgat ggtcaacccg gacacaaggg   10080
agagcgcggt taccctggca atattggtcc cgttggtgct gcaggtgcac ctggtcctca   10140
tggccccgtg ggtcctgctg gcaaacatgg aaaccgtggt gaaactggtc cttctggtcc   10200
tgttggtcct gctggtgctg ttggcccaag aggtcctagt ggcccacaag gcattcgtgg   10260
cgataaggga gagcccggtg aaaaggggcc cagaggtctt cctggcttaa agggacacaa   10320
tggattgcaa ggtctgcctg gtatcgctgg tcaccatggt gatcaaggtg ctcctggctc   10380
cgtgggtcct gctggtccta ggggccctgc tggtccttct ggccctgctg gaaaagatgg   10440
tcgcactgga catcctggta cagttggacc tgctggcatt cgaggccctc agggtcacca   10500
aggccctgct ggccccctg gtcccccctgg ccctcctgga cctccaggtg taagcggtgg   10560
tggttatgac tttggttacg atggagactt ctacagggct gaccagcctc gctcagcacc   10620
ttctctcaga cccaaggact atgaagttga tgctactctg aagtctctca acaaccagat   10680
tgagaccctt cttactcctg aaggctctag aaagaaccca gctcgcacat gccgtgactt   10740
gagactcagc cacccagagt ggagcagtgg ttactactgg attgacccta accaaggatg   10800
cactatggat gctatcaaag tatactgtga tttctctact ggcgaaacct gtatccgggc   10860
ccaacctgaa aacatcccag ccaagaactg gtataggagc tccaaggaca agaaacacgt   10920
ctggctagga gaaactatca atgctggcag ccagtttgaa tataatgtag aaggagtgac   10980
ttccaaggaa atggcctaccc aacttgcctt catgcgcctg ctggccaact atgcctctca   11040
gaacatcacc taccactgca agaacagcat tgcatacatg gatgaggaga ctggcaacct   11100
gaaaaaggct gtcattctac agggctctaa tgatgttgaa cttgttgctg agggcaacag   11160
caggttcact tacactgttc ttgtagatgg ctgctctaaa aagacaaatg aatggggaaa   11220
gacaatcatt gaatacaaaa caaataagcc atcacgcctg cccttccttg atattgcacc   11280
tttggacatc ggtggtgctg accaggaatt ctttgtggac attggcccag tctgttttca   11340
ataagtcgac tcgctgatca gcctcgactt tgccttctag ttgccagcca tctgttgttt   11400
gccccctccc cgtgccttcc ttgaccctgg aaggtgccac tcccactgtc ctttcctaat   11460
aaaatgagga aattgcatcg cattgtctga gtaggtgtca ttctattctg gggggtgggg   11520
tggggcagga cagcaagggg gaggattggg aagacaatag caggcactcg accctcgacc   11580
```

```
tcgaaattct accgggtagg ggaggcgctt ttcccaaggc agtctggagc atgcgcttta   11640
gcagccccgc tgggcacttg gcgctacaca agtggcctct ggcctcgcac acattccaca   11700
tccaccggta ggcgccaacc ggctccgttc tttggtggcc ccttcgcgcc accttctact   11760
cctcccctag tcaggaagtt ccccccgcc ccgcagctcg cgtcgtgcag gacgtgacaa   11820
atggaagtag cacgtctcac tagtctcgtg cagatggaca gcaccgctga gcaatggaag   11880
cgggtaggcc tttggggcag cggccaatag cagctttgct ccttcgcttt ctgggctcag   11940
aggctgggaa ggggtgggtc cggggcggg ctcaggggcg ggctcagggg cggggcgggc   12000
gcccgaaggt cctccggagg cccggcattc tgcacgcttc aaaagcgcac gtctgccgcg   12060
ctgttctcct cttcctcatc tccgggcctt tcgacctgca tccatctaga tctagatcag   12120
cttaccatga ccgagtacaa gcccacggtg cgcctcgcca cccgcgacga cgtccccagg   12180
gccgtacgca ccctcgccgc cgcgttcgcc gactaccccg ccacgcgcca caccgtcgat   12240
ccggaccgcc acatcgagcg ggtcaccgag ctgcaagaac tcttcctcac gcgcgtcggg   12300
ctcgacatcg gcaaggtgtg ggtcgcggac gacggcgccg cggtggcggt ctggaccacg   12360
ccggagagcg tcgaagcggg ggcggtgttc gccgagatcg gcccgcgcat ggccgagttg   12420
agcggttccc ggctggccgc gcagcaacag atggaaggcc tcctggcgcc gcaccggccc   12480
aaggagcccg cgtggttcct ggccaccgtc ggcgtctcgc ccgaccacca gggcaagggt   12540
ctgggcagcg ccgtcgtgct ccccggagtg gaggcggccg agcgcgccgg ggtgccgcc   12600 ttcctggaga cctccgcgcc ccgcaacctc cccttctacg agcggctcgg cttcaccgtc   12660
accgccgacg tcgaggtgcc cgaaggaccg cgcacctggt gcatgacccg caagcccgtg   12720
gcctgacgcc cgccccacga cccgcagcgc ccgaccgaaa ggagcgcacg acccatgca   12780 tcgatgatgc caataaagat atcattgatg agtttggaca aaccacaact agaatgcagt   12840 gaaaaaatg cttatttgt gaatttgtg atgctattgc tttatttgta accattataa   12900
gctgcatatc gaattcccgc ggccgcggga attcgattcc atcggtgcag caagcatgga   12960
attttgtttt gatgtattca aggagctcaa agtccaccat gccaatgaga acatcttcta   13020
ctgccccatt gccatcatgt cagctctagc catggtatac ctgggtgcaa aagacagcac   13080
caggacacag ataaataagg tgagcctaca gttaaagatt aaaacctttg ccctgctcaa   13140
tggagccaca gcacttaatt gtatgataat gtcccttgga aactgcatag ctcagaggct   13200
gaaaatctga aaccagagtt atctaaaagt gtggccacct ccaactccca gagtgttacc   13260
caaatgcact agctagaaat cttgaaactg gattgcataa cttcttttg tcataaccat   13320 tatttcagct actattattt tcaattacag gttgttcgct ttgataaact tccaggattc   13380
ggagacagta ttgaagctca ggtacagaaa taatttcacc tccttctcta tgtccctttc   13440
ctctggaagc aaaatacagc agatgaagca atctcttagc tgttccaagc cctctctgat   13500
gagcagctag tgctctgcat ccagcagttg ggagaacact gttcataaga acagagaaaa   13560
agaaggaagt aacagggat tcagaacaaa cagaagataa aactcaggac aaaaataccg   13620
tgtgaatgag gaaacttgtg gatatttgta cgcttaagca agacagctag atgattctgg   13680
ataaatgggt ctggttggaa aagaaggaaa gcctggctga tctgctggag ctagattatt   13740
gcagcaggta ggcaggagtt ccctagagaa aagtatgagg gaattacaga agaaaaacag   13800
cacaaaattg taaatattgg aaaaggacca catcagtgta gttactagca gtaagacaga   13860
caggatgaaa aatagttttg taaacagaag tatctaacta ctttactctg ttcatacact   13920
```

```
atgtaaaacc tactaagtaa taaaactaga ataacaacat ctttctttct ctttgtattc    13980
agtgtggcac atctgtaaac gttcactctt cacttagaga catcctcaac caaatcacca    14040
aaccaaatga tgtttattcg ttcagccttg ccagtagact ttatgctgaa gagagatacc    14100
caatcctgcc agtaagttgc tctaaaatct gatctgagtg tatttccatg ccaaagctct    14160
accattctgt aatgcaaaaa cagtcagagt tccacatgtt tcactaagaa aatttctttt    14220
tctcttgttt ttacaaatga aagagaggac aaataacatt tctctatcac cgacctgaaa    14280
ctctacagtc ttcagagaat gaatggcttg ctaaaagaat gtcaaatctt accatacagc    14340
tatttcatat tacactacta aatacactat aaggcatagc atgtagtaat acactgtaaa    14400
atagcttttt acactactat attattaata tctgttaatt ccagtcttgc atttcacatt    14460
tgcaaaacgt tttgaaattc gtatctgaaa gctgaatact cttgctttac aggaatactt    14520
gcagtgtgtg aaggaactgt atagaggagg cttggaacct atcaactttc aaacagctgc    14580
agatcaagcc agagagctca tcaattcctg ggtagaaagt cagacaaatg gtaaggtaga    14640
acatgctttg tacatagtga gagttggttc accctaatac tgagaacctg gatatagctc    14700
agccagcgtg ctttgcgttc aagcttacca gagctgttgt atgcctgtta agcagggcat    14760
acagtcatga ggctcttgaa aaatcttaac agacaaaggg caatggaaaa tcggagttaa    14820
gggatggtag ggataaaatg catagaaaga ggtaccacga ttttgatttt tgccctaatg    14880
cctctctgcg tggttcctca atttttctac ttcattcctc atctcctcag agcattcctt    14940
tccctcatgc ttgaaacaca gatgaaagac tgtgaattct aactgagatg aaaacatcca    15000
caaccacaca acctctggtg tggagtcaca ttctgtgaag gcaaaaacta ggccacgtaa    15060
tctatgtgtg caagctacgt gtaagctatg tgtgtgacag acaatgtgaa ggaacatact    15120
atgtgcacaa ggactgcaga ataaacagga gcaaagtttt tgaagaaaac agagtaaaat    15180
cccgttttcc tcttttgtta cattctttac atatatctca aatttcctct ttggttagaa    15240
gcaagtaata tttatgtttc ttggtactgt ttggggttgaa gaccattctg ggataagaga    15300
aattccagtg gttcttcccc taatcataaa atgtacaggt ttagtttttt tgtaacacag    15360
aaatctcttc atcttttatc ttttgttgtg attctttata gagagagaaa caagacttac    15420
tgacaatagc agcaagaaaa tcaatcttgg aagaacaaga ttgcagttgc aaaaacaaac    15480
caatgtcctt gccctacat cctcttcccc ataaattcta cattctctat ctaccttgtg    15540
cttgccaaca tgatatacgt aaactctctt ttcctattca ttcttaaagg aattatcaga    15600
aatgtccttc agccaagctc cgtggattct caaactgcaa tggttctggt taatgccatt    15660
gtcttcaaag gactgtggga gaaagcattt aaggatgaag acacacaagc aatgcctttc    15720
agagtgactg aggtatatgg gcataccttta gagatgtaat ctagaattta tgaagagagt    15780
agacatgttg ttatatgaac actgcattag cgtatctgct catttgtctg catctctttc    15840
agacactgtg ttaaaagcag ggaattttcc ttatgtctct ttcatcacaa tattcctgac    15900
attgcaaagc tcctgagaaa taacttcaga ttcccacttt tcctagggag gtcttcctgg    15960
atgagaacaa tcaatcatct taactgtaac tagatatttc tgcatctaag aataatcttt    16020
gttaaaacta tattctctct ctcttttttt ttttttttgg ttctccagca agaaagcaaa    16080
cctgtgcaga tgatgtggat cc                                            16102
```

<210> SEQ ID NO 32
<211> LENGTH: 16474
<212> TYPE: DNA
<213> ORGANISM: human

```
<220> FEATURE:
<221> NAME/KEY: misc_feature
<222> LOCATION: (13276)..(13278)
<223> OTHER INFORMATION: n is a, c, g, or t

<400> SEQUENCE: 32 gtcgaccttca agtcctcaga cttggcaagg agaatgtaga tttctacagt atatatgttt      60
tcacaaaagg aaggagagaa acaaaagaaa atggcactga ctaaacttca gctagtggta     120
taggaaagta attctgctta acagagattg cagtgatctc tatgtatgtc ctgaagaatt     180
atgttgtact ttttccctc attttaaat caaacagtgc tttacagagg tcagaatggt     240
ttctttactg tttgtcaatt ctattattc aatacagaac aatagcttct ataactgaaa     300
tatatttgct attgtatatt atgattgtcc ctcgaaccat gaacactcct ccagctgaat     360
ttcacaattc ctctgtcatc tgccaggcca ttaagttatt catggaagat ctttgaggaa     420
cactgcaagt tcatatcata aacacatttg aaattgagta ttgttttgca ttgtatggag     480
ctatgttttg ctgtatcctc agaaaaaaag tttgttataa agcattcaca cccataaaaa     540
gatagattta atattccag ctataggaaa gaaagtgcgt ctgctcttca ctctagtctc     600
agttggctcc ttcacatgca cgcttcttta ttctcctat tttgtcaaga aataatagg     660 tcacgtcttg ttctcactta tgtcctgcct agcatggctc agatgcacgt tgtacataca     720
agaaggatca aatgaaacag acttctggtc tgttactaca accatagtaa taagcacact     780
aactaataat tgctaattat gttttccatc tccaaggttc ccacattttt ctgttttctt     840
aaagatccca ttatctggtt gtaactgaag ctcaatggaa catgagcaat atttccagt     900 cttctctccc atccaacagt cctgatggat tagcagaaca ggcagaaaac acattgttac     960
ccagaattaa aaactaatat ttgctctcca ttcaatccaa aatggaccta ttgaaactaa    1020
aatctaaccc aatcccatta aatgatttct atggcgtcaa aggtcaaact tctgaaggga    1080
acctgtgggt gggtcacaat tcaggctata tattccccag ggctcagcca gtgtctgtac    1140
atacagctag aaagctgtat tgcctttagc actcaagctc aaaaggtaag caactctctg    1200
gaattacctt ctctctatat tagctcttac ttgcacctaa actttaaaaa attaacaatt    1260
attgtgttat gtgttgtatc tttaagggtg aagtacctgc gtgatacccc ctataaaaac    1320
ttctcacctg tgtatgcatt ctgcactatt ttattatgtg taaaagcttt gtgtttgttt    1380
tcaggaggct tattctttgt gcttaaaata tgttttaat ttcagaacat cttatcctgt    1440
cgttcactat ctgatatgct ttgcagtttg cctgattaac ttctagccct acagagtgca    1500
cagagagcaa aatcatggtg ttcagtgaat tctggggagt tatttaatg tgaaaattct    1560 ctagaagttt aattcctgca aagtgcagct gctgatcact acacaagata aaaatgtggg    1620
gggtgcataa acgtatattc ttacaataat agatacatgt gaacttgtat acagaaaga    1680 aaatgagaaa aatgtgtgtg cgtatactca cacacgtggt cagtaaaaac ttttgagggg    1740
tttaatacag aaaatccaat cctgaggccc cagcactcag tacgcatata aagggctggg    1800
ctctgaagga cttctgactt tcacagatta tataaatctc aggaaagcaa ctagattcat    1860
gctggctcca aaagctgtgc tttatataag cacactggct atacaatagt tgtacagttc    1920
agctctttat aatagaaaca gacagaacaa gtataaatct tctattggtc tatgtcatga    1980
acaagaattc attcagtggc tctgtttat agtaaacatt gctattttat catgtctgca    2040
tttctcttct gtctgaatgt caccactaaa atttaactcc acagaaagtt tatactacag    2100
tacacatgca tatctttgag caaagcaaac catacctgaa agtgcaatag agcagaatat    2160
```

| | |
|---|---|
| gaattacatg cgtgtctttc tcctagacta catgacccca tataaattac attccttatc | 2220 |
| tattctgcca tcaccaaaac aaaggtaaaa atacttttga agatctactc atagcaagta | 2280 |
| gtgtgcaaca aacagatatt tctctacatt tattttagg gaataaaaat aagaaataaa | 2340 |
| atagtcagca agcctctgct ttctcatata tctgtccaaa cctaaagttt actgaaattt | 2400 |
| gctctttgaa tttccagttt tgcaagccta tcagattgtg ttttaatcag aggtactgaa | 2460 |
| aagtatcaat gaattctagc tttcactgaa caaaaatatg tagaggcaac tggcttctgg | 2520 |
| gacagtttgc tacccaaaag acaactgaat gcaaatacat aaatagattt atgaatatgg | 2580 |
| ttttgaacat gcacatgaga ggtggatata gcaacagaca cattaccaca gaattacttt | 2640 |
| aaaactactt gttaacattt aattgcctaa aaactgctcg taatttactg ttgtagccta | 2700 |
| ccatagagta ccctgcatgg tactatgtac agcattccat ccttacattt tcactgttct | 2760 |
| gctgtttgct ctagacaact cagagttcac catgaggtct ttgctaatct tggtgctttg | 2820 |
| cttcctgccc ctggctgctc tggggcaaga ggaaggccaa gtcgagggcc aagacgaaga | 2880 |
| catcccacca atcacctgcg tacagaacgg cctcaggtac catgaccgag acgtgtggaa | 2940 |
| acccgagccc tgccggatct gcgtctgcga caacggcaag gtgttgtgcg atgacgtgat | 3000 |
| ctgtgacgag accaagaact gccccggcgc cgaagtcccc gagggcgagt gctgtcccgt | 3060 |
| ctgcccccgac ggctcagagt cacccaccga ccaagaaacc accggcgtcg agggacccaa | 3120 |
| gggagacact ggccccgag gcccaagggg acccgcaggc ccccctggcc gagatggcat | 3180 |
| ccctggacag cctggacttc ccggaccccc cggaccccccc ggacctcccg gacccctgg | 3240 |
| cctcggagga aactttgctc cccagctgtc ttatggctat gatgagaaat caaccggagg | 3300 |
| aatttccgtg cctggcccca tgggtccctc tggtcctcgt ggtctccctg gccccctgg | 3360 |
| tgcacctggt ccccaaggct tccaaggtcc cctggtgag cctggcgagc ctggagcttc | 3420 |
| aggtcccatg ggtccccgag gtccccagg tccccctgga aagaatggag atgatgggga | 3480 |
| agctggaaaa cctggtcgtc ctggtgagcg tgggcctcct gggcctcagg gtgctcgagg | 3540 |
| attgcccgga acagctggcc tccctggaat gaagggacac agaggtttca gtggtttgga | 3600 |
| tggtgccaag ggagatgctg gtcctgctgg tcctaagggt gagcctggca gccctggtga | 3660 |
| aaatggagct cctggtcaga tgggcccccg tggcctgcct ggtgagagag gtcgccctgg | 3720 |
| agccctggc cctgctggtg ctcgtggaaa tgatggtgct actggtgctg ccgggccccc | 3780 |
| tggtcccacc ggccccgctg gtcctcctgg cttccctggt gctgttggtg ctaagggtga | 3840 |
| agctggtccc caagggcccc gaggctctga aggtccccag ggtgtgcgtg gtgagcctgg | 3900 |
| cccccctggc cctgctggtg ctgctggccc tgctggaaac cctggtgctg atggacagcc | 3960 |
| tggtgctaaa ggtgccaatg gtgctcctgg tattgctggt gctcctggct cccctggtgc | 4020 |
| ccgaggcccc tctggacccc agggcccccgg cggccctcct ggtcccaagg gtaacagcgg | 4080 |
| tgaacctggt gctcctggca gcaaaggaga cactggtgct aagggagagc ctggccctgt | 4140 |
| tggtgttcaa ggaccccctg gccctgctgg agaggaagga aagcgaggag ctcgaggtga | 4200 |
| acccggaccc actggcctgc ccggaccccc tggcgagcgt ggtggacctg gtagccgtgg | 4260 |
| tttccctggc gcagatggtg ttgctggtcc caagggtccc gctggtgaac gtggttctcc | 4320 |
| tggccctgct ggccccaaag gatctcctgg tgaagctggt cgtcccggtg aagctggtct | 4380 |
| gcctggtgcc aagggtctga ctggaagccc tggcagccct ggtcctgatg gcaaaactgg | 4440 |
| cccccctggt cccgccggtc aagatggtcg ccccggaccc ccaggccccac ctggtgcccg | 4500 |
| tggtcaggct ggtgtgatgg gattccctgg acctaaaggt gctgctggag agcccggcaa | 4560 |

```
ggctggagag cgaggtgttc ccggaccccc tggcgctgtc ggtcctgctg gcaaagatgg    4620
agaggctgga gctcagggac ccccTggccc tgctggtccc gctggcgaga gaggtgaaca    4680
aggccctgct ggctcccccg gattccaggg tctccctggt cctgctggtc ctccaggtga    4740
agcaggcaaa cctggtgaac agggtgttcc tggagacctt ggcgcccctg gcccctctgg    4800
agcaagaggc gagagaggtt tccctggcga gcgtggtgtg caaggtcccc ctggtcctgc    4860
tggtccccga ggggccaacg gtgctcccgg caacgatggt gctaagggtg atgctggtgc    4920
ccctggagct cccggtagcc agggcgcccc tggccttcag ggaatgcctg gtaacgtgg     4980
tgcagctggt cttccagggc ctaagggtga cagaggtgat gctggtccca aggtgctga    5040
tggctctcct ggcaaagatg gcgtccgtgg tctgactggc cccattggtc ctcctggccc    5100
tgctggtgcc cctggtgaca agggtgaaag tggtcccagc ggccctgctg gtcccactgg    5160
agctcgtggt gcccccggag accgtggtga gcctggtccc ccggccctg ctggctttgc     5220
tggccccct ggtgctgacg gccaacctgg tgctaaaggc gaacctggtg atgctggtgc     5280
taaaggcgat gctggtcccc ctggccctgc cggacccgct ggacccctg gcccattgg      5340
taatgttggt gctcctggag ccaaaggtgc tcgcggcagc gctggtcccc ctggtgctac    5400
tggtttccct ggtgctgctg gccgagtcgg tcctcctggc ccctctggaa atgctggacc    5460
ccctggcccc cctggtcctg ctggcaaaga aggcggcaaa ggtccccgtg gtgagactgg    5520
ccctgctgga cgtcctggtg aagttggtcc ccctggtccc cctggccctg ctggcgagaa    5580
aggatcccct ggtgctgatg gtcctgctgg tgctcctggt actcccgggc ctcaaggtat    5640
tgctggacag cgtggtgtgg tcggcctgcc tggtcagaga ggagagagag gcttccctgg    5700
tcttcctggc ccctctggtg aacctggcaa acaaggtccc tctggagcaa gtggtgaacg    5760
tggtcccct ggtcccatgg gccccctgg attggctgga ccccctggtg aatctggacg      5820
tgaggggct cctggtgccg aaggttcccc tggacgagac ggttctcctg cgcaaggg       5880
tgaccgtggt gagaccggcc ccgctggacc ccctggtgct cctggtgctc ctggtgcccc    5940
tggccccgtt ggccctgctg gcaagagtgg tgatcgtggt gagactgtc ctgctggtcc     6000
cgccggtcct gtcggccctg ttggcgcccg tggccccgcc ggaccccaag gccccgtgg     6060
tgacaagggt gagacaggcg aacagggcga cagaggcata agggtcacc gtggcttctc     6120
tggcctccag ggtccccctg gccctcctgg ctctcctggt gaacaaggtc cctctggagc    6180
ctctggtcct gctggtcccc gaggtccccc tggctctgct ggtgctcctg gcaaagatgg    6240
actcaacggt ctccctggcc ccattgggcc cctggtcct cgcggtcgca ctggtgatgc     6300
tggtcctgtt ggtccccccg gccctcctgg acctcctggt cccctggtc ctcccagcgc     6360
tggtttcgac ttcagcttcc tgccccagcc acctcaagag aaggctcacg atggtggccg    6420
ctactaccgg gctgatgatg ccaatgtggt tcgtgaccgt gacctcgagg tggacaccac    6480
cctcaagagc ctgagccagc agatcgagaa catccgagc ccagggca gccgcaagaa       6540
cccgccgc acctgccgtg acctcaagat gccactct gactggaaga gtggagagta         6600
ctggattgac cccaaccaag gctgcaacct ggatgccatc aaagtcttct gcaacatgga    6660
gactggtgag acctgcgtgt accccactca gcccagtgtg gcccagaaga actggtacat    6720
cagcaagaac cccaaggaca gaggcatgt ctggttcggc gagagcatga ccgatggatt     6780
ccagttcgag tatggcggcc agggctccga ccctgccgat gtggccatcc agctgacctt    6840
cctgcgcctg atgtccaccg aggcctccca gaacatcacc taccactgca agaacagcgt    6900
```

```
ggcctacatg gaccagcaga ctggcaacct caagaaggcc ctgctcctcc agggctccaa    6960
cgagatcgag atccgcgccg agggcaacag ccgcttcacc tacagcgtca ctgtcgatgg    7020
ctgcacgagt cacaccggag cctggggcaa gacagtgatt gaatacaaaa ccaccaagac    7080
ctcccgcctg cccatcatcg atgtggcccc cttggacgtt ggtgcccag accaggaatt     7140 cggcttcgac gttggccctg tctgcttcct gcgggccaag agagccccg tgaagcagac      7200 cctgaacttc gacctgctga agctggccgg cgacgtggag tccaaccccg ccccatgcg     7260 ctccctcttg attctcgtct tgtgtttttt gccactggcc gctctcggcc aatctttaca    7320
agaggaaact gtaagaaagg cccagccgg agatagagga ccacgtggag aaaggggtcc     7380
accaggcccc ccaggcagag atggtgaaga tggtcccaca ggccctcctg gtccacctgg    7440
tcctcctggc cccctggtc tcggtgggaa ctttgctgct cagtatgatg aaaaggagt      7500 tggacttggc cctggaccaa tgggcttaat gggacctaga ggcccacctg gtgcagctgg    7560
agccccaggc cctcaaggtt tccaaggacc tgctggtgag cctggtgaac ctggtcaaac    7620
tggtcctgca ggtgctcgtg gtccagctgg ccctcctggc aaggctggtg aagatggtca    7680
ccctggaaaa cccggacgac ctggtgagag aggagttgtt ggaccacagg gtgctcgtgg    7740
tttccctgga actcctggac ttcctggctt caaaggcatt aggggacaca atggtctgga    7800
tggattgaag ggacagcccg gtgctcctgg tgtgaagggt gaacctggtg ccctggtga    7860 aaatggaact ccaggtcaaa caggagcccg tgggcttcct ggtgagagag acgtgttgg    7920 tgccctggc ccagctggtg cccgtggcag tgatggaagt gtgggtcccg tggtcctgc     7980 tggtccatt gggtctgctg gccctccagg cttcccaggt gccctggcc caagggtga     8040 aattggagct gttggtaacg ctggtcctgc tggtcccgcc ggtcccgtg gtgaagtggg    8100 tcttccagge ctctccggcc ccgttggacc tcctggtaat cctggagcaa acggccttac    8160
tggtgccaag ggtgctgctg gccttccgg cgttgctggg gctcccggcc tcctggacc     8220 ccgcggtatt cctggccctg ttggtgctgc cggtgctact ggtgccagag acttgttgg    8280 tgagcctggt ccagctggct ccaaaggaga gagcggtaac aagggtgagc ccggctctgc   8340
tgggccccaa ggtcctcctg gtcccagtgg tgaagaagga agagaggcc ctaatgggga   8400 agctggatct gccggcccte caggacctcc tgggctgaga ggtagtcctg gttctcgtgg    8460
tcttcctgga gctgatggca gagctggcgt catgggccct cctggtagtc gtggtgcaag    8520
tggccctgct ggagtccgag gacctaatgg agatgctggt cgccctgggg agcctggtct    8580
catgggaccc agaggtcttc ctggttcccc tggaaatatc ggccccgctg gaaaagaagg    8640
tcctgtcggc ctccctggca tcgacggcag gcctggccca attggcccag ctggagcaag    8700
aggagagcct ggcaacattg gattccctgg acccaaaggc cccactgtg atcctggcaa    8760 aaacggtgat aaaggtcatg ctggtcttgc tggtgctcgg ggtgctccag gtcctgatgg    8820
aaacaatggt gctcagggac ctccctggacc acagggtgtt caaggtggaa aaggtgaaca    8880
gggtcccgct ggtcctccag gcttccaggg tctgcctggc ccctcaggtc ccgctggtga    8940
agttggcaaa ccaggagaaa ggggtctcca tggtgagttt ggtctccctg gtcctgctgg    9000
tccaagaggg gaacgcggtc cccaggtga agtggtgct gccggtccta ctggtcctat       9060
tggaagccga ggtccttctg gaccccagg gcctgatgga acaaggtg aacctggtgt        9120 ggttggtgct gtgggcactg ctggtccatc tggtcctagt ggactcccag gagagagggg    9180
tgctgctggc ataccggag gcaagggaga aaagggtgaa cctggtctca gaggtgaaat     9240
tggtaaccct ggcagagatg gtgctcgtgg tgctcctggt gctgtaggtg cccctggtcc    9300
```

```
tgctggagcc acaggtgacc ggggcgaagc tggggctgct ggtcctgctg gtcctgctgg    9360
tcctcgggga agccctggtg aacgtggtga ggtcggtcct gctggcccca atggatttgc    9420
tggtcctgct ggtgctgctg gtcaacctgg tgctaaagga gaaagaggag ccaaagggcc    9480
taagggtgaa aacggtgttg ttggtcccac aggccccgtt ggagctgctg cccagctgg     9540 tccaaatggt ccccccggtc ctgctggaag tcgtggtgat ggaggccccc ctggtatgac    9600
tggtttccct ggtgctgctg gacggactgg tcccccagga ccctctggta tttctggccc    9660
tcctggtccc cctggtcctg ctgggaaaga agggcttcgt ggtcctcgtg gtgaccaagg    9720
tccagttggc cgaactggag aagtaggtgc agttggtccc cctggcttcg ctggtgagaa    9780
gggtccctct ggagaggctg gtactgctgg acctcctggc actccaggtc ctcagggtct    9840
tcttggtgct cctggtattc tgggtctccc tggctcgaga ggtgaacgtg gtctaccagg    9900
tgttgctggt gctgtgggtg aacctggtcc tcttggcatt gccggccctc ctggggcccg    9960
tggtcctcct ggtgctgtgg gtagtcctgg agtcaacggt gctcctggtg aagctggtcg   10020
tgatggcaac cctgggaacg atggtccccc aggtcgcgat ggtcaacccg acacaaggg    10080 agagcgcggt taccctggca atattggtcc cgttggtgct gcaggtgcac ctggtcctca   10140
tggccccgtg ggtcctgctg gcaaacatgg aaaccgtggt gaaactggtc cttctggtcc   10200
tgttggtcct gctggtgctg ttggcccaag aggtcctagt ggcccacaag gcattcgtgg   10260
cgataaggga gagcccggtg aaaaggggcc cagaggtctt cctggcttaa agggacacaa   10320
tggattgcaa ggtctgcctg gtatcgctgg tcaccatggt gatcaaggtg ctcctggctc   10380
cgtgggtcct gctggtccta ggggccctgc tggtccttct ggccctgctg gaaaagatgg   10440
tcgcactgga catcctggta cagttggacc tgctggcatt cgaggccctc agggtcacca   10500
aggccctgct ggccccctg gtcccccctgg ccctcctgga cctccaggtg taagcggtgg   10560
tggttatgac tttggttacg atggagactt ctacagggct gaccagcctc gctcagcacc   10620
ttctctcaga cccaaggact atgaagttga tgctactctg aagtctctca caaccagat    10680 tgagacccct ttactcctg aaggctctag aaagaaccca gctcgcacat gccgtgactt    10740
gagactcagc cacccagagt ggagcagtgg ttactactgg attgaccta accaaggatg    10800 cactatggat gctatcaaag tatactgtga ttctctact ggcgaaacct gtatccgggc    10860
ccaacctgaa aacatcccag ccaagaactg gtataggagc tccaaggaca agaaacgt     10920 ctggctagga gaaactatca atgctggcag ccagtttgaa tataatgtag aaggagtgac   10980
ttccaaggaa atggctaccc aacttgcctt catgcgcctg ctggccaact atgcctctca   11040
gaacatcacc taccactgca agaacagcat tgcatacatg gatgaggaga ctggcaacct   11100
gaaaaaggct gtcattctac agggctctaa tgatgttgaa cttgttgctg agggcaacag   11160
caggttcact tacactgttc ttgtagatgg ctgctctaaa aagacaaatg aatgggaaa    11220 gacaatcatt gaatacaaaa caaataagcc atcacgcctg cccttccttg atattgcacc   11280
tttggacatc ggtggtgctg accaggaatt ctttgtggac attggcccag tctgtttcaa   11340
ataagtcgac tcgctgatca gcctcgactt tgccttctag ttgccagcca tctgttgttt   11400 gccctcccc cgtgccttcc ttgacctgg aaggtgccac tcccactgtc ctttcctaat    11460 aaatgagga aattgcatcg cattgtctga gtaggtgtca ttctattctg gggggtgggg    11520
tggggcagga cagcaagggg gaggattggg aagacaatag caggcactcg accctcgact   11580
tcaaatatgt atccgctcat gagacaataa ccctgataaa tgcttcaata atattgaaaa   11640
```

```
aggaagagtc ctgaggcgga aagaaccagc tgtggaatgt gtgtcagtta gggtgtggaa    11700
agtccccagg ctccccagca ggcagaagta tgcaaagcat gcatctcaat tagtcagcaa    11760
ccaggtgtgg aaagtcccca ggctccccag caggcagaag tatgcaaagc atgcatctca    11820
attagtcagc aaccatagtc ccgcccctaa ctccgcccat cccgcccta actccgccca     11880 gttccgccca ttctccgccc catggctgac taattttttt tatttatgca gaggccgagg    11940
ccgcctcggc ctctgagcta ttccagaagt agtgaggagg cttttttgga ggcctaggct    12000
tttgcaaaga tcgatcaaga gacaggatga ggatcgtttc gcatgattga acaagatgga    12060
ttgcacgcag gttctccggc cgcttgggtg gagaggctat tcggctatga ctgggcacaa    12120
cagacaatcg gctgctctga tgccgccgtg ttccggctgt cagcgcaggg gcgcccggtt    12180 cttttgtca agaccgacct gtccggtgcc ctgaatgaac tgcaagacga ggcagcgcgg     12240
ctatcgtggc tggccacgac gggcgttcct tgcgcagctg tgctcgacgt tgtcactgaa    12300
gcgggaaggg actggctgct attgggcgaa gtgccggggc aggatctcct gtcatctcac    12360
cttgctcctg ccgagaaagt atccatcatg gctgatgcaa tgcggcggct gcatacgctt    12420
gatccggcta cctgcccatt cgaccaccaa gcgaaacatc gcatcgagcg agcacgtact    12480
cggatggaag ccggtcttgt cgatcaggat gatctggacg aagagcatca ggggctcgcg    12540
ccagccgaac tgttcgccag gctcaaggcg agcatgcccg acggcgagga tctcgtcgtg    12600
acccatggcg atgcctgctt gccgaatatc atggtggaaa atggccgctt tctggattc    12660 atcgactgtg gccggctggg tgtggcggac cgctatcagg acatagcgtt ggctacccgt    12720
gatattgctg aagagcttgg cggcgaatgg gctgaccgct tcctcgtgct ttacggtatc    12780
gccgctcccg attcgcagcg catcgccttc tatcgccttc ttgacgagtt cttctgagcg    12840
ggactctggg gttcgaaatg accgaccaag cgacgcccaa cctgccatca cgagatttcg    12900
attccaccgc cgccttctat gaaaggttgg gcttcggaat cgttttccgg gacgccggct    12960
ggatgatcct ccagcgcggg gatctcatgc tggagttctt cgcccaccct agggggaggc    13020
taactgaaac acggaaggag acaataccgg aaggaacccg cgctatgacg gcaataaaaa    13080
gacagaataa aacgcacggt gttgggtcgt ttgttcataa acgcggggtt cggtcccagg    13140
gctggcactc tgtcgatacc ccaccgagac cccattgggg ccaatacgcc cgcgtttctt    13200 cctttccc accccacccc ccaagttcgg gtgaaggccc agggctcgca gccaacgtcg     13260
gggcggcagg ctgcannnta tcgaattccc gcggccgcgg gaattcgatt ccatcggtgc    13320
agcaagcatg gaattttgtt ttgatgtatt caaggagctc aaagtccacc atgccaatga    13380
gaacatcttc tactgcccca ttgccatcat gtcagctcta gccatggtat acctgggtgc    13440
aaaagacagc accaggacac agataaataa ggtgagccta cagttaaaga ttaaaacctt    13500
tgccctgctc aatggagcca cagcacttaa ttgtatgata atgtcccttg gaaactgcat    13560
agctcagagg ctgaaaatct gaaaccagag ttatctaaaa gtgtggccac ctccaactcc    13620
cagagtgtta cccaaatgca ctagctagaa atcttgaaac tggattgcat aacttctttt    13680
tgtcataacc attatttcag ctactattat tttcaattac aggttgttcg ctttgataaa    13740
cttccaggat tcgagacag tattgaagct caggtacaga aataatttca cctccttctc      13800
tatgtccctt tcctctggaa gcaaaataca gcagatgaag caatctctta gctgttccaa    13860
gccctctctg atgagcagct agtgctctgc atccagcagt tgggagaaca ctgttcataa    13920
gaacagagaa aaagaaggaa gtaacagggg attcagaaca aacagaagat aaaactcagg    13980
acaaaaatac cgtgtgaatg aggaaacttg tggatatttg tacgcttaag caagacagct    14040
```

```
agatgattct ggataaatgg gtctggttgg aaaagaagga aagcctggct gatctgctgg     14100
agctagatta ttgcagcagg taggcaggag ttccctagaa aaagtatga gggaattaca     14160 gaagaaaaac agcacaaaat tgtaaatatt ggaaaaggac cacatcagtg tagttactag    14220
cagtaagaca gacaggatga aaaatagttt tgtaaacaga agtatctaac tactttactc    14280
tgttcataca ctatgtaaaa cctactaagt aataaaacta gaataacaac atctttcttt    14340
ctctttgtat tcagtgtggc acatctgtaa acgttcactc ttcacttaga gacatcctca    14400
accaaatcac caaaccaaat gatgtttatt cgttcagcct tgccagtaga ctttatgctg    14460
aagagagata cccaatcctg ccagtaagtt gctctaaaat ctgatctgag tgtatttcca    14520
tgccaaagct ctaccattct gtaatgcaaa acagtcaga gttccacatg tttcactaag     14580
aaaatttctt tttctcttgt tttacaaat gaaagagagg acaaataaca tttctctatc     14640
accgacctga aactctacag tcttcagaga atgaatggct tgctaaaaga atgtcaaatc    14700
ttaccataca gctatttcat attacactac taaatacact ataaggcata gcatgtagta    14760
atacactgta aaatagcttt ttacactact atattattaa tatctgttaa ttccagtctt    14820
gcatttcaca ttttgcaaaac gttttgaaat tcgtatctga aagctgaata ctcttgcttt    14880
acaggaatac ttgcagtgtg tgaaggaact gtatagagga ggcttggaac ctatcaactt    14940
tcaaacagct gcagatcaag ccagagagct catcaattcc tgggtagaaa gtcagacaaa    15000
tggtaaggta gaacatgctt tgtacatagt gagagttggt tcaccctaat actgagaacc    15060
tggatatagc tcagccagcg tgcttttgcgt tcaagcttac cagagctgtt gtatgcctgt    15120
taagcagggc atacagtcat gaggctcttg aaaaatctta acagacaaag ggcaatggaa    15180
aatcggagtt aagggatggt agggataaaa tgcatagaaa gaggtaccac gatttttgatt    15240 tttgccctaa tgcctctctg cgtggttcct caattttct acttcattcc tcatctcctc     15300
agagcattcc tttccctcat gcttgaaaca cagatgaaag actgtgaatt ctaactgaga    15360
tgaaaacatc cacaaccaca caacctctgg tgtggagtca cattctgtga aggcaaaaac    15420
taggccacgt aatctatgtg tgcaagctac gtgtaagcta tgtgtgtgac aggacaatgt    15480
gaggaacata ctatgtgcac aaggactgca gaataaacag gagcaaagtt tttgaagaaa    15540
acagagtaaa atcccgtttt cctcttttgt tacattcttt acatatatct caaatttcct    15600
ctttggttag aagcaagtaa tatttatgtt tcttggtact gtttgggttg aagaccattc    15660
tgggataaga gaaattccag tggttcttcc cctaatcata aaatgtacag gtttagtttt    15720
tttgtaacac agaaatctct tcatcttta tcttttgttg tgattcttta tagagagaga    15780
aacaagactt actgacaata gcagcaagaa aatcaatctt ggaagaacaa gattgcagtt    15840 gcaaaacaa accaatgtcc ttgcccctac atcctcttcc ccataaattc tacattctct     15900
atctaccttg tgcttgccaa catgatatac gtaaactctc ttttcctatt cattcttaaa    15960
ggaattatca gaaatgtcct tcagccaagc tccgtggatt ctcaaactgc aatggttctg    16020
gttaatgcca ttgtcttcaa aggactgtgg gagaaagcat ttaaggatga agacacacaa    16080
gcaatgcctt tcagagtgac tgaggtatat gggcatacct tagagatgta atctagaatt    16140
tatgaagaga gtagacatgt tgttatatga acactgcatt agcgtatctg ctcatttgtc    16200
tgcatctctt tcagacactg tgttaaaagc agggaatttt ccttatgtct ctttcatcac    16260
aatattcctg acattgcaaa gctcctgaga ataacttca gattcccact tttcctaggg     16320
aggtcttcct ggatgagaac aatcaatcat cttaactgta actagatatt tctgcatcta    16380
```

```
agaataatct tgttaaaac tatattctct ctctcttttt tttttttttt ggttctccag    16440
caagaaagca aacctgtgca gatgatgtgg atcc                               16474

<210> SEQ ID NO 33
<211> LENGTH: 8505
<212> TYPE: DNA
<213> ORGANISM: human

<400> SEQUENCE: 33
gtcgacctta agtcctcaga cttggcaagg agaatgtaga tttctacagt atatatgttt      60
tcacaaaagg aaggagagaa acaaaagaaa atggcactga ctaaacttca gctagtggta     120
taggaaagta attctgctta acagagattg cagtgatctc tatgtatgtc ctgaagaatt     180
atgttgtact ttttccctc atttttaaat caaacagtgc tttacagagg tcagaatggt      240
ttctttactg tttgtcaatt ctattatttc aatacagaac aatagcttct ataactgaaa     300
tatatttgct attgtatatt atgattgtcc ctcgaaccat gaacactcct ccagctgaat     360
ttcacaattc ctctgtcatc tgccaggcca ttaagttatt catggaagat ctttgaggaa     420
cactgcaagt tcatatcata aacacatttg aaattgagta ttgttttgca ttgtatggag     480
ctatgttttg ctgtatcctc agaaaaaaag tttgttataa agcattcaca cccataaaaa     540
gatagattta atattccag ctataggaaa gaaagtgcgt ctgctcttca ctctagtctc      600
agttggctcc ttcacatgca cgcttcttta tttctcctat tttgtcaaga aaataatagg     660
tcacgtcttg ttctcactta tgtcctgcct agcatggctc agatgcacgt tgtacataca     720
agaaggatca aatgaaacag acttctggtc tgttactaca accatagtaa taagcacact     780
aactaataat tgctaattat gttttccatc tccaaggttc ccacattttt ctgttttctt     840
aaagatccca ttatctggtt gtaactgaag ctcaatggaa catgagcaat atttcccagt     900
cttctctccc atccaacagt cctgatggat tagcagaaca ggcagaaaac acattgttac     960
ccagaattaa aaactaatat ttgctctcca ttcaatccaa aatggaccta ttgaaactaa    1020
aatctaaccc aatcccatta atgatttct atggcgtcaa aggtcaaact tctgaaggga    1080
acctgtgggt gggtcacaat tcaggctata tattccccag ggctcagcca gtgtctgtac    1140
atacagctag aaagctgtat tgcctttagc actcaagctc aaaaggtaag caactctctg    1200
gaattacctt ctctctatat tagctcttac ttgcacctaa actttaaaaa attaacaatt    1260
attgtgttat gtgttgtatc tttaagggtg aagtacctgc gtgataccc ctataaaaac     1320 ttctcacctg tgtatgcatt ctgcactatt ttattatgtg taaaagcttt gtgtttgttt    1380
tcaggaggct tattctttgt gcttaaaata tgttttaat ttcagaacat cttatcctgt     1440
cgttcactat ctgatatgct ttgcagtttg cctgattaac ttctagccct acagagtgca    1500
cagagagcaa atcatggtg ttcagtgaat tctggggagt tattttaatg tgaaaattct     1560
ctagaagttt aattcctgca aagtgcagct gctgatcact acacaagata aaaatgtggg    1620
gggtgcataa acgtatattc ttacaataat agatacatgt gaacttgtat acagaaaaga    1680
aaatgagaaa aatgtgtgtg cgtatactca cacacgtggt cagtaaaaac ttttgagggg    1740
tttaatacag aaaatccaat cctgaggccc cagcactcag tacgcatata aagggctggg    1800
ctctgaagga cttctgactt tcacagatta tataaatctc aggaaagcaa ctagattcat    1860
gctggctcca aaagctgtgc tttatataag cacactggct atacaatagt tgtacagttc    1920
agctctttat aatagaaaca gacagaacaa gtataaatct tctattggtc tatgtcatga    1980
acaagaattc attcagtggc tctgttttat agtaaacatt gctattttat catgtctgca    2040
```

| | |
|---|---|
| tttctcttct gtctgaatgt caccactaaa atttaactcc acagaaagtt tatactacag | 2100 |
| tacacatgca tatctttgag caaagcaaac catacctgaa agtgcaatag agcagaatat | 2160 |
| gaattacatg cgtgtctttc tcctagacta catgacccca tataaattac attccttatc | 2220 |
| tattctgcca tcaccaaaac aaaggtaaaa atacttttga agatctactc atagcaagta | 2280 |
| gtgtgcaaca aacagatatt tctctacatt tattttaggg aataaaaat aagaaataaa | 2340 |
| atagtcagca agcctctgct ttctcatata tctgtccaaa cctaaagttt actgaaattt | 2400 |
| gctctttgaa tttccagttt tgcaagccta tcagattgtg ttttaatcag aggtactgaa | 2460 |
| aagtatcaat gaattctagc tttcactgaa caaaaatatg tagaggcaac tggcttctgg | 2520 |
| gacagtttgc tacccaaaag acaactgaat gcaaatacat aaatagattt atgaatatgg | 2580 |
| ttttgaacat gcacatgaga ggtggatata gcaacagaca cattaccaca gaattacttt | 2640 |
| aaaactactt gttaacattt aattgcctaa aaactgctcg taatttactg ttgtagccta | 2700 |
| ccatagagta ccctgcatgg tactatgtac agcattccat ccttacattt tcactgttct | 2760 |
| gctgtttgct ctagacaact cagagttcac catgaccaac aagtgtctcc tccaaattgc | 2820 |
| tctcctgttg tgcttctcca ctacagctct ttccatgagc tacaacttgc ttggattcct | 2880 |
| acaaagaagc agcaattttc agtgtcagaa gctcctgtgg caattgaatg ggaggcttga | 2940 |
| atattgcctc aaggacagga tgaactttga catccctgag gagattaagc agctgcagca | 3000 |
| gttccagaag gaggacgccg cattgaccat ctatgagatg ctccagaaca tctttgctat | 3060 |
| tttcagacaa gattcatcta gcactggctg gaatgagact attgttgaga acctcctggc | 3120 |
| taatgtctat catcagataa accatctgaa gacagtcctg gaagaaaaac tggagaaaga | 3180 |
| agatttcacc aggggaaaac tcatgagcag tctgcacctg aaaagatatt atgggaggat | 3240 |
| tctgcattac ctgaaggcca aggagtacag tcactgtgcc tggaccatag tcagagtgga | 3300 |
| aatcctaagg aactttttact tcattaacag acttacaggt tacctccgaa actgaagatc | 3360 |
| tcctagcctg tgcctctggt cgactcgctg atcagcctcg actttgcctt ctagttgcca | 3420 |
| gccatctgtt gtttgcccct cccccgtgcc ttccttgacc ctggaaggtg ccactcccac | 3480 |
| tgtcctttcc taataaaatg aggaaattgc atcgcattgt ctgagtaggt gtcattctat | 3540 |
| tctgggggt ggggtggggc aggacagcaa gggggaggat tgggaagaca atagcaggca | 3600 |
| ctcgaccctc gacttcaaat atgtatccgc tcatgagaca ataaccctga taatgcttc | 3660 |
| aataatattg aaaaggaag agtcctgagg cggaagaac cagctgtgga atgtgtgtca | 3720 |
| gttagggtgt ggaaagtccc caggctcccc agcaggcaga agtatgcaaa gcatgcatct | 3780 |
| caattagtca gcaaccaggt gtggaaagtc cccaggctcc ccagcaggca gaagtatgca | 3840 |
| aagcatgcat ctcaattagt cagcaaccat agtcccgccc ctaactccgc ccatcccgcc | 3900 |
| cctaactccg cccagttccg cccattctcc gccccatggc tgactaattt tttttattta | 3960 |
| tgcagaggcc gaggccgcct cggcctctga gctattccag aagtagtgag gaggcttttt | 4020 |
| tggaggccta ggcttttgca aagatcgatc aagagacagg atgaggatcg tttcgcatga | 4080 |
| ttgaacaaga tggattgcac gcaggttctc cggccgcttg ggtggagagg ctattcggct | 4140 |
| atgactgggc acaacagaca atcggctgct ctgatgccgc cgtgttccgg ctgtcagcgc | 4200 |
| aggggcgccc ggttcttttt gtcaagaccg acctgtccgg tgccctgaat gaactgcaag | 4260 |
| acgaggcagc gcggctatcg tggctggcca cgacgggcgt tccttgcgca gctgtgctcg | 4320 |
| acgttgtcac tgaagcggga aggactggc tgctattggg cgaagtgccg gggcaggatc | 4380 |

```
tcctgtcatc tcaccttgct cctgccgaga aagtatccat catggctgat gcaatgcggc    4440
ggctgcatac gcttgatccg gctacctgcc cattcgacca ccaagcgaaa catcgcatcg    4500
agcgagcacg tactcggatg gaagccggtc ttgtcgatca ggatgatctg gacgaagagc    4560
atcaggggct cgcgccagcc gaactgttcg ccaggctcaa ggcgagcatg cccgacggcg    4620
aggatctcgt cgtgacccat ggcgatgcct gcttgccgaa tatcatggtg gaaaatggcc    4680
gcttttctgg attcatcgac tgtggccggc tgggtgtggc ggaccgctat caggacatag    4740
cgttggctac ccgtgatatt gctgaagagc ttggcggcga atgggctgac cgcttcctcg    4800
tgctttacgg tatcgccgct cccgattcgc agcgcatcgc cttctatcgc cttcttgacg    4860
agttcttctg agcgggactc tggggttcga atgaccgac caagcgacgc ccaacctgcc    4920
atcacgagat ttcgattcca ccgccgcctt ctatgaaagg ttgggcttcg aatcgttt    4980 ccgggacgcc ggctggatga tcctccagcg cggggatctc atgctggagt tcttcgccca    5040
ccctaggggg aggctaactg aaacacggaa ggagacaata ccggaaggaa cccgcgctat    5100
gacggcaata aaaagacaga ataaaacgca cggtgttggg tcgtttgttc ataaacgcgg    5160
ggttcggtcc cagggctggc actctgtcga tacccaccg agaccccatt ggggccaata    5220
cgcccgcgtt tcttcctttt ccccacccca cccccaagt tcgggtgaag cccagggct    5280 cgcagccaac gtcggggcgg caggctgcat atcgaattcc cgcggccgcg gaattcgat    5340 tccatcggtg cagcaagcat ggaattttgt tttgatgtat tcaaggagct caaagtccac    5400
catgccaatg agaacatctt ctactgcccc attgccatca tgtcagctct agccatggta    5460
tacctgggtg caaaagacag caccaggaca cagataaata aggtgagcct acagttaaag    5520
attaaaacct ttgccctgct caatggagcc acagcactta attgtatgat aatgtccctt    5580
ggaaactgca tagctcagag gctgaaaatc tgaaaccaga gttatctaaa agtgtggcca    5640
cctccaactc ccagagtgtt acccaaatgc actagctaga aatcttgaaa ctggattgca    5700
taacttcttt ttgtcataac cattatttca gctactatta ttttcaatta caggttgttc    5760
gctttgataa acttccagga ttcggagaca gtattgaagc tcaggtacag aaataatttc    5820
acctccttct ctatgtccct ttcctctgga agcaaaatac agcagatgaa gcaatctctt    5880
agctgttcca agccctctct gatgagcagc tagtgctctg catccagcag ttgggagaac    5940
actgttcata agaacagaga aaagaagga agtaacaggg gattcagaac aaacagaaga    6000
taaaactcag gacaaaaata ccgtgtgaat gaggaaactt gtggatattt gtacgcttaa    6060
gcaagacagc tagatgattc tggataaatg ggtctggttg gaaaagaagg aaagcctggc    6120
tgatctgctg gagctagatt attgcagcag gtaggcagga gttccctaga gaaaagtatg    6180
agggaattac agaagaaaaa cagcacaaaa ttgtaaatat tggaaaagga ccacatcagt    6240
gtagttacta gcagtaagac agacaggatg aaaaatagtt ttgtaaacag aagtatctaa    6300
ctactttact ctgttcatac actatgtaaa acctactaag taataaaact agaataacaa    6360
catctttctt tctctttgta ttcagtgtgg cacatctgta aacgttcact cttcacttag    6420
agacatcctc aaccaaatca ccaaaccaaa tgatgtttat tcgttcagcc ttgccagtag    6480
actttatgct gaagagagat acccaatcct gccagtaagt tgctctaaaa tctgatctga    6540
gtgtatttcc atgccaaagc tctaccattc tgtaatgcaa aaacagtcag agttccacat    6600
gtttcactaa gaaaatttct ttttctcttg tttttacaaa tgaaagagag acaaataac    6660 atttctctat caccgacctg aaactctaca gtcttcagag aatgaatggc ttgctaaaag    6720
aatgtcaaat cttaccatac agctatttca tattacacta ctaaatacac tataaggcat    6780
```

```
agcatgtagt aatacactgt aaaatagctt tttacactac tatattatta atatctgtta    6840
attccagtct tgcatttcac atttgcaaaa cgttttgaaa ttcgtatctg aaagctgaat    6900
actcttgctt tacaggaata cttgcagtgt gtgaaggaac tgtatagagg aggcttggaa    6960
cctatcaact ttcaaacagc tgcagatcaa gccagagagc tcatcaattc ctgggtagaa    7020
agtcagacaa atggtaaggt agaacatgct ttgtacatag tgagagttgg ttcaccctaa    7080
tactgagaac ctggatatag ctcagccagc gtgctttgcg ttcaagctta ccagagctgt    7140
tgtatgcctg ttaagcaggg catacagtca tgaggctctt gaaaaatctt aacagacaaa    7200
gggcaatgga aaatcggagt taagggatgg tagggataaa atgcatagaa agaggtacca    7260
cgattttgat ttttgcccta atgcctctct gcgtggttcc tcaattttc tacttcattc     7320 ctcatctcct cagagcattc ctttccctca tgcttgaaac acagatgaaa gactgtgaat    7380
tctaactgag atgaaaacat ccacaaccac acaacctctg gtgtggagtc acattctgtg    7440
aaggcaaaaa ctaggccacg taatctatgt gtgcaagcta cgtgtaagct atgtgtgtga    7500
caggacaatg tgaggaacat actatgtgca caaggactgc agaataaaca ggagcaaagt    7560
ttttgaagaa aacagagtaa aatcccgttt tcctcttttg ttacattctt tacatatatc    7620
tcaaatttcc tctttggtta gaagcaagta atatttatgt ttcttggtac tgtttgggtt    7680
gaagaccatt ctgggataag agaaattcca gtggttcttc ccctaatcat aaaatgtaca    7740
ggtttagttt ttttgtaaca cagaaatctc ttcatctttt atcttttgtt gtgattcttt    7800
atagagagag aaacaagact tactgacaat agcagcaaga aaatcaatct tggaagaaca    7860
agattgcagt tgcaaaaaca aaccaatgtc cttgccccta catcctcttc cccataaatt    7920
ctacattctc tatctacctt gtgcttgcca acatgatata cgtaaactct cttttccctat   7980 tcattcttaa aggaattatc agaaatgtcc ttcagccaag ctccgtggat tctcaaactg    8040
caatggttct ggttaatgcc attgtcttca aaggactgtg ggagaaagca tttaaggatg    8100
aagacacaca agcaatgcct ttcagagtga ctgaggtata tgggcatacc ttagagatgt    8160
aatctagaat ttatgaagag agtagacatg ttgttatatg aacactgcat tagcgtatct    8220
gctcatttgt ctgcatctct ttcagacact gtgttaaaag cagggaattt tccttatgtc    8280
tctttcatca caatattcct gacattgcaa agctcctgag aaataacttc agattcccac    8340
ttttcctagg gaggtcttcc tggatgagaa caatcaatca tcttaactgt aactagatat    8400
ttctgcatct aagaataatc tttgttaaaa ctatattctc tctctctttt tttttttttt    8460
tggttctcca gcaagaaagc aaacctgtgc agatgatgtg gatcc                    8505
```

<210> SEQ ID NO 34
<211> LENGTH: 18
<212> TYPE: PRT
<213> ORGANISM: chicken

<400> SEQUENCE: 34

Met Arg Ser Leu Leu Ile Leu Val Leu Cys Phe Leu Pro Leu Ala Ala
1               5                   10                  15

Leu Gly

<210> SEQ ID NO 35
<211> LENGTH: 19
<212> TYPE: PRT
<213> ORGANISM: chicken

<400> SEQUENCE: 35

```
Met Lys Leu Ile Leu Cys Thr Val Leu Ser Leu Gly Ile Ala Ala Val
1               5                   10                  15

Cys Phe Ala

<210> SEQ ID NO 36
<211> LENGTH: 240
<212> TYPE: DNA
<213> ORGANISM: chicken

<400> SEQUENCE: 36
gacatacagc tagaaagctg tattgccttt agcactcaag ctcaaaagac aactcagagt      60
tcaccatggg ctccatcggc gcagcaagca tggaattttg ttttgatgta ttcaaggagc     120
tcaaagtcca ccatgccaat gagaacatct tctactgccc cattgccatc atgtcagctc     180
tagccatggt atacctgggt gcaaaagaca gcaccaggac acagataaat aaggttgttc     240

<210> SEQ ID NO 37
<211> LENGTH: 180
<212> TYPE: DNA
<213> ORGANISM: chicken

<400> SEQUENCE: 37
atggccatgg caggcgtctt cgtgctgttc tctttcgtgc tttgtggctt cctcccagat      60
gctgtctttg gggctgaggt ggactgcagt aggtttccca acgctacaga caaggaaggc     120
aaagatgtat tggtttgcaa caaggacctc cgccccatct gtggtaccga tggagtcact     180

<210> SEQ ID NO 38
<211> LENGTH: 46
<212> TYPE: DNA
<213> ORGANISM: chicken

<400> SEQUENCE: 38
gctgtttgct ctagacaact cagagttcac catgggctcc atcggt                    46

<210> SEQ ID NO 39
<211> LENGTH: 42
<212> TYPE: DNA
<213> ORGANISM: chicken

<400> SEQUENCE: 39
gctgtttgct ctagacaact cagagtcatg gctccatcg gt                         42

<210> SEQ ID NO 40
<211> LENGTH: 45
<212> TYPE: DNA
<213> ORGANISM: chicken

<400> SEQUENCE: 40
gctgtttgct ctagacaact cagagttcac atgggctcca tcggt                     45

<210> SEQ ID NO 41
<211> LENGTH: 46
<212> TYPE: DNA
<213> ORGANISM: chicken

<400> SEQUENCE: 41
gctgtttgct ctagacaact cagagttcac attgggctcc atcggt                    46

<210> SEQ ID NO 42
<211> LENGTH: 44
```

```
<212> TYPE: DNA
<213> ORGANISM: chicken

<400> SEQUENCE: 42
gctgtttgct ctagacaact cagagttcac tgggctccat cggt                    44

<210> SEQ ID NO 43
<211> LENGTH: 37
<212> TYPE: DNA
<213> ORGANISM: chicken

<400> SEQUENCE: 43
gctgtttgct ctagacaact caatgggctc catcggt                            37

<210> SEQ ID NO 44
<211> LENGTH: 20
<212> TYPE: DNA
<213> ORGANISM: chicken

<400> SEQUENCE: 44
gctgcatggg ctccatcggt                                               20

<210> SEQ ID NO 45
<211> LENGTH: 56
<212> TYPE: DNA
<213> ORGANISM: chicken

<400> SEQUENCE: 45
tgcagtaggt ttcccaacgc tacagacaag gaaggcaaag atgtattggt ttgcaa       56

<210> SEQ ID NO 46
<211> LENGTH: 54
<212> TYPE: DNA
<213> ORGANISM: chicken

<400> SEQUENCE: 46
tgcagtaggt ttcccaacgc tacagaaagg aggcaaagat gtattggttt gcaa         54

<210> SEQ ID NO 47
<211> LENGTH: 54
<212> TYPE: DNA
<213> ORGANISM: chicken

<400> SEQUENCE: 47
tgcagtaggt ttcccaacgc tacaacaagg aggcaaagat gtattggttt gcaa         54

<210> SEQ ID NO 48
<211> LENGTH: 53
<212> TYPE: DNA
<213> ORGANISM: chicken

<400> SEQUENCE: 48
tgcagtaggt ttcccaacgc tacacaagga ggcaaagatg tattggtttg caa          53

<210> SEQ ID NO 49
<211> LENGTH: 52
<212> TYPE: DNA
<213> ORGANISM: chicken

<400> SEQUENCE: 49
tgcagtaggt ttcccaacgc taacaaggag gcaaagatgt attggtttgc aa           52

<210> SEQ ID NO 50
```

-continued

<210> SEQ ID NO 50
<211> LENGTH: 52
<212> TYPE: DNA
<213> ORGANISM: chicken

<400> SEQUENCE: 50
tgcagtaggt ttcccaacgc tacaaggaag gcaaagatgt attggtttgc aa    52

<210> SEQ ID NO 51
<211> LENGTH: 51
<212> TYPE: DNA
<213> ORGANISM: chicken

<400> SEQUENCE: 51
tgcagtaggt ttcccaacgc taaaggaagg caaagatgta ttggtttgca a    51

<210> SEQ ID NO 52
<211> LENGTH: 51
<212> TYPE: DNA
<213> ORGANISM: chicken

<400> SEQUENCE: 52
tgcagtaggt ttcccaacgg acaaggaagg caaagatgta ttggtttgca a    51

<210> SEQ ID NO 53
<211> LENGTH: 49
<212> TYPE: DNA
<213> ORGANISM: chicken

<400> SEQUENCE: 53
tgcagtaggt ttcccaacgc aaggaaggca aagatgtatt ggtttgcaa    49

<210> SEQ ID NO 54
<211> LENGTH: 49
<212> TYPE: DNA
<213> ORGANISM: chicken

<400> SEQUENCE: 54
tgcagtaggt ttcccaacgc aaggaaggca aagatgtatt ggtttgcaa    49

<210> SEQ ID NO 55
<211> LENGTH: 34
<212> TYPE: DNA
<213> ORGANISM: chicken

<400> SEQUENCE: 55
tgcagtaggt ttcccaacgc tgtattggtt gcaa    34

<210> SEQ ID NO 56
<211> LENGTH: 60
<212> TYPE: DNA
<213> ORGANISM: chicken

<400> SEQUENCE: 56
agtaggtttc ccaacgctac agacaaggaa ggcaaagatg tattggtttg caacaaggac    60

<210> SEQ ID NO 57
<211> LENGTH: 55
<212> TYPE: DNA
<213> ORGANISM: chicken

<400> SEQUENCE: 57
agtaggtttc ccaacgcaca aggaaggcaa agatgtattg gtttgcaaca aggac    55

<210> SEQ ID NO 58
<211> LENGTH: 56
<212> TYPE: DNA
<213> ORGANISM: chicken

<400> SEQUENCE: 58
tgcagtaggt ttcccaacgc tacagacaag gaaggcaaag atgtattggt ttgcaa        56

<210> SEQ ID NO 59
<211> LENGTH: 55
<212> TYPE: DNA
<213> ORGANISM: chicken

<400> SEQUENCE: 59
tgcagtaggt ttcccaacgc tacaacaagg aaggcaaaga tgtattggtt tgcaa         55

<210> SEQ ID NO 60
<211> LENGTH: 54
<212> TYPE: DNA
<213> ORGANISM: chicken

<400> SEQUENCE: 60
tgcagtaggt ttcccaacgc tacacaagga aggcaaagat gtattggttt gcaa          54

<210> SEQ ID NO 61
<211> LENGTH: 52
<212> TYPE: DNA
<213> ORGANISM: chicken

<400> SEQUENCE: 61
tgcagtaggt ttcccaacgc tacaaggaag gcaaagatgt attggtttgc aa            52

<210> SEQ ID NO 62
<211> LENGTH: 51
<212> TYPE: DNA
<213> ORGANISM: chicken

<400> SEQUENCE: 62
tgcagtaggt ttcccaacgc acaaggaagg caaagatgta ttggtttgca a             51

<210> SEQ ID NO 63
<211> LENGTH: 47
<212> TYPE: DNA
<213> ORGANISM: chicken

<400> SEQUENCE: 63
tgcagtaggt ttcccaacgc ggaaggcaaa gatgtattgg tttgcaa                  47

<210> SEQ ID NO 64
<211> LENGTH: 44
<212> TYPE: DNA
<213> ORGANISM: chicken

<400> SEQUENCE: 64
tgcagtaggt ttcccaacga aggcaaagat gtattggttt gcaa                     44

<210> SEQ ID NO 65
<211> LENGTH: 35
<212> TYPE: DNA
<213> ORGANISM: chicken

<400> SEQUENCE: 65
tgcagtaggt ttcccaacgc tgtattggtt tgcaa                               35

```
<210> SEQ ID NO 66
<211> LENGTH: 25
<212> TYPE: DNA
<213> ORGANISM: chicken

<400> SEQUENCE: 66
tgcagtagga tgtattggtt tgcaa                                          25

<210> SEQ ID NO 67
<211> LENGTH: 120
<212> TYPE: DNA
<213> ORGANISM: chicken

<400> SEQUENCE: 67
gacatacagc tagaaagctg tattgccttt agcactcaag ctcaaaagac aactcagagt    60
tcaccatggg ctccatcggc gcagcaagca tggaattttg ttttgatgta ttcaaggagc   120

<210> SEQ ID NO 68
<211> LENGTH: 120
<212> TYPE: DNA
<213> ORGANISM: chicken

<400> SEQUENCE: 68
gacatacagc tagaaagctg tattgccttt agcactcaag ctcaaaagac aactcagagt    60
tcaccatggg ctccatcggc gcagcaagca tggaattttg ttttgatgta ttcaaggagc   120

<210> SEQ ID NO 69
<211> LENGTH: 60
<212> TYPE: DNA
<213> ORGANISM: chicken

<400> SEQUENCE: 69
agtaggtttc ccaacgctac agacaaggaa ggcaaagatg tattggtttg caacaaggac    60

<210> SEQ ID NO 70
<211> LENGTH: 55
<212> TYPE: DNA
<213> ORGANISM: chicken

<400> SEQUENCE: 70
agtaggtttc ccaacgcaca aggaaggcaa agatgtattg gtttgcaaca aggac         55

<210> SEQ ID NO 71
<211> LENGTH: 19
<212> TYPE: DNA
<213> ORGANISM: Artificial Sequence
<220> FEATURE:
<223> OTHER INFORMATION: primer

<400> SEQUENCE: 71
tctggggttc gaaatgacc                                                 19
```